US009850536B2

(12) United States Patent
Oliphant et al.

(10) Patent No.: US 9,850,536 B2
(45) Date of Patent: *Dec. 26, 2017

(54) MULTIPLEX NUCLEIC ACID REACTIONS

(71) Applicant: ILLUMINA, INC., San Diego, CA (US)

(72) Inventors: Arnold Oliphant, Sunnyvale, CA (US); John R. Stuelpnagel, Santa Barbara, CA (US); Mark S. Chee, Encinitas, CA (US); Scott L. Butler, Sandwich (GB); Jian-Bing Fan, San Diego, CA (US); Min-Jui Richard Shen, Poway, CA (US)

(73) Assignee: Illumina, Inc., San Diego, CA (US)

( * ) Notice: Subject to any disclaimer, the term of this patent is extended or adjusted under 35 U.S.C. 154(b) by 320 days.

This patent is subject to a terminal disclaimer.

(21) Appl. No.: 14/540,832

(22) Filed: Nov. 13, 2014

(65) Prior Publication Data
US 2015/0203913 A1 Jul. 23, 2015

Related U.S. Application Data

(63) Continuation of application No. 13/604,872, filed on Sep. 6, 2012, now Pat. No. 8,906,626, which is a continuation of application No. 12/790,757, filed on May 28, 2010, now Pat. No. 8,288,103, which is a continuation of application No. 12/507,022, filed on Jul. 21, 2009, now abandoned, which is a continuation of application No. 10/194,958, filed on Jul. 12, 2002, now Pat. No. 7,582,420, which is a continuation-in-part of application No. 10/177,727, filed on Jun. 20, 2002, now Pat. No. 7,955,794, which is a continuation-in-part of application No. 09/779,376, filed on Feb. 7, 2001, now abandoned, said application No. 10/177,727 is a continuation-in-part of application No. 09/915,231, filed on Jul. 24, 2001, now Pat. No. 6,890,741, which is a continuation-in-part of application No. 09/779,376, said application No. 10/177,727 is a continuation-in-part of application No. 09/931,285, filed on Aug. 16, 2001, now Pat. No. 6,913,884.

(60) Provisional application No. 60/305,118, filed on Jul. 12, 2001, provisional application No. 60/311,271, filed on Aug. 9, 2001, provisional application No. 60/336,958, filed on Dec. 3, 2001, provisional application No. 60/341,827, filed on Dec. 17, 2001, provisional application No. 60/180,810, filed on Feb. 7, 2000, provisional application No. 60/234,732, filed on Sep. 22, 2000, provisional application No. 60/234,143, filed on Sep. 21, 2000, provisional application No. 60/297,609, filed on Jun. 11, 2001.

(51) Int. Cl.
C12P 19/34 (2006.01)
C12Q 1/68 (2006.01)
C12M 1/34 (2006.01)
C12M 3/00 (2006.01)
C07H 21/02 (2006.01)
C07H 21/04 (2006.01)
C07H 21/00 (2006.01)

(52) U.S. Cl.
CPC ......... *C12Q 1/6876* (2013.01); *C12Q 1/6834* (2013.01); *C12Q 1/6837* (2013.01); *C12Q 2600/16* (2013.01); *Y10T 436/143333* (2015.01)

(58) Field of Classification Search
USPC ..................................................... 435/287.2
See application file for complete search history.

(56) References Cited

U.S. PATENT DOCUMENTS

| 4,200,110 A | 4/1980 | Peterson et al. |
| 4,349,510 A | 9/1982 | Kolehmainen |
| 4,499,052 A | 2/1985 | Fulwyler |
| 4,499,053 A | 2/1985 | Jones |
| 4,563,419 A | 1/1986 | Ranki et al. |

(Continued)

FOREIGN PATENT DOCUMENTS

| EP | 0 139 489 | 5/1985 |
| EP | 0 238 332 | 9/1987 |

(Continued)

OTHER PUBLICATIONS

Abel, et al., "Fiber-Optic Evanescent Wave Biosensor for the Detection of Oligonucleotides", Analytical Chemistry, vol. 68, Sep. 1996, 2905-2912.
Abramson, et al., "Nucleic acid amplification technologies", Current Opinion in Biotechnology, 4, 1993, 41-47.
Akama, et al., "Restriction landmark genomic scanning (RLGS-M) based genome-wide scanning of mouse liver tumors for alterations in DNA methylation status", Cancer Res. 57 (15):3294-3299 (1997), 1997, 3294-3299.
Anonymous, Pierce Chemical Company Catalog, 1994, 1994, N/A.
Anonymous, "Fluorescent Microspheres", Tech. Note 19, Bangs Laboratories, (Fishers, In), Feb. 1997.

(Continued)

*Primary Examiner* — Frank Lu
(74) *Attorney, Agent, or Firm* — Knobbe, Martens, Olson & Bear LLP

(57) ABSTRACT

A method for detecting nucleic acids by (a) providing a sample having target nucleic acids, each nucleic acid having contiguous first, second, and third domains; (b) contacting the sample with probe sets to form hybridization complexes, wherein each probe set includes (i) a first probe having a sequence that is complementary to the first domain; and (ii) a second probe having a sequence substantially complementary to the third domain; (c) extending the first probes along the second domains of the complexes while the complexes are immobilized on a solid support; (d) ligating the extended first probes to the second probes to form templates; (e) amplifying the templates with primers that are complementary to the first and second priming sequences to produce amplicons; and (f) detecting the amplicons on the surface of a nucleic acid array.

19 Claims, 14 Drawing Sheets

(56) References Cited

U.S. PATENT DOCUMENTS

| | | |
|---|---|---|
| 4,582,789 A | 4/1986 | Sheldon et al. |
| 4,672,040 A | 6/1987 | Josephson |
| 4,682,895 A | 7/1987 | Costello |
| 4,683,195 A | 7/1987 | Mullins et al. |
| 4,683,202 A | 7/1987 | Mullis et al. |
| 4,687,732 A | 8/1987 | Ward et al. |
| 4,707,454 A | 11/1987 | Hendrix |
| 4,751,177 A | 6/1988 | Stabinsky |
| 4,785,814 A | 11/1988 | Kane |
| 4,822,746 A | 4/1989 | Walt |
| 4,824,789 A | 4/1989 | Yafuso et al. |
| 4,876,187 A | 10/1989 | Duck et al. |
| 4,879,097 A | 11/1989 | Whitehead et al. |
| 4,882,269 A | 11/1989 | Schneider et al. |
| 4,883,750 A | 11/1989 | Whiteley et al. |
| 4,921,805 A | 5/1990 | Gebeyehu et al. |
| 4,988,617 A | 1/1991 | Landegren et al. |
| 4,999,306 A | 3/1991 | Yafuso et al. |
| 5,002,867 A | 3/1991 | Macevicz |
| 5,011,769 A | 4/1991 | Duck et al. |
| 5,028,545 A | 7/1991 | Soini |
| 5,043,272 A | 8/1991 | Hartley |
| 5,087,820 A | 2/1992 | Kearns |
| 5,104,791 A | 4/1992 | Abbott et al. |
| 5,104,792 A | 4/1992 | Silver et al. |
| 5,105,305 A | 4/1992 | Betzig et al. |
| 5,114,864 A | 5/1992 | Walt |
| 5,130,238 A | 7/1992 | Malek |
| 5,132,242 A | 7/1992 | Cheung |
| 5,143,853 A | 9/1992 | Walt |
| 5,143,854 A | 9/1992 | Pirrung |
| 5,144,136 A | 9/1992 | Kubisiak |
| 5,175,082 A | 12/1992 | Jeffreys |
| 5,176,881 A | 1/1993 | Sepaniak et al. |
| 5,185,243 A | 2/1993 | Ullman et al. |
| 5,194,300 A | 3/1993 | Cheung |
| 5,202,231 A | 4/1993 | Drmanac et al. |
| 5,232,829 A | 8/1993 | Longiaru et al. |
| 5,242,794 A | 9/1993 | Whiteley et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt et al. |
| 5,298,741 A | 3/1994 | Walt et al. |
| 5,302,509 A | 4/1994 | Cheeseman |
| 5,314,809 A | 5/1994 | Erlich et al. |
| 5,320,814 A | 6/1994 | Walt et al. |
| 5,357,590 A | 10/1994 | Auracher |
| 5,380,489 A | 1/1995 | Sutton et al. |
| 5,387,505 A | 2/1995 | Wu et al. |
| 5,399,491 A | 3/1995 | Kacian et al. |
| 5,403,711 A | 4/1995 | Walder et al. |
| 5,409,818 A | 4/1995 | Davey et al. |
| 5,427,930 A | 6/1995 | Birkenmeyer et al. |
| 5,435,724 A | 7/1995 | Goodman et al. |
| 5,445,934 A | 8/1995 | Fodor et al. |
| 5,445,970 A | 8/1995 | Rohr |
| 5,455,166 A | 10/1995 | Walker |
| 5,474,895 A | 12/1995 | Ishii et al. |
| 5,481,629 A | 1/1996 | Tabuchi |
| 5,489,507 A | 2/1996 | Chehab |
| 5,494,798 A | 2/1996 | Gerdt et al. |
| 5,494,810 A | 2/1996 | Barany et al. |
| 5,496,997 A | 3/1996 | Pope |
| 5,503,980 A | 4/1996 | Cantor |
| 5,512,439 A | 4/1996 | Hornes et al. |
| 5,512,490 A | 4/1996 | Walt et al. |
| 5,516,635 A | 5/1996 | Ekins et al. |
| 5,518,883 A | 5/1996 | Soini |
| 5,521,065 A | 5/1996 | Whiteley et al. |
| 5,541,311 A | 7/1996 | Dahlberg et al. |
| 5,545,531 A | 8/1996 | Rava et al. |
| 5,554,516 A | 9/1996 | Kacian et al. |
| 5,565,324 A | 10/1996 | Still et al. |
| 5,567,587 A | 10/1996 | Kohne |
| 5,571,639 A | 11/1996 | Hubbell et al. |
| 5,573,907 A | 11/1996 | Carrino et al. |
| 5,573,909 A | 11/1996 | Singer et al. |
| 5,575,849 A | 11/1996 | Honda et al. |
| 5,578,832 A | 11/1996 | Trulson et al. |
| 5,593,840 A | 1/1997 | Bhatnagar et al. |
| 5,595,890 A | 1/1997 | Newton et al. |
| 5,595,915 A | 1/1997 | Geysen |
| 5,601,978 A | 2/1997 | Burczak et al. |
| 5,604,097 A | 2/1997 | Brenner |
| 5,614,402 A | 3/1997 | Dahlberg et al. |
| 5,632,957 A | 5/1997 | Heller et al. |
| 5,633,972 A | 5/1997 | Walt et al. |
| 5,639,603 A | 6/1997 | Dower et al. |
| 5,649,576 A | 7/1997 | Kirk |
| 5,656,241 A | 8/1997 | Seifert et al. |
| 5,660,988 A | 8/1997 | Duck et al. |
| 5,674,698 A | 10/1997 | Zarling et al. |
| 5,679,524 A | 10/1997 | Nikiforov et al. |
| 5,681,697 A | 10/1997 | Urdea et al. |
| 5,690,894 A | 11/1997 | Pinkel et al. |
| 5,695,940 A | 12/1997 | Drmanac et al. |
| 5,705,365 A | 1/1998 | Ryder et al. |
| 5,710,029 A | 1/1998 | Ryder et al. |
| 5,719,028 A | 2/1998 | Dahlberg et al. |
| 5,733,729 A | 3/1998 | Lipshutz et al. |
| 5,744,305 A | 4/1998 | Fodor et al. |
| 5,763,175 A | 6/1998 | Brenner |
| 5,770,157 A | 6/1998 | Cargill et al. |
| 5,780,231 A | 7/1998 | Brenner |
| 5,786,146 A | 7/1998 | Herman et al. |
| 5,792,607 A | 8/1998 | Backman et al. |
| 5,795,714 A | 8/1998 | Cantor et al. |
| 5,795,716 A | 8/1998 | Chee et al. |
| 5,800,992 A | 9/1998 | Fodor et al. |
| 5,804,376 A | 9/1998 | Braxton et al. |
| 5,807,522 A | 9/1998 | Brown et al. |
| 5,814,524 A | 10/1998 | Walt |
| 5,830,655 A | 11/1998 | Monforte et al. |
| 5,830,711 A | 11/1998 | Barany et al. |
| 5,834,758 A | 11/1998 | Trulson et al. |
| 5,837,196 A | 11/1998 | Pinkel et al. |
| 5,840,256 A | 11/1998 | Demers et al. |
| 5,843,669 A | 12/1998 | Kaiser |
| 5,843,767 A | 12/1998 | Beattie |
| 5,846,710 A | 12/1998 | Bajaj |
| 5,846,717 A | 12/1998 | Brow et al. |
| 5,846,719 A | 12/1998 | Brenner |
| 5,849,544 A | 12/1998 | Harris |
| 5,853,989 A | 12/1998 | Jeffreys et al. |
| 5,854,033 A | 12/1998 | Lizardi |
| 5,854,684 A | 12/1998 | Stabile et al. |
| 5,856,083 A | 1/1999 | Chelsky et al. |
| 5,858,732 A | 1/1999 | Solomon et al. |
| 5,863,708 A | 1/1999 | Zanzucchi et al. |
| 5,863,722 A | 1/1999 | Brenner |
| 5,866,321 A | 2/1999 | Matsue et al. |
| 5,869,252 A | 2/1999 | Bouma et al. |
| 5,871,917 A | 2/1999 | Duffy |
| 5,871,928 A | 2/1999 | Fodor et al. |
| 5,874,219 A | 2/1999 | Rava et al. |
| 5,876,924 A | 3/1999 | Zhang et al. |
| 5,888,723 A | 3/1999 | Sutton et al. |
| 5,888,778 A | 3/1999 | Shuber |
| 5,888,779 A | 3/1999 | Kacian et al. |
| 5,888,819 A | 3/1999 | Goelet et al. |
| 5,900,481 A | 5/1999 | Lough et al. |
| 5,922,617 A | 7/1999 | Wang et al. |
| 5,935,793 A | 8/1999 | Wong et al. |
| 5,942,391 A | 8/1999 | Zhang et al. |
| 5,952,174 A | 9/1999 | Nikiforov et al. |
| 5,974,164 A | 10/1999 | Chee et al. |
| 5,976,797 A | 11/1999 | Mitsuhashi |
| 5,981,180 A | 11/1999 | Chandler et al. |
| 5,994,066 A | 11/1999 | Bergeron et al. |
| 5,998,175 A | 12/1999 | Akhavan-Tafti |
| 6,001,564 A | 12/1999 | Bergeron et al. |
| 6,013,440 A | 1/2000 | Lipshutz et al. |

(56) References Cited

U.S. PATENT DOCUMENTS

| | | | |
|---|---|---|---|
| 6,013,456 A | 1/2000 | Akhavan-Tafti |
| 6,017,738 A | 1/2000 | Morris et al. |
| 6,023,540 A | 2/2000 | Walt et al. |
| 6,025,601 A | 2/2000 | Trulson et al. |
| 6,027,840 A | 2/2000 | Yoon |
| 6,027,889 A | 2/2000 | Barany et al. |
| 6,037,186 A | 3/2000 | Stimpson |
| 6,040,138 A | 3/2000 | Lockhart et al. |
| 6,045,996 A | 4/2000 | Cronin et al. |
| 6,051,380 A | 4/2000 | Sosnowski et al. |
| 6,054,564 A | 4/2000 | Barany et al. |
| 6,060,245 A | 5/2000 | Sorge |
| 6,066,454 A | 5/2000 | Lipshutz et al. |
| 6,071,748 A | 6/2000 | Modlin et al. |
| 6,074,614 A | 6/2000 | Hafeman |
| 6,083,753 A | 7/2000 | Kelly et al. |
| 6,083,763 A | 7/2000 | Balch |
| 6,090,558 A | 7/2000 | Butler et al. |
| 6,096,496 A | 8/2000 | Frankel et al. |
| 6,110,678 A | 8/2000 | Weisburg et al. |
| 6,124,102 A | 9/2000 | Fodor et al. |
| 6,133,436 A | 10/2000 | Koster et al. |
| 6,143,495 A | 11/2000 | Lizardi et al. |
| 6,172,218 B1 | 1/2001 | Brenner |
| 6,183,960 B1 | 2/2001 | Lizardi |
| 6,185,561 B1 | 2/2001 | Balaban et al. |
| 6,188,783 B1 | 2/2001 | Balaban et al. |
| 6,197,506 B1 | 3/2001 | Fodor et al. |
| 6,200,737 B1 | 3/2001 | Walt et al. |
| 6,200,756 B1 | 3/2001 | Herman et al. |
| 6,210,884 B1 | 4/2001 | Lizardi |
| 6,214,556 B1 | 4/2001 | Olek et al. |
| 6,221,603 B1 | 4/2001 | Mahtani |
| 6,225,064 B1 | 5/2001 | Uematsu et al. |
| 6,225,625 B1 | 5/2001 | Pirrung et al. |
| 6,229,911 B1 | 5/2001 | Balaban et al. |
| 6,255,625 B1 | 5/2001 | Pirrung et al. |
| 6,248,539 B1 | 6/2001 | Ghadiri et al. |
| 6,251,594 B1 | 6/2001 | Gonzalgo et al. |
| 6,251,639 B1 | 6/2001 | Kurn |
| 6,261,776 B1 | 7/2001 | Pirrung et al. |
| 6,265,171 B1 | 7/2001 | Herman et al. |
| 6,266,459 B1 | 7/2001 | Walt et al. |
| 6,268,148 B1 | 7/2001 | Barany et al. |
| 6,274,320 B1 | 8/2001 | Rothberg et al. |
| 6,274,323 B1 | 8/2001 | Bruchez et al. |
| 6,280,935 B1 | 8/2001 | Macevicz |
| 6,280,949 B1 | 8/2001 | Lizardi |
| 6,284,465 B1 | 9/2001 | Wolber |
| 6,291,166 B1 | 9/2001 | Gerdes et al. |
| 6,291,183 B1 | 9/2001 | Pirrung et al. |
| 6,300,071 B1 | 10/2001 | Vuylsteke et al. |
| 6,306,643 B1 | 10/2001 | Gentalen et al. |
| 6,308,170 B1 | 10/2001 | Balaban et al. |
| 6,309,822 B1 | 10/2001 | Fodor et al. |
| 6,316,229 B1 | 11/2001 | Lizardi et al. |
| 6,327,410 B1 | 12/2001 | Walt et al. |
| 6,329,150 B1 | 12/2001 | Lizardi |
| 6,331,393 B1 | 12/2001 | Laird et al. |
| 6,335,165 B1 | 1/2002 | Navot et al. |
| 6,342,389 B1 | 1/2002 | Cubicciotti |
| 6,346,413 B1 | 2/2002 | Fodor et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,399,365 B2 | 6/2002 | Besemer et al. |
| 6,403,320 B1 | 6/2002 | Read et al. |
| 6,416,952 B1 | 7/2002 | Pirrung et al. |
| 6,429,027 B1 | 8/2002 | Chee et al. |
| 6,440,667 B1 | 8/2002 | Fodor et al. |
| 6,440,677 B2 | 8/2002 | Lipshutz et al. |
| 6,451,536 B1 | 9/2002 | Fodor et al. |
| 6,491,871 B1 | 12/2002 | Fodor et al. |
| 6,511,810 B2 | 1/2003 | Bi et al. |
| 6,534,293 B1 | 3/2003 | Barany et al. |
| 6,544,732 B1 | 4/2003 | Chee et al. |
| 6,544,739 B1 | 4/2003 | Fodor et al. |
| 6,576,424 B2 | 6/2003 | Fodor et al. |
| 6,604,902 B2 | 8/2003 | Norris et al. |
| 6,605,432 B1 | 8/2003 | Huang |
| 6,610,482 B1 | 8/2003 | Fodor et al. |
| 6,618,679 B2 | 9/2003 | Loehrlein et al. |
| 6,627,402 B2 | 9/2003 | Wallace |
| 6,646,243 B2 | 11/2003 | Pirrung et al. |
| 6,812,005 B2 | 11/2004 | Fan et al. |
| 6,858,394 B1 | 2/2005 | Chee et al. |
| 6,859,570 B2 | 2/2005 | Walt et al. |
| 6,942,968 B1 | 9/2005 | Dickinson et al. |
| 7,033,754 B2 | 4/2006 | Chee |
| 7,060,431 B2 | 6/2006 | Chee et al. |
| 7,115,884 B1 | 10/2006 | Walt |
| 7,510,841 B2 | 3/2009 | Stuelpnagel et al. |
| 7,582,420 B2 | 9/2009 | Oliphant et al. |
| 7,612,020 B2 | 11/2009 | Stuelpnagel et al. |
| 7,955,794 B2 | 6/2011 | Shen et al. |
| 8,003,354 B2 * | 8/2011 | Shen ............. C12Q 1/6827 435/287.2 |
| 8,288,103 B2 | 10/2012 | Oliphant et al. |
| 8,906,626 B2 * | 12/2014 | Oliphant ............. C12Q 1/6834 435/6.12 |
| 2001/0029049 A1 | 10/2001 | Walt et al. |
| 2002/0006617 A1 | 1/2002 | Fan et al. |
| 2002/0039728 A1 | 4/2002 | Kain |
| 2002/0051971 A1 | 5/2002 | Stuelpnagel et al. |
| 2002/0064779 A1 | 5/2002 | Landergren |
| 2002/0122612 A1 | 9/2002 | Walt et al. |
| 2002/0132241 A1 | 9/2002 | Fan et al. |
| 2002/0137086 A1 | 9/2002 | Olek et al. |
| 2002/0150921 A1 | 10/2002 | Barany et al. |
| 2002/0168645 A1 | 11/2002 | Taylor |
| 2002/0172946 A1 | 11/2002 | Fan et al. |
| 2002/0177141 A1 | 11/2002 | Chee et al. |
| 2003/0027126 A1 | 2/2003 | Walt et al. |
| 2003/0036064 A1 | 2/2003 | Stuelpnagel et al. |
| 2003/0082600 A1 | 5/2003 | Olek et al. |
| 2003/0108900 A1 | 6/2003 | Oliphant et al. |
| 2003/0119025 A1 | 6/2003 | Olek et al. |
| 2003/0129620 A1 | 7/2003 | Olek et al. |
| 2003/0162194 A1 | 8/2003 | Olek et al. |
| 2003/0170684 A1 | 9/2003 | Fan |
| 2003/0211489 A1 | 11/2003 | Shen |
| 2003/0228599 A1 | 12/2003 | Straus |
| 2004/0023230 A1 | 2/2004 | Olek et al. |
| 2004/0072197 A1 | 4/2004 | Jones et al. |
| 2004/0101835 A1 | 5/2004 | Willis et al. |
| 2004/0121364 A1 | 6/2004 | Chee et al. |
| 2004/0137473 A1 | 7/2004 | Wigler et al. |
| 2004/0137498 A1 | 7/2004 | Fan et al. |
| 2004/0234960 A1 | 11/2004 | Olek et al. |
| 2004/0248090 A1 | 12/2004 | Olek et al. |
| 2004/0259100 A1 | 12/2004 | Gunderson et al. |
| 2004/0265814 A1 | 12/2004 | Distler et al. |
| 2005/0053937 A1 | 3/2005 | Berlin |
| 2005/0214825 A1 | 9/2005 | Stuelpnagel |
| 2006/0008824 A1 | 1/2006 | Ronaghi et al. |
| 2006/0019304 A1 | 1/2006 | Hardenbol et al. |
| 2006/0275782 A1 | 12/2006 | Gunderson et al. |
| 2008/0242555 A1 | 10/2008 | Shen et al. |
| 2009/0233802 A1 | 9/2009 | Bignell et al. |
| 2010/0015626 A1 | 1/2010 | Oliphant et al. |
| 2010/0311064 A1 | 12/2010 | Oliphant et al. |
| 2013/0244882 A1 | 9/2013 | Oliphant et al. |

FOREIGN PATENT DOCUMENTS

| | | |
|---|---|---|
| EP | 0 246 864 | 11/1987 |
| EP | 0 269 764 | 6/1988 |
| EP | 0 336 731 | 10/1989 |
| EP | 0 357 336 | 3/1990 |
| EP | 0 392 546 | 10/1990 |
| EP | 0392546 | 10/1990 |
| EP | 0 439 182 | 7/1991 |
| EP | 0 478 319 | 4/1992 |
| EP | 0478319 | 4/1992 |

(56) References Cited

FOREIGN PATENT DOCUMENTS

| | | |
|---|---|---|
| EP | 0 320 308 | 11/1993 |
| EP | 0336731 | 5/1994 |
| EP | 0 614 987 | 9/1994 |
| EP | 0439182 | 4/1996 |
| EP | 0 723 146 | 7/1996 |
| EP | 0723146 | 7/1996 |
| EP | 0799897 | 10/1997 |
| EP | 0 799 897 | 11/1998 |
| EP | 1 121 465 | 9/2002 |
| GB | 2 156 074 | 10/1985 |
| WO | WO 86/03782 | 7/1986 |
| WO | WO 97/33737 | 9/1987 |
| WO | WO 89/09835 | 10/1989 |
| WO | WO 89/11101 | 11/1989 |
| WO | WO 89/12696 | 12/1989 |
| WO | WO 90/01069 | 2/1990 |
| WO | WO 90/01564 | 2/1990 |
| WO | WO 91/006678 | 5/1991 |
| WO | WO 91/17442 | 11/1991 |
| WO | WO 93/02360 | 2/1993 |
| WO | WO 93/25563 | 12/1993 |
| WO | WO 94/02515 | 2/1994 |
| WO | WO 95/00667 | 1/1995 |
| WO | WO 95/04160 | 2/1995 |
| WO | WO 95/05480 | 2/1995 |
| WO | WO 95/16918 | 6/1995 |
| WO | WO 95/21271 | 8/1995 |
| WO | WO 95/25538 | 9/1995 |
| WO | WO 96/03212 | 2/1996 |
| WO | WO 99/05320 | 2/1996 |
| WO | WO 96/15271 | 5/1996 |
| WO | WO 96/17958 | 6/1996 |
| WO | WO 02/057491 | 7/1996 |
| WO | WO 96/30392 | 10/1996 |
| WO | WO 96/31622 | 10/1996 |
| WO | WO 97/14028 | 4/1997 |
| WO | WO 97/31256 | 8/1997 |
| WO | WO 97/40385 | 10/1997 |
| WO | WO 97/04559 | 12/1997 |
| WO | WO 97/45559 | 12/1997 |
| WO | WO 97/46704 | 12/1997 |
| WO | WO 98/04746 | 2/1998 |
| WO | WO 98/08092 | 2/1998 |
| WO | WO 98/13523 | 4/1998 |
| WO | WO 98/29736 | 7/1998 |
| WO | WO 98/31836 | 7/1998 |
| WO | WO 98/37230 | 8/1998 |
| WO | WO 98/40726 | 9/1998 |
| WO | WO 98/50782 | 11/1998 |
| WO | WO 98/53093 | 11/1998 |
| WO | WO 98/53300 | 11/1998 |
| WO | WO 98/56952 | 12/1998 |
| WO | WO 98/59243 | 12/1998 |
| WO | WO 99/01580 | 1/1999 |
| WO | WO 99/18434 | 4/1999 |
| WO | WO 99/39001 | 8/1999 |
| WO | WO 99/53102 | 10/1999 |
| WO | WO 99/60170 | 11/1999 |
| WO | WO 99/64867 | 12/1999 |
| WO | WO 99/67414 | 12/1999 |
| WO | WO 99/67641 | 12/1999 |
| WO | WO 00/04372 | 1/2000 |
| WO | WO 00/13004 | 3/2000 |
| WO | WO 00/14193 | 3/2000 |
| WO | WO 00/16101 | 3/2000 |
| WO | WO 00/26401 | 5/2000 |
| WO | WO 00/39587 | 7/2000 |
| WO | WO 00/47996 | 8/2000 |
| WO | WO 00/48000 | 8/2000 |
| WO | WO 00/58516 | 10/2000 |
| WO | WO 00/60332 | 10/2000 |
| WO | WO 00/63437 | 10/2000 |
| WO | WO 00/70090 | 11/2000 |
| WO | WO 00/71243 | 11/2000 |
| WO | WO 00/71992 | 11/2000 |
| WO | WO 00/71995 | 11/2000 |
| WO | WO 00/75373 | 12/2000 |
| WO | WO 01/06012 | 1/2001 |
| WO | WO 01/20035 | 3/2001 |
| WO | WO 01/77377 | 4/2001 |
| WO | WO 02/00927 | 7/2001 |
| WO | WO 01/57269 | 8/2001 |
| WO | WO 01/62961 | 8/2001 |
| WO | WO 02/34942 | 10/2001 |
| WO | WO 02/18649 | 3/2002 |
| WO | WO 02/083705 | 4/2002 |
| WO | WO 02/61143 | 8/2002 |
| WO | WO 02/086163 | 10/2002 |
| WO | WO 03/048732 | 6/2003 |
| WO | WO 04/051224 | 6/2004 |
| WO | WO 05/068656 | 7/2005 |

OTHER PUBLICATIONS

Anonymous, "Microsphere Detection Guide", Bang Laboratories, (Fisher, In), Sep. 1998.
Anonymous, "Microsphere Selection Guide", Bangs Laboratories, Inc. (Fisher, IN), 1998.
Arnheim, et al., "#16 Polymerase chain reaction strategy", Ann. Rev. Of Biochem., 1992, 61, 131-56.
Aslam, et al., "Bioconjugation: Protein Coupling Techniques for Biomedical Sciences", Grove's Dictionaries, New York, 1998.
Ausubel, et al., "A Compendium of Methods for Current Protocols in Molecular Biology", Short Protocols in Molecular Biology, 2nd Ed., John Wiley & Sons, New York, 1992.
Baner, et al., "More keys to padlock probes:", Current opinion in biotechnology, 2001, 12, 11-15, 2001, 11-15.
Baner, "Signal amplification of padlock probes by rolling circle replication", Nucleic Acids Research, vol. 26(22), 1998, 5073-5078.
Bangs, L. B., "Immunological Applications of Microspheres", The Latex Course, Bangs Laboratories (Carmel, In), Apr. 1996, N/A.
Barany, "Genetic disease detection and DNA amplification using cloned thermostable ligase", Proceedings of the National Academy of Sciences USA, 88, 1991, 189-193.
Barany, "Genetic Disease Detection and DNA Amplifiction Using Cloned Thermostable Ligase", PNAS 88, 1991, 189-193.
Barnard, "A Fibre-Optic Chemical Sensor with Discrete Sensing Sites", Nature, vol. 353, Sep. 1991, 338-340.
Baylin, et al., "DNA hypermethylation in tumorigenesis: epigenetics joins genetics", Trends Genet., 16(4), 2000, 168-174.
Berg, et al., "Hybrid PCR Sequencing: Sequencing of PCR products using a universal primer", BioTechniques, 17 (5):896-901 (1994), 1994, 896-901.
Bestor, "Gene silencing. Methylation meets acetylation.", Nature, 393 (6683), 1998, 311-312.
Boguszewski, Cesar L. et al., "Cloning of Two Novel Growth Hormone Transcripts Expressed in Human Placenta", Journal of Clinical Endocrinology and Metabolism, vol. 83 (8), 2878-2885.
Broude, et al., "Enhanced DNA sequencing by hybridization", PNAS, 91, 1994, 3072-3076.
Brownie, et al., "#19 The elimination of primer-dimer accumulation in PCR", Nuc. Acid Res. 25(16), 1997, 3235-41.
Chamberlain, et al., "#17 Deletion screening of Duchenne musular dystrophy locus via multiplex DNA amplification", Nuc. Acid. Res. 16, 1988, 11141-56.
Chee, "#15 Accessing genetic information with high-density DNA arrays", Science, 274, 1996, 610-614.
Chen, "A Microsphere-Based Assy for Multiplexed Single Nucleotide Polymorphism Analysis Using Single Base Chain Extension", Genome Research, vol. 10(4), 2000, 549-557.
Conner, et al., "Detection of sickle cell beta(s)-globin allele by hybridization with synthetic oligonucleotides", PNAS, 80, 1983, 272-282.
Corder, E H., "Gene dose of apolipoportein E type 4 allele and the risk of Alzheimer's disease in late onset families", Science, 1993, vol. 261, 921-923.

(56) References Cited

OTHER PUBLICATIONS

Costello, et al., "Aberrant CpG-Island methylation has non-random and tumour-type-specific patterns", Nat Genet 24(2):132-138 (2000).
Costello, J F., "Methylation Matters", Journal of Medical Genetics, London, Great Britain, vol. 38., No. 5., May 2001 p. 285-303, XP008018005, 285-303.
Cunin, "Biomolecular screening with encoded porous-silicon photonic crystals", Nature Materials, 1, 2002, 39-41.
Czarnik, "Illuminating the SNP Genomic Code", Modern Drug Discovery, vol. 1(2), 1998, 49-55.
Dahl, et al., "DNA methylation analysis techniques", Biogerontology, 4 (4):233-250 (2003).
Dragich, et al., "Rett syndrome: a surprising result of mutation in MECP2", Human Mol. Genetics 9, 2000, 2365-2375.
Drmanac, et al., "Prospects for a Minaturized, Simplified and Frugal Human Genome Project", Scientia Yugoslavica vol. 16(1-2), 1990, 97-107.
Drmanac, "Sequencing by Hybridization", Automated DNA Sequencing and Analysis, ed. M., 1994, 29-36.
Drmanac, et al., "Sequencing by Hybridization (SBH) with Oligonucleotide Probes as an Integral Approach for the Analysis of Complex Genomes", Inter. J. of Genome Research vol. 1 No. 1, World Scientific Publishing Co., 1992, 59-79.
Drmanac, et al., "Sequencing by Oligonucleotide Hybridization: A Promising Framework in Decoding of the Genome Program?", The First International Conf. of Electrophoresis.Florida State Univ., Apr. 10-13, 1990, 47-59.
Drmanac, R. et al., "Sequencing of megabase plus DNA by hybridization: theory and method", Genomics, vol. 4., 1989, 114-128.
Eads, et al., "MethyLight: a high-throughput assay to measure DNA methylation", Nucleic Acids Research, 28(8), e32, 2000, i-viii.
Fan, et al., "Parallel Genotyping of Human SNPs Using Generic High-density Oligonucleotide Tag Arrays", Genome Research, vol. 10, 2000, 853-860.
Feil, et al., "Methylation analysis on individual chromosomes: improved protocol for bisuphphite genomic sequencing", Nucleic Acids Res. 22 (4):695-696 (1994).
Feinberg, et al., "Hypomethylation distinguishes genes of some human cancers from their normal counterparts", Nature. 301 (5895):89-92 (1983).
Ferguson, J A. et al., "A Fiber-Optic DNA Biosensor Microarray for the Analysis of Gene Expression", Nature Biotechnol. vol. 14, 1996, 1681-1684.
Fodor, et al., "#20 Light-Directed, Spatially Addressable Parallel Chemical Synthesis", Science, 251, 4995, 1991, 767-73.
Frommer, et al., "A genomic sequencing protocol that yields a positive display of 5-methylcytosine residues in individual DNA strands", Proc Natl Acad Sci USA, 89 (5):1827-1831 (1992).
Fuh, "Single Fibre Optic Fluorescence pH Probe", Analyst, vol. 112, 1987, 1159-1163.
Gerry, et al., "Universal DNA Microarray Method for Multiplex Detection of Low Abundance Point Mutations", J. Mol. Biol., vol. 292, 1999, 251-262.
Golub, et al., "Molecular classification of cancer: class discovery and class prediction by gene expression monitoring", Science 286 (5439) :531-7 (1999).
Gonzalgo, et al., "Identification and characterization of differentially methylated regions of genomic DNA by methylation-sensitive arbitrarily primed PCR", Cancer Res. 57 (4): 594-599 (1997).
Gonzalgo, et al., "Rapid quantitation of methylation differences at specific sites using methylation-sensitive single nucleotide primer extension (Ms-SNuPE)", Nucleic Acids Res. 25 (12):2529-2531 (1997).
Gonzalgo, M. et al., "Quantitative methylation anaylsis using methylation sensitive single nucleotide primer extension (Ms-SNuPE)", Methods,27:128-133 (2002).
Goto, "Regulation of X-chromosome inactivation in development in mice and humans", Microbiol. Mol. Biol. Rev. 62, 1998, 362-378.

Hammons, et al., "Specific site methylation in the f'-flanking region of CYP1AS:interindividual differences in human livers", Life Sci 69:839-845 (2001).
Hanada, et al., "bcl-2-gene hypomethylation and high-level expression in B-cell chronic lymphocytic leukemia", Blood. 82 (6):1820-1828 (1993).
Hatch, et al., "Rolling circel amplification of DNA immovilized on solid surfaces and its application to multiplex mutation detection", Genetic Analysis: Biomolecular Engineering, 15, 1999, 35-40.
Hayashizaki, et al., "Restriction landmark genomic scanning method and its various applications", Electrophoresis 14 :251-258 (1993).
Healey, "Development of a Penicillin Biosensor Using a Single Optical Imaging Fiber", SPIE Proc., vol. 2388, 1995, 568-573.
Healey, "Improved Fiber-Optic Chemical Sensor for Penicillin", Analytical Chemistry, vol 67(24), Dec. 15, 1995, 4471-4476.
Healey, B. G. et al., "Fiber Optic DNA Sensory Array Capable of Detecting Point Mutations", Analytical Biochemistry, v. 251., No. 2,, 1997, 270-279.
Heid, et al., "Real time quantitative PCR", Genomic Res 6 (10):986-994 (1996).
Hendrickson, E. R. et al., "High sensitivity multianalyte immunoassay using covalent DNA-labeled anitibodies and polymerase chain reaction", Nucleic Acids Research, vol. 23, No. 3. 1995, pp. 522-529.
Henegariu, "Multiplex PCR: critical parameters and step-by-step protocol", BioTechniques 23(3), 1997, 504-11.
Herman, et al., "Inactivation of the CDKN2/p16/MTS1gene is frequently associated with aberrant DNA methylation in all common human cancers", Cancer Res. 55 (20):4525-30 (1995).
Herman, et al., "Methylation-specific PCR: a novel PCR assay for methylation status of CpG islands", Proc Natl Acad Sci USA 93 (19):9821-9826 (1996).
Hermanson, "Bioconjugate Techniques", San Diego Academic Press, 1996, 640-643.
Hirschfeld, "Laser-Fiber-Optic "Optrode" for Real Time In Vivo Blood Carbon Dioxide Level Monitoring", Journal of Lightwave Technology, vol LT-5(7), 1987, 1027-1033.
Hirschhorn, J N., "SBE Tags: An Array Based Method for Efficient Nucleotide Polymorphisms Genotyping.", PNAS vol. 97 No (22) 2000, 12164-12169.
Hsuih, "Novel, ligation-dependent PCR assay for detection of Hepatitis C Virus in Serum", J. of Clinical Microbiology, vol. 34(3), 1996, 501-507.
Huang, et al., "Methylation profiling of CpG islands in human breast cancer cells.", Hum Mol Genet. 8 (3):459-470 (1999).
Iannone, "Multiplexed Single Nucleotide Polymorphism Genotyping by Oligonucleotide Ligation and Flow Cytometry", Cytometry, vol. 39, vol. 39 No. 2. Feb 2000,, 2000, 131-140.
Illumina, Inc. "Emerging," Windhover's in Vivo, The Business and Medicine Report, Sep. 1998, 2 pages.
Illumina, Inc. "Slide presented by Illumina at Cambridge Healthtech Institute's Implications of Human Genetic Variation—SNP's, Polymorphisms, Diseases & Treatment", Nov. 18-19, 1998, Waltham, Massachusetts, 1998.
IPR2014-01093, "#1 Petition for Inter Partes Review of U.S. Pat. No. 7,955,794", Jul. 2, 2014.
IPR2014-01093,"#10 U.S. Appl. No. 60/234,731, filed Sep. 22, 2000", Sep. 22, 2000.
IPR2014-01093, "#11 Notice of Allowability for U.S. Appl. No. 10/177,727", dated Mar. 21, 2011.
IPR2014-01093, "#2 Corrected Certificate of Service", Jul. 2, 2014.
IPR2014-01093, "#3 Declaration of Xiang-Dong Fu", Jul. 1, 2014.
IPR2014-01093, "#4 Declaration of David C. Ward", Jul. 1, 2014.
IPR2014-01093, "#5 U.S. Appl. No. 60/180,810, filed Feb. 7, 2000", Feb. 7, 2000.
IPR2014-01093, "#6 Declaration Under 37 C.F.R. 1.132 by Jian-Bing Fan, Ph.D.", Oct. 30, 2007.
IPR2014-01093, "#7 Declaration Under 37 C.F.R. 1.132 by Min-Jui Richard Shen, Ph.D.", Oct. 30, 2007.
IPR2014-01093, "#8 U.S. Appl. No. 10/177,727, filed Jun. 20, 2002", Jun. 20, 2002.

(56) References Cited

OTHER PUBLICATIONS

IPR2014-01093, "#9 Selected File History from U.S. Appl. No. 10/177,727", Feb. 23, 2006.
Issa, et al., "Methylation of the oestrogen receptor CpG islands ageing and nepplasia in human colon", Nat Genet. 7 (4) 536-540 (1994).
Jones, et al., "Cancer epigenetics comes of age", Nature Genetics, 21(2), 1999, 163-167.
Jones, D H., "A iterative and regenerative method for DNA sequencing", Biotechniques. vol. 22:939 (1997).
Kawai, et al., "Comparison DNA methylation pattens among cell lines by restriction landmark genomic scanning", Mol Cell Biol.14 (11):7421-7427 (1994)., 1994, 7421-7427.
Khanna, et al., "Mutiplex PCR/LDR for detection of K-ras mutations in primary colon tumors.", Oncogens, 18, 27-38. 1999., 27-38.
Koster, H et al., "A strategy for rapid and efficient DNA sequencing by mass spectrometry", Nature Biotechnology, Sep. 1996, pp. 1123-1128, vol. 14., 1996, 1123-1128.
Kozal, "Extensive polymorphisms observed in HIV-1 clade B protease gene using high-density oligonucleotide arrays", Nature MEd, 2, 1996, 753-759.
Kumar, "Rett and ICF syndromes: methylation moves into medicine", J. Biosci., 25(3), 2000, 213-214.
Kumazaki, T. et al., "Detection of Alternative Splicing of Fibronectin MRNA in a Single Cell", J Cell Sci., (1999); 112(Pt 10):1449-1453.
Kuppuswamy, et al., "Single Nucleotide primer extension to detect genetic diseases: Experimental application to hemophilia B (Factor IX) and cystic fibrosis genes", Proc. Natl. Acad. of Sci USA 88(4) 1143-1147 (1991), 1991, 1143-1147.
Kuzami, et al., "#12 Detection of alternative splicing of fibronectin mRNA in a single cell", J. of Cell Science: 112, 1999, 1449-53.
Ladner, et al., "Multiplex detection of hotspot mutations by rolling circle-enabled universal microarrays.", Lab. Invest:J. Tech. Meth. Path 81:1079-1086 (2001).
Lewin, et al., "The Mystique of Epigenetics", Cell 93:301-303 (1998).
Lizardi, "Mutation detection and single-molecule counting using isothermal rolling-circle amplification", Nature Genetics, vol. 19, 1998, 225-232.
Lockhart, et al., "Genomics, gene expression and DNA arrays", Nature, 405(6788), 2000, 827-836.
Lockhart, D.J. et al., "#14 Expression monitorin by hybridization to high-density oligonucleotide arrays", Nature Biotech, 14, 1996, 1675-80.
Lyamichev, "Polymorphism identification and quantitative detection of genomic DNA by invasive cleavage of oligonucleotide probes", Nature Biotechnology, vol. 17, 1999, 292-296.
Metzker, "Termination of DNA synthesis by novel 3'-modified-deoxyribonucleoside 5'-triphosphases", Nucleic Acids Research, vol. 22(20), 1994, 4259-4267.
Michael, "Fabrication of Micro- and Nanostructures Using Optical Imaging Fibers and Their Use as Chemical Sensors", Proc. 3rd Intl Symp, Microstructures and Microfabricated Systems, 1997, 152-157.
Michael, "Making Sensors out of Disarray: Optical Sensor Microarrays", Proc. SPIE, vol. 3270, 1998, 34-41.
Michael, "Randomly Ordered Addressable High-Density Optical Sensor Arrays", Analytical Chemistry, vol. 70(7), 1998, 1242-1248.
Mignani(Grazia), "In-Vivo Biomedical Monitoring by Fiber-Optic Systems", Journal of Lightwave Technology, vol. 13(7), 1995, 1396-1406.
Myer, et al., "Synthesis and application of circularizable ligation probes", BioTechniques, 30, 2001, 584-593.
New England Biolabs, "Exonuciease I (*E. coli*)", Document for Hpa II from NEB. Printed on Sep. 8, 2010, 2.
New England Biolabs, "HpaI I", Documents for exonuclease I and Msp I from NEB Printed on Sep. 9, 2010, 5.

Newton, et al., "Analysis of any point mutation in DNA. The amplification refractory mutation system (ARMS)", Nucleic Acid Research, 17, 1989, 2503-2516.
Newton, "PCR Essential Data", J.W. Wiley & Sons, New York, 1995.
Nickerson, "Gene probe assays and their detection", Current Opinion in Biotechnology, 4, 1993, 48-51.
Nikiforov, et al., "Genetic Bit Analysis: a solid phase method for typing single nucleotide polymorphisms", Nucleic Acids Research, 22(20), 1994, 4167-4175.
Nilsson, et al., "Padlock probes: circularizing oligonucleotides for localized DNA detection", Science, 265, 1994, 2085-2088.
Oakeley, "DNA methylation analysis: A review of current methodologies.", Pharm Thera 84: 389-400 (1999).
Otterson, et al., "CDKN2 gene silencing in lung cancer by DNA hypermethylation and kinetics of p16INK4 protein induction by 5-aza 2'deoxycytidine", Oncogene 11(6):1211-6 (1995), 1995, 1211-1216.
Pantano, "Ordered Nanowell Arrays", Chem Mater, vol. 8(12), 1996, 2832-2835.
Pease, et al., "Light-generated oligonucleotide array for rapid DNA sequence analysis", Proc. Natl. Acad. Sci., vol. 91, Issue 11, 1994, 5502-5026.
Peterson, et al., "Fiber-Optic Sensors for Biomedical Applications", Science., vol. 13., (1984)., Apr. 1984, 123-127.
Peterson, J I. et al., "Fiber Optic pH Probe for Physiological Use.", Analytical Chemistry., v52.,No. 6. May 1980, 864-869.
Piunno, "Fiber-Optic DNA Sensor for Fluorometric Nucleic Acid Determination", Analytical Chemistry, vol. 67. No (15), Aug. 1995, 2635-2643.
Pope, "Fiber Optic Chemical Microsensors Employing Optically Active Silica Microspheres", SPIE, 2388, 1995, 245-256.
Prezant, Toni and, Fischel-Ghodsian, Nathan, "Trapped oligonucleotide nucleotide incorporation (TONI) assay, a simple methoed for screening point mutations,.", Hum. Mutat. 1 (2):159-164 (1992).
Ranki, et al., "Sandwich hybridization as a convenient method for the detection of nucleic acids in crude samples", Gene, 21, 1983, 77-85.
Razin, et al., "CpG methylation, chromatin structure and gene silencing—A three-way connection", Embo J., 17(17), 1998, 4905-4908.
Razin, et al., "DNA Methylation and embryogenesis", DNA Methylation: Molecular Biology and Biological Significance, 1993, 343-357.
Reik, et al., "Epigenetic reprogramming in mammalian development", Science, 293, 2001, 1089-1093.
Rein, et al., "Identifying 5-methylcytosine and related modifications in DNA genomes", Nucleic Acids Res. 26 (10):2255-2264 (1998).
Ronaghi, M et al., "A Sequencing Method Based on Real-Time Phyrophosphate", Science. Jul. 17, 1998; 281 (5375):363-365.
Roth, et al., "Biotin-avidin microplate assay for the quantitative analysis of enzymatic methylation of DNA by DNA methyltransferase.", Biol. Chem., Mar. 2000, vol. 381, p. 269-272.
Roth, et al., "Bringing out the best features of expression data", Genome Research, 11(11), 2001, 1801-1802.
Sambrook, et al., "Molecular Cloning: A Laboratory Manual", 3rd Edition, Cold Spring Harbor Laboratory, New York, 2001.
Sasaki, et al., "DNA methylation and genomic imprinting in mammals", Exs. 64, 1993, 469-486.
Schafer, et al., "DNA variation and the future of human genetics", Nature Biotechnology, 16, 1998, 33-39.
Schulz, "DNA methylation in urological malignancies (review)", Int. J. Oncol. 13, 1998, 151-167.
Sehgal, et al., "#22 Application of the differential hybridization of Atlas Human expression arrays technique in the identification of differentially expressed genes in human gliobllastoma multiforme tumor tissue", J. Surg. Oncol., 67, 1998, 234-41.
Seradyn, "Sera-Mag Streptavadin Magnetic Microparticles", Particle Technology, Nov. 1996, 1-7.
Sheldon, et al., "C-reactive protein and its cytokine mediators in intensive-care patients", Clin. Chem., 39, 1993, 147-150.

(56) References Cited

OTHER PUBLICATIONS

Shoemaker, "Quantitative phenotypic analysis of yeast deletion mutants using a highly parallel molecular bar-coding strategy", Nature Genetics, 14, vol. 14. No. 4. (Dec. 1996), 450-456.
Shuber, Anthony P. et al., "High throughput parallel analysis of hundreds of patient samples for more than 100 mutations in multiple disease genes", Human Molecular Genetics, vol. 6 (3), 337-347.
Singer-Sam, Judith et al., "A quantitative HpaII-PCR assay to measure methylation of DNA from a small number of cell.", Nucleic Acids Res. 18(3):687 (1990), 1990, 687.
Smiraglia, et al., "A new tool for the rapid cloning of amplified and hypermethylated human DNA sequences from restriction landmark genome scanning gels", Genomics 58 (3):254-262 (1999).
Smith, et al., "Fluorescence detection in automated DNA sequence analysis", Nature, 321, 1986, 674-679.
Sooknanan, et al., "Nucleic Acid Sequence-Based Amplification", Molecular Methods for Virus Detection, Academic Press, Ch. 12, 1995, 261-285.
Sooknanan, et al., "Profiting from Gene-based Diagnostics", CTB International Publishing, N.J., 1996.
Southern, E. M. "#21 Detection of specific sequences among DNA fragments separated by gel electrophoresis", J. Mol. Bio., 98(3), 1975, 503-17.
Strachan, "A Rapid General Method for the IDentification of PCR Products Using a Fibre-Optic Biosensor and its Application to the Detection of Listeria", Letters in Applied Microbiology, 21, vol. 21. No. 1 (Jul. 1995)., 1995, 5-9.
Syvanen, Ann-Christine, "From gels to chips: 'Minisequencing' Primer Extension for Analysis of Point Mutations and Single Nucleotide Polymorphisms", Human Mutation, 13, 1999, 1-10.
Taylor, et al., "The diagnostic significance of Myf-3 hypermethylation in malignant limphoproliferative disorders", Leukemia 15(4):583-589 (2001).
Thomas, et al., "Amplification of padlock probes for DNA diagnostics by cascade rolling circle amplification or the polymerase chain reaction", Arch. Pathol. Lab. Med., 123, 1999, 1170-1176.
Tijssen, "Overview of principles of hybridization and the strategy of nucleic acid assays", Techniques in Biochemistry and Molecular Biology-Hybridization withy Nucleic Acid Probes, 1993.
Torres, et al., "#23 Differentiation of *Neisseria gonorrhoeae* from other Neisseria species by use of the restriction endonuclease HaeIII", J. of Clin. Microbiology, 20(4), 1984, 687-90.
Toyota, et al., "Identification of differentially methylated sequences in colorectal cancer by methylated CpG island amplification", Cancer Res. 59 (10):2307-2312 (1999).
Trinh, et al., "DNA Methylation Analysis by MethyLight Technology", Methods, 25, 2001, 456-462.
Ugozzoli, Luis, "Detection of Specific Alleles by Using Allele-Specific Primer Extension Followed by Capture on Solid Support", GATA 9(4), 1992, 107-112.
Venton, "Screening combinatorial libraries", Chemometrics and Intelligent Laboratory Systems, NL, Elsevier Science Publishers, Amsterdam, 48(2), 1999, 131-150.
Wallace, et al., "Hybridization of synthetid oligodeoxyribonucleotides to phi chi 174 DNA: the effect of single base pair mismatch", NAR, 6, 1979, 3543-3547.
Walt, "Fiber-Optic Imaging Sensors", Accounts of Chemical Research, 31(5), 1998, 267-278.
Walt, "Fiber-Optic Sensors for Continuous Clinical Monitoring", Proc. IEEE, 80(6), 1992, 903-911.
Walt, D., "Bead Based Fiber-Optic Arrays", Science. 287 :451-452 (1999), 451-452.
Wang, et al., "#13 Large-scale identification,mapping an genotyping of single nucleotide polymorphisms in human genome", Science:280, 1998, 1077-82.
Whitcombe, D., "Detection of PCR products using self-probing amplicons with fluorescence", Nature Biotechnology, Aug. 1999, p. 804-807, vol. 17.
Xu, et al., "High sequence fidelity in a non-enzymatic DNA autoligation reaction", NAR, 27, 1999, 875-881.
Yan, et al., "CpG island Arrays: An application toward deciphering epigenetic signatures of breast cancer", Clin. Cancer Res. 6:1432-1438 (2000).
Yan, et al., "Role of DNA methylation and histone acetylation in steroid receptor expression in breast cancer", J. Mammary Gland Biol. Neoplasia, 6(2), 2001, 183-192.
Yeakley, et al., "Profiling alternative splicing on fiber-optic arrays", Nature, 20, 2002, 353-358.
Zhong, et al., "A survey of Fraxe allele sizes in three populations", Am. J. Med. Genet., 64(2), 1996, 415-419.
Declaration Under 37 C.F.R. §1.132 by Jiang-Bing Fan of Oct. 30, 2007 filed in U.S. Appl. No. 10/177,727; pp. 32.
Declaration Under 37 C.F.R. §1.132 by Min-Jui Richard Shen of Oct. 30, 2007 filed in U.S. Appl. No. 10/177,727; pp. 16.
Declaration of Xiang-Dong Fu of Jul. 1, 2014 filed in Inter Partes Review of U.S. Pat. No. 7,955,794, filed Jul. 2, 2014; pp. 101.
Declaration of David Ward of Jul. 1, 2014 filed in Inter Partes Review of U.S. Pat. No. 7,955,794, filed Jul. 2, 2014 with the U.S. PTAB; pp. 147.
U.S. Appl. No. 60/180,810, filed Feb. 7, 2000; pp. 50.
U.S. Appl. No. 60/234,731, filed Sep. 22, 2000; pp. 57.
U.S. Appl. No. 10/177,727 as filed Jun. 20, 2002; pp. 102.
U.S. Office Actions and Applicant Responses during prosecution of U.S. Appl. No. 10/177,727, filed Jun. 20, 2002 and issued Jun. 7, 2011; pp. 72.
U.S. Notice of Allowance dated Apr. 4, 2011 for U.S. Appl. No. 10/177,727, filed Jun. 20, 2002.

\* cited by examiner

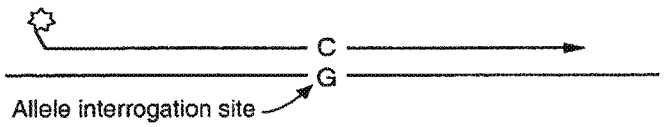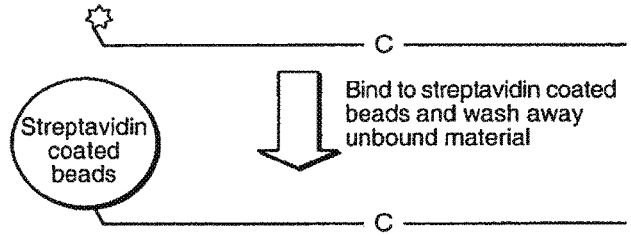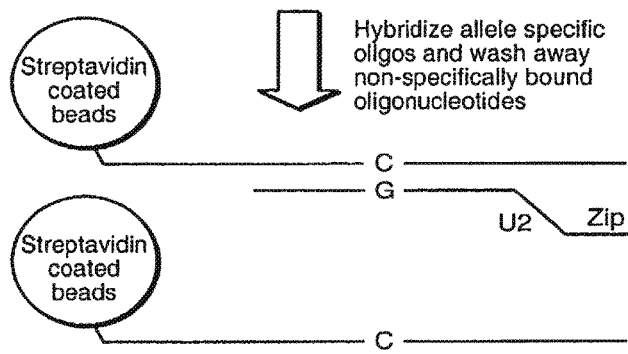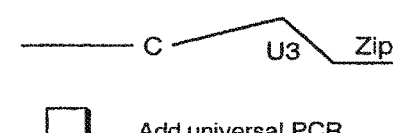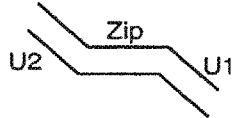
FIG. 4

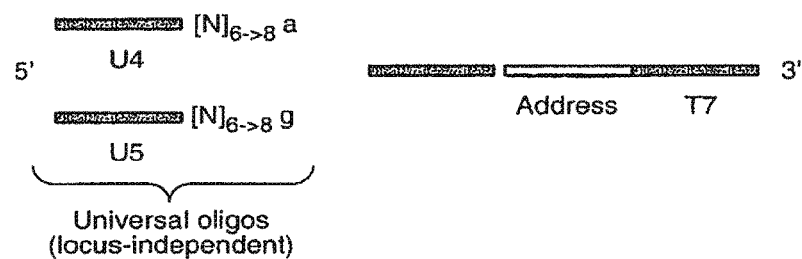
FIG._9
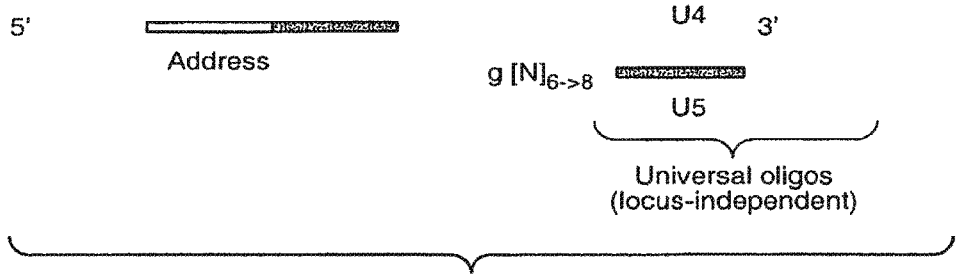
FIG. 10

MULTIPLEX NUCLEIC ACID REACTIONS

This application is a continuation of U.S. application Ser. No. 13/604,872 filed on Sep. 6, 2012, now U.S. Pat. No. 8,906,626 which is a continuation of U.S. application Ser. No. 12/790,757, filed on May 28, 2010, now U.S. Pat. No. 8,288,103, which is a continuation of U.S. application Ser. No. 12/507,022, filed on Jul. 21, 2009, now abandoned, which is a continuation of U.S. application Ser. No. 10/194,958, filed on Jul. 12, 2002, now U.S. Pat. No. 7,582,420, which is a continuation-in-part of U.S. application Ser. No. 10/177,727, filed Jun. 20, 2002, now U.S. Pat. No. 7,955,794, which claims the benefit of priority to U.S. Provisional Application Nos. 60/305,118, filed Jul. 12, 2001, 60/311,271, filed Aug. 9, 2001, 60/336,958, filed Dec. 3, 2001 and 60/341,827, filed Dec. 17, 2001, and is a continuation-in-part of each of the following: U.S. application Ser. No. 09/779,376, filed Feb. 7, 2001, now abandoned, which claims the benefit of priority to U.S. Provisional Application Ser. No. 60/180,810, filed Feb. 7, 2000 and 60/234,732, filed Sep. 22, 2000; U.S. application Ser. No. 09/915,231, filed Jul. 24, 2001, now U.S. Pat. No. 6,890,741, which claims the benefit of priority to U.S. Provisional Application Ser. No. 60/234,143, filed Sep. 21, 2000 and 60/297,609, filed on Jun. 11, 2001 and is a continuation-in-part of U.S. application Ser. No. 09/779,376, filed Feb. 7, 2001, now abandoned, which claims the benefit of priority to U.S. Provisional Application Ser. No. 60/180,810, filed Feb. 7, 2000 and 60/234,732, filed Sep. 22, 2000; and U.S. application Ser. No. 09/931,285, filed Aug. 16, 2001, now U.S. Pat. No. 6,913,884, each of which is expressly incorporated herein by reference in its entirety.

Portions of this invention were made with Government support under NIH Grant numbers HG02003 and CA81952 awarded by the PHS. The Government has certain rights in the invention.

FIELD OF THE INVENTION

The invention is directed to a variety of multiplexing methods used to amplify and/or genotype a variety of samples simultaneously.

BACKGROUND OF THE INVENTION

The detection of specific nucleic acids is an important tool for diagnostic medicine and molecular biology research. Gene probe assays currently play roles in identifying infectious organisms such as bacteria and viruses, in probing the expression of normal genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48-51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis as outlined below (for a review, see Abramson et al., Current Opinion in Biotechnology, 4:41-47 (1993)).

Currently, a variety of biochips comprising substrates with associated nucleic acids are used in a variety of nucleic acid detection systems, including the detection, quantification, sequence determination and genotyping of a nucleic acid target sequences. However, sample preparation for these high density chips remains an issue.

Accordingly, it is an object of the invention to provide a number of methods directed to the multiplexing amplification and/or genotyping reactions of target sequences to create amplicons that can subsequently be detected on an array.

SUMMARY OF THE INVENTION

In accordance with the objects outlined above, the present invention provides a method of detecting target sequences in a sample comprising providing a first solid support comprising at least a first and a second target sequence, contacting the first and second target sequences with first and second probes, respectively, wherein each of the first and second probes comprise a first universal priming site, a target specific domain substantially complementary to at least a portion of the target sequence, to form first and second hybridization complexes, respectively, removing unhybridized probes, contacting the first and second hybridization complexes with a first enzyme to form modified first and second probes, respectively contacting the modified first and second probes with at least a first primer that hybridizes to the universal priming site NTPs, and an extension enzyme, wherein the first and second modified probes are amplified to form first and second amplicons, respectively, and detecting the amplicons.

In addition the invention provides a method of detecting target sequences in a sample comprising providing a first solid support comprising at least a first and a second target sequence, contacting the first and second target sequences with first and second probes, respectively, wherein each of the first and second probes comprise a first universal priming site, a target specific domain substantially complementary to at least a portion of the target sequence, to form first and second hybridization complexes, respectively, removing unhybridized probes, contacting the first and second probes with at least a first universal primer that hybridizes to the universal priming site, NTPs and an extension enzyme, wherein the first and second probes are extended to form first and second modified probes, respectively, contacting the first and second modified probes with at least third and fourth probes, respectively, wherein the modified first and second probes comprise a detection position, the third and fourth probes each comprise an interrogation position, and a second enzyme, wherein the second enzyme only modifies the third and fourth probes if there is perfect complementarity between the bases at the interrogation position and the detection position, forming third and fourth modified probes, and detecting the third and fourth modified probes.

In addition the invention provides a method comprising providing a plurality of target nucleic acid sequences each comprising from 3' to 5' a first, second and third target domain, the first target domain comprising a detection position, the second target domain being at least one nucleotide contacting the target nucleic acid sequences with sets of probes for each target sequence, each set comprising a first probe comprising from 5' to 3' a first domain comprising a first universal priming sequence, and a second domain comprising a sequence substantially complementary to the first target domain of a target sequence, and an interrogation position within the 3' four terminal bases, a second probe comprising a first domain comprising a sequence substantially complementary to the third target domain of a target sequence, to form a set of first hybridization complexes, contacting the first hybridization complexes with an extension enzyme and dNTPs, under conditions whereby if the base at the interrogation positions is perfectly complementary with the bases at the detection positions, extension of the first probes occurs through the second target domains to form second hybridization complexes, contacting the second hybridization complexes with a ligase to ligate the extended first probes to the second probes to form amplification templates.

In addition the invention provides a multiplex reaction method comprising providing a sample comprising at least first and second targets hybridizing the first and second targets with first and second probes, respectively forming first and second hybridization complexes, respectively, immobilizing the first and second hybridization complexes, washing to remove unhybridized nucleic acids, contacting the first and second hybridization complexes with an enzyme, whereby the first and second probes are modified forming modified first and second probes, respectively, whereby the modified first and second probes are modified to contain first and second interrogation nucleotides that are complementary to first and second detection nucleotides in the first and second targets, respectively, contacting the modified first and second probes with first and second allele specific primers, respectively, whereby the first and second allele specific primers hybridize to the modified first and second probes, respectively, 5' to the first and second interrogation nucleotides, dNTPs, polymerase, whereby the first and second allele specific primers are modified when a target domain of the allele specific primers is perfectly complementary to the modified target probes to form modified first and second allele specific probes, amplifying the modified first and second allele specific probes to form first and second amplicons, and detecting the first and second amplicons.

In addition the invention provides a method comprising providing a plurality of target nucleic acid sequences each comprising from 3' to 5' a first, second and third target domain, the first target domain comprising a detection position, the second target domain being at least one nucleotide, contacting the target nucleic acid sequences with sets of probes for each target sequence, each set comprising: a first probe comprising from 5' to 3', a first domain comprising a first universal priming sequence, and a second domain comprising a sequence substantially complementary to the first target domain of a target sequence, and an interrogation position within the 3' four terminal bases, a second probe comprising a first domain comprising a sequence substantially complementary to the third target domain of a target sequence, to form a set of first hybridization complexes, contacting the first hybridization complexes with at least a first universal primer that hybridize to the first universal priming sequence, an extension enzyme and dNTPs, under conditions whereby if the base at the interrogation positions are perfectly complementary with the bases at the detection positions, extension of the first probes occurs through the second target domains to form second hybridization complexes, contacting the second hybridization complexes with a ligase to ligate the extended first probes to the second probes to form amplification templates.

Tagged locus specific primers are annealed to the genomic DNA and washed. DNA polymerase (Taq DNA polymerase), dNTPs, ddNTPs and buffer is added to the hybridized primers. The DNA polymerase will extend the locus specific primers that have hybridized and are matched exactly at the 3' end to DNA. In this first primer extension reaction, the primer extended product has captured the locus allele information and also adjacent DNA sequence information. The primer extension products are eluted away from the genomic DNA. The eluted primer extension products are captured onto another set of streptavidin coated beads through the biotin molecule on the locus specific primer. This capture process purifies the primer extension product and reduces the complexity of DNA going into the second hybridization and extension process. The second capture process may improve the multiplexability of this assay through the reduction of complexity.

Allele specific primers for each interrogated locus are added to the captured DNA and a second hybridization and wash is performed (at high stringency). DNA polymerase (Taq DNA polymerase), dNTPs, and buffer are added to the hybridized primers. An extension reaction is carried out. The extended products are eluted and used in a PCR amplification reaction (using the universal PCR primers specific for these oligos U1, U2 and U3). U2 and U3 are labeled with different fluorescent tags. The ratio in the amount of one allele relative to another is determined by the ratio of the fluorescent tags.

Figure 3:
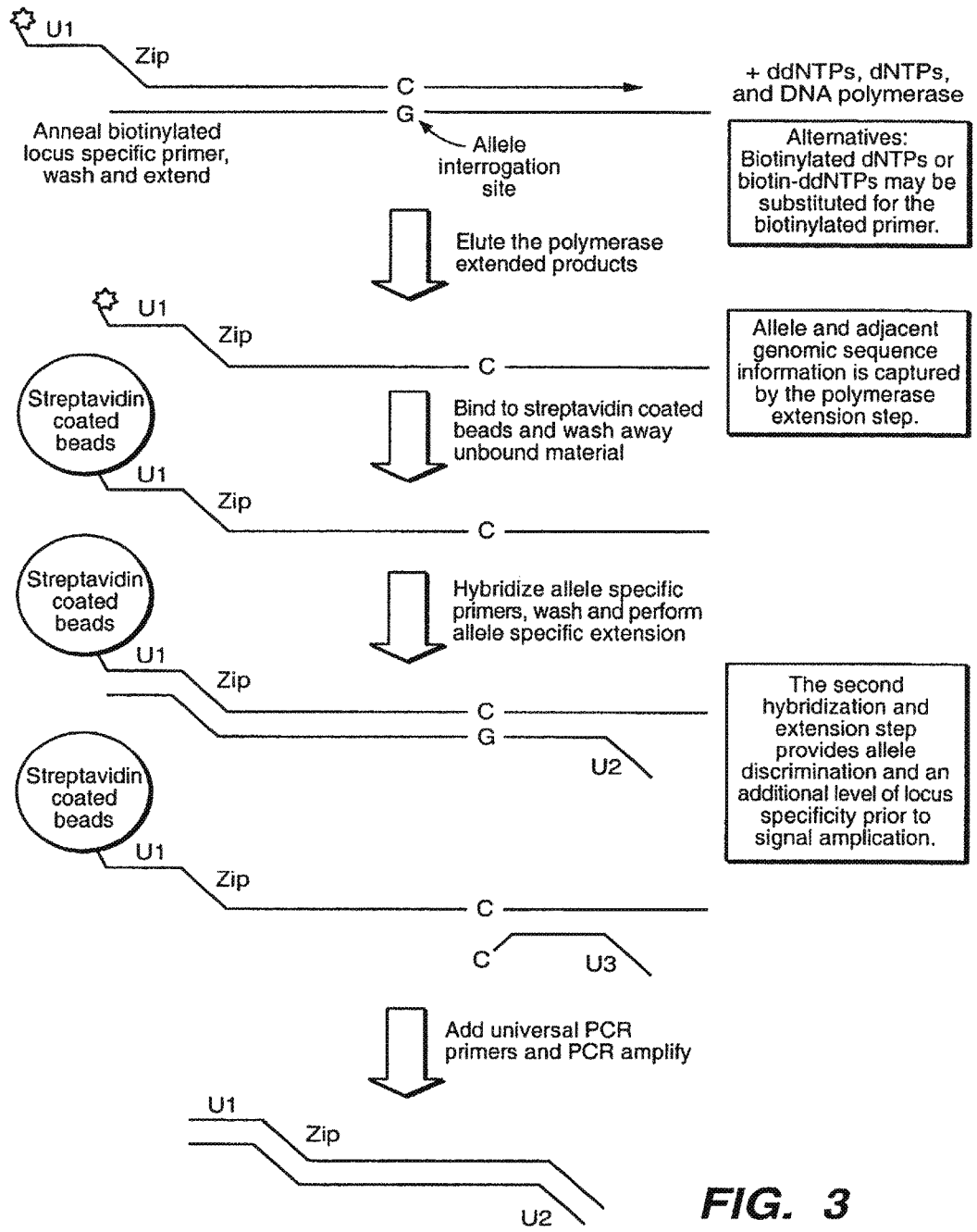
FIG. 3 depicts a preferred method for complexity reduction and allele selectivity. The locus specific primer hybridizes upstream of the interrogation site. It does not have to be directly adjacent to the interrogation site. The locus specific primer also contains an adapter sequence and universal PCR primer hybridization site. The allele specific primers are designed to the opposite strand of DNA (see diagram) and the 3' ends of the primers correspond to the alleles that are interrogated. The 5' ends of the allele specific primers are hybridization sites for universal PCR primers.

FIG. 4 depicts an alternative embodiment of the method outlined in FIG. 3. An allele specific hybridization approach for allele determination may be used in conjunction with the first hybridization, wash and extension. In this process, the locus specific primer is hybridized, washed and extended as above. The locus specific primer does not contain adapter sequences or universal primer sequences. The allele specific oligonucleotide contains the universal PCR primer sequences. Allele specific oligonucleotides are added to the extended products, hybridized and washed under stringent conditions. Allele specifically hybridized sequences are retained and later eluted for a PCR reaction.

Figure 5:
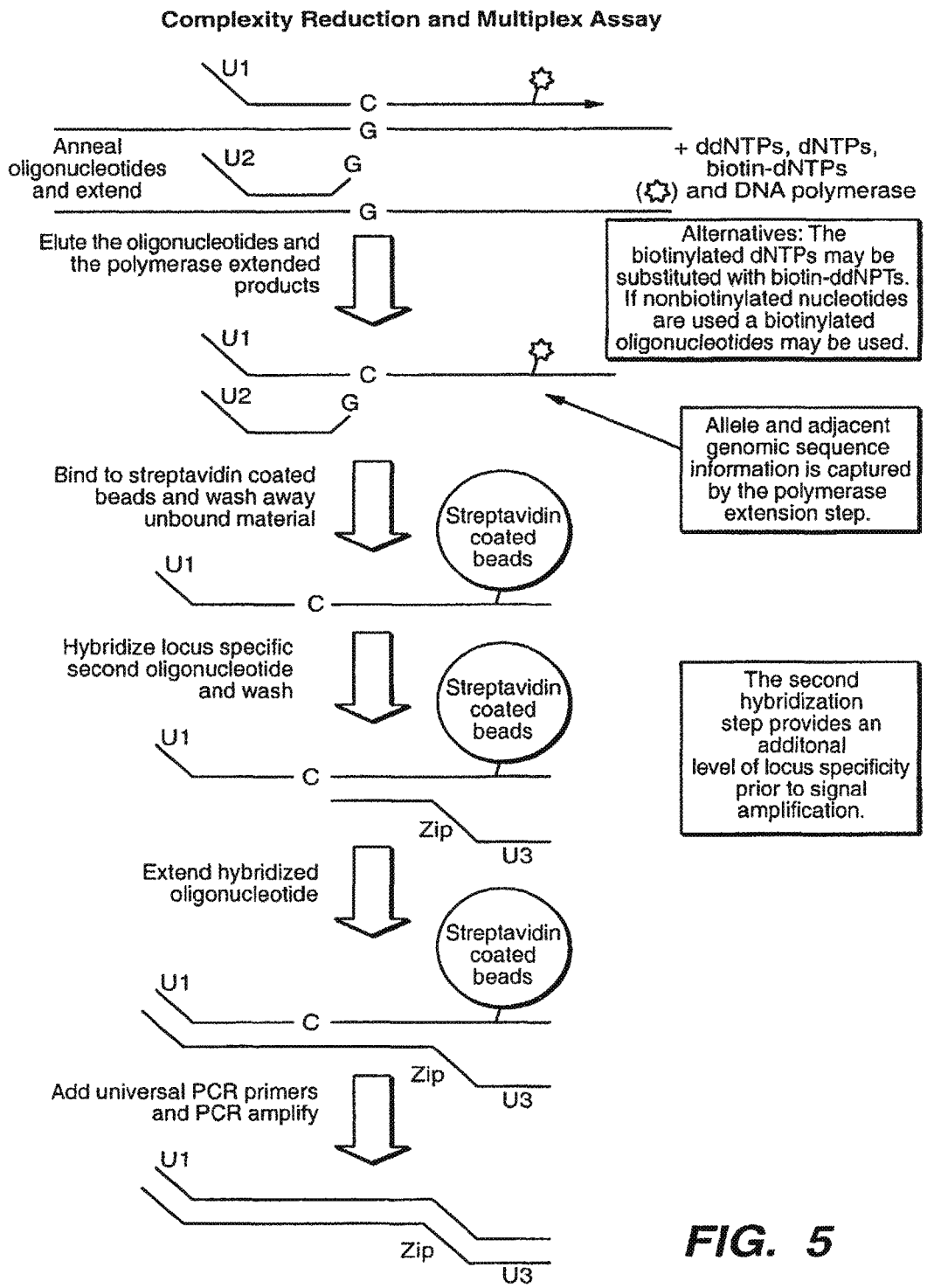

FIG. 5 depicts an alternative embodiment of the method outlined in FIG. 3. In this embodiment allele specific extension is followed by locus specific extension.

Figure 6:
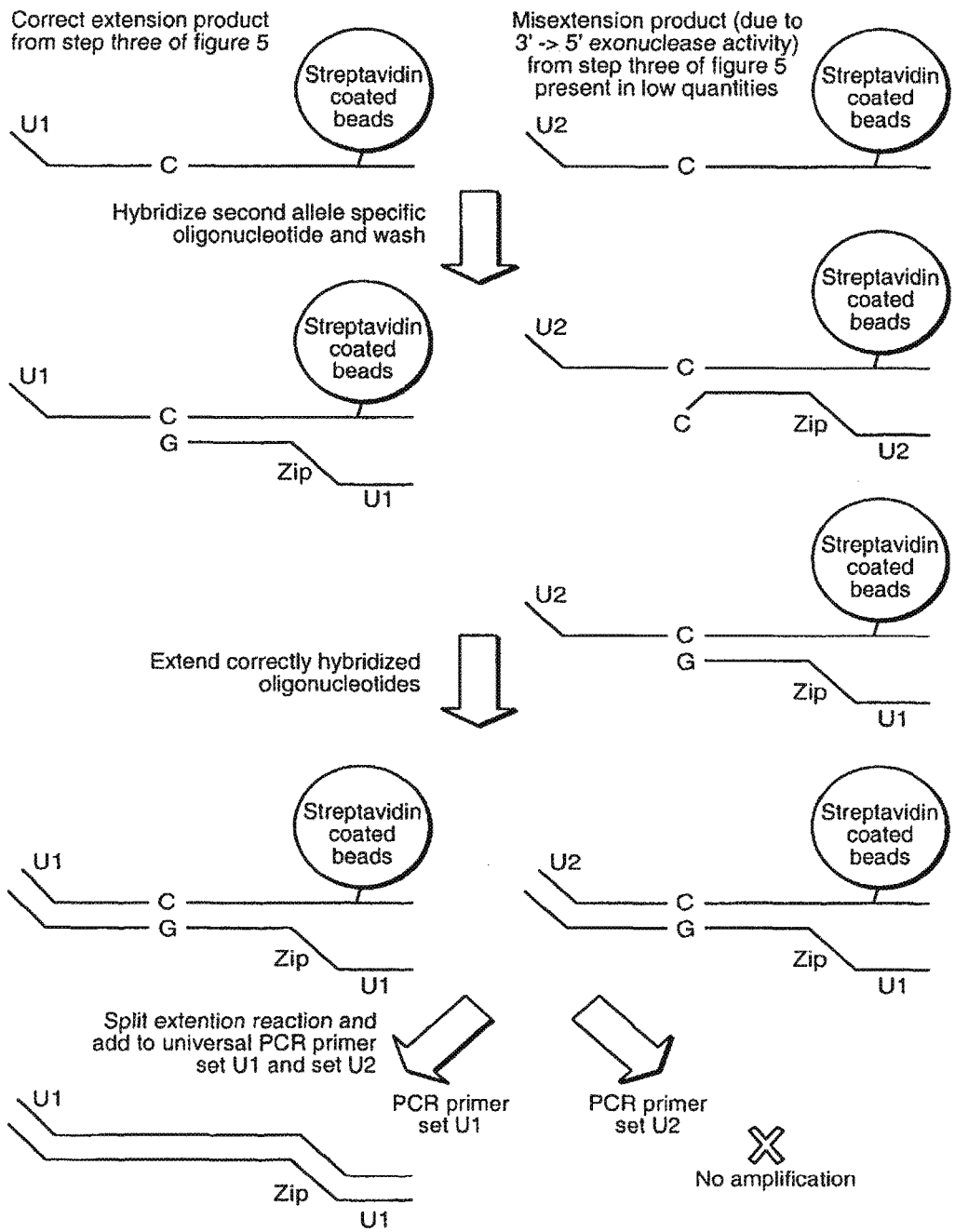

FIG. 6 depicts an alternative embodiment of the method outlined in FIG. 3. A second level of allele specificity along with locus specificity may be obtained by using allele specific extension primers in the second extension step of FIG. 5. Using allele specific extension primers (on alternate strands) in both extension steps would protect against any 3' to 5' exonuclease activity acting in the first allele specific extension step. The extension products from this approach would be placed into two separate PCR reactions containing universal PCR primers specific for each allele set. Misextensions due to exonuclease activity in the first or second extension steps would not be amplified.

Figure 7:
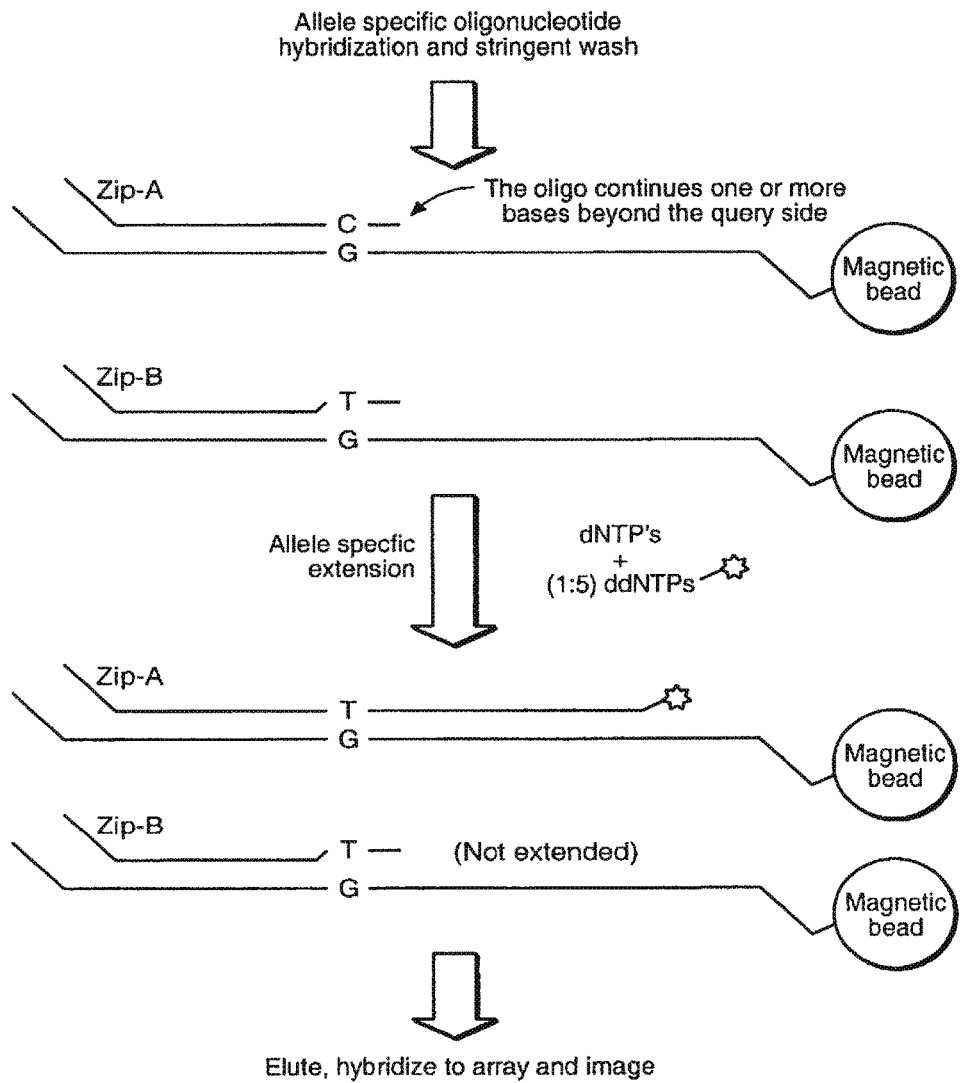

FIG. 7 depicts a preferred method of solid-phase allele-specific primer extension genotyping. For each locus, two allele specific oligonucleotides are designed with each allele represented by a unique adapter. The 3' end of the allele specific oligonucleotides extend one or more bases beyond the query site. The oligonucleotides are hybridized to the template on solid phase under stringent conditions. The solid phase is washed to remove improperly hybridized oligonucleotides. The resulting complex is then extended by a polymerase in an allele specific manner. That is a mismatch at the query site will prevent efficient extension.

Figure 8:
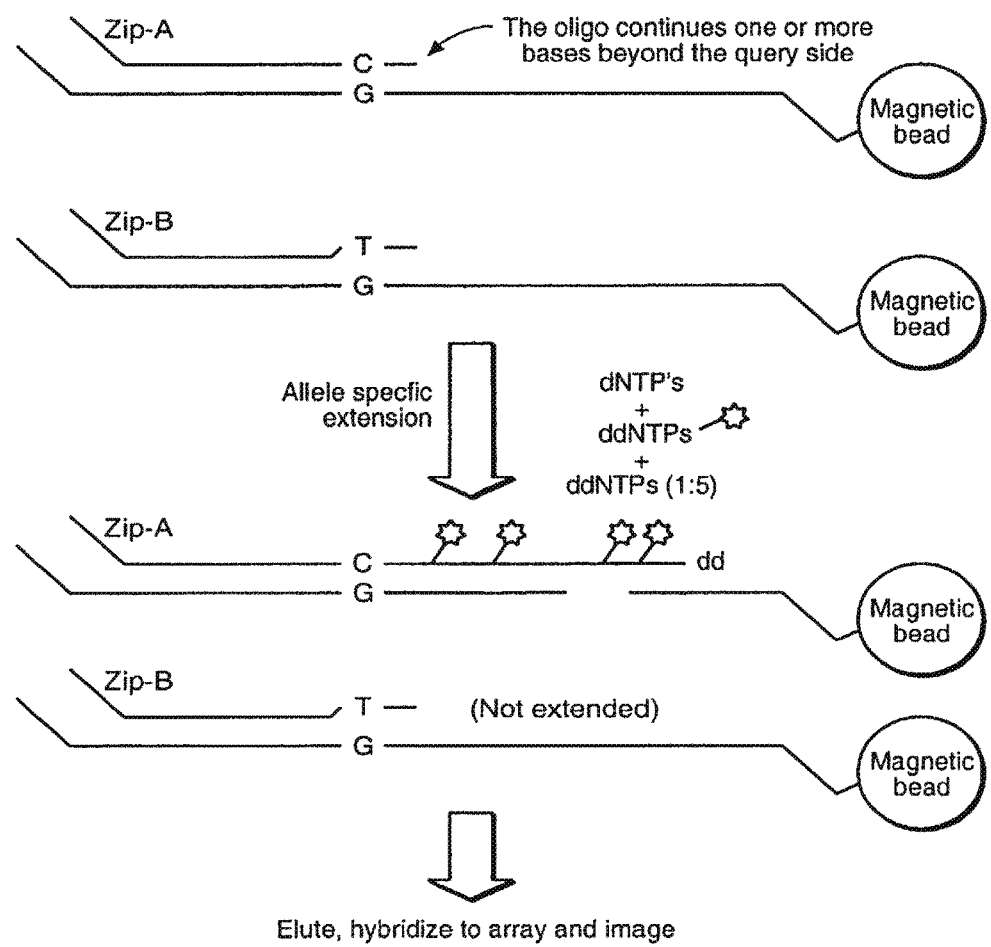

FIG. 8 depicts an alternative method of labeling as compared to FIG. 7.

FIG. 9 depicts a schematic of universal allele specific oligonucleotides.

FIG. 10 depicts a method using the universal allele specific oligonucleotides described in FIG. 9. In this case, since extension must occur from 5' to 3', the U4 and U5 sequences are shown at the 3' end of the template, associated with the allele-selective bases.

Figure 11:
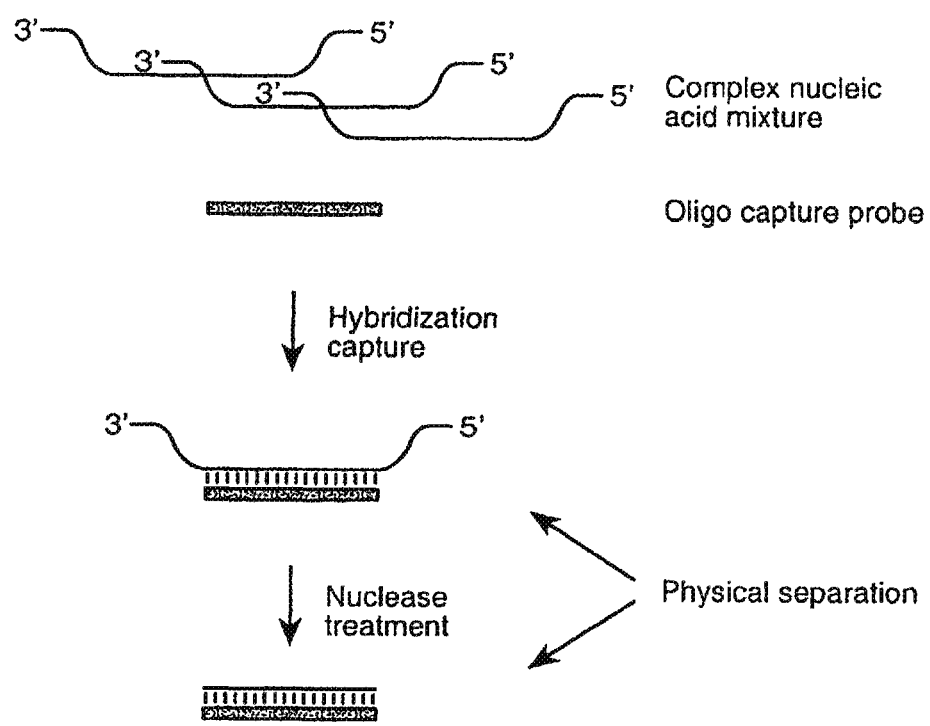

FIG. 11 depicts a method of removing non-hybridized nucleic acids by nuclease treatment. That is, the complexity of a nucleic acid sample is initially reduced by hybridization capture with gene specific oligonucleotides. Excess nucleic acid sequences are removed by a single stranded nuclease.

Figure 12A:
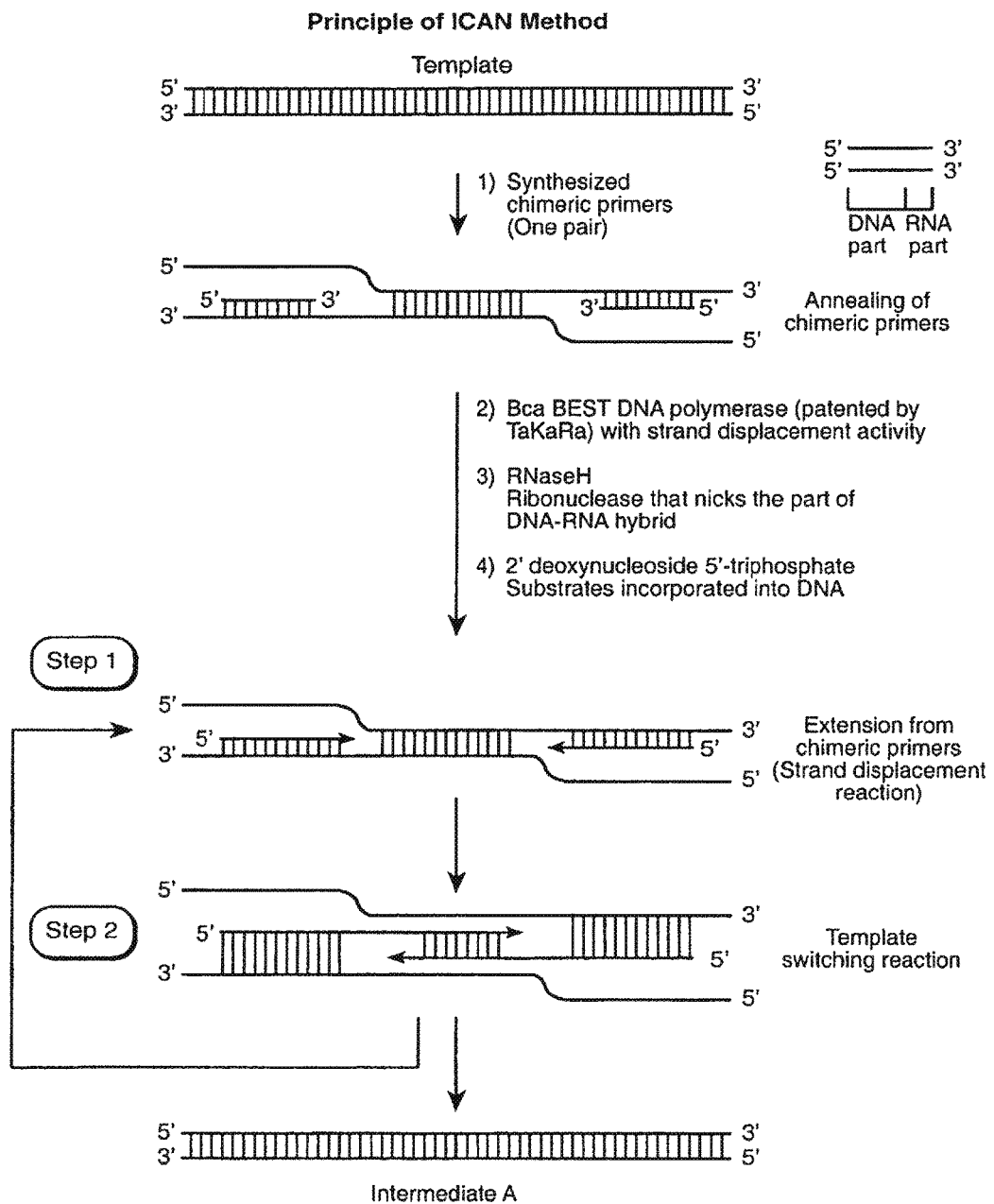
Figure 12B:
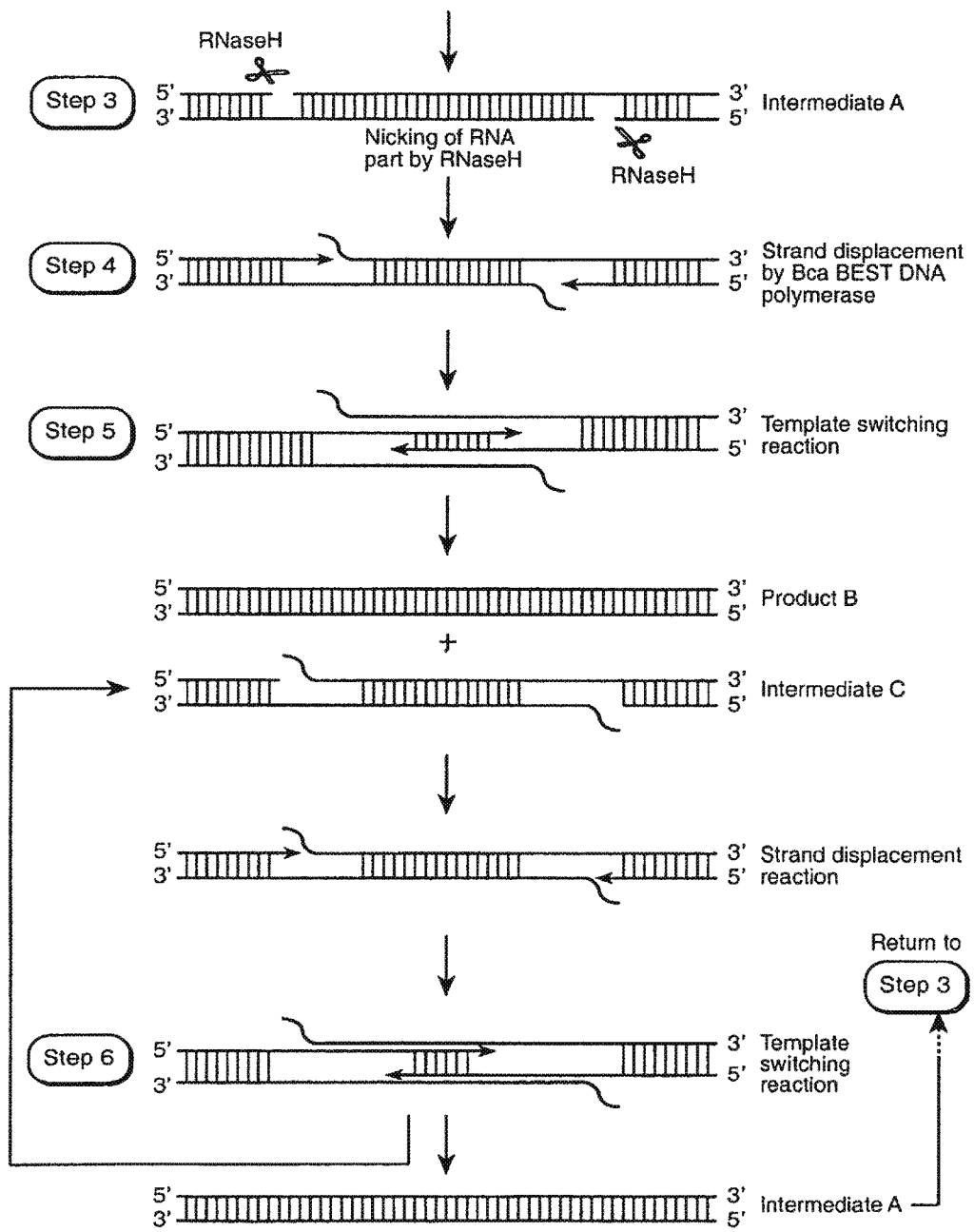

FIGS. 12A and 12B depict the ICAN amplification scheme.

Figure 13A:
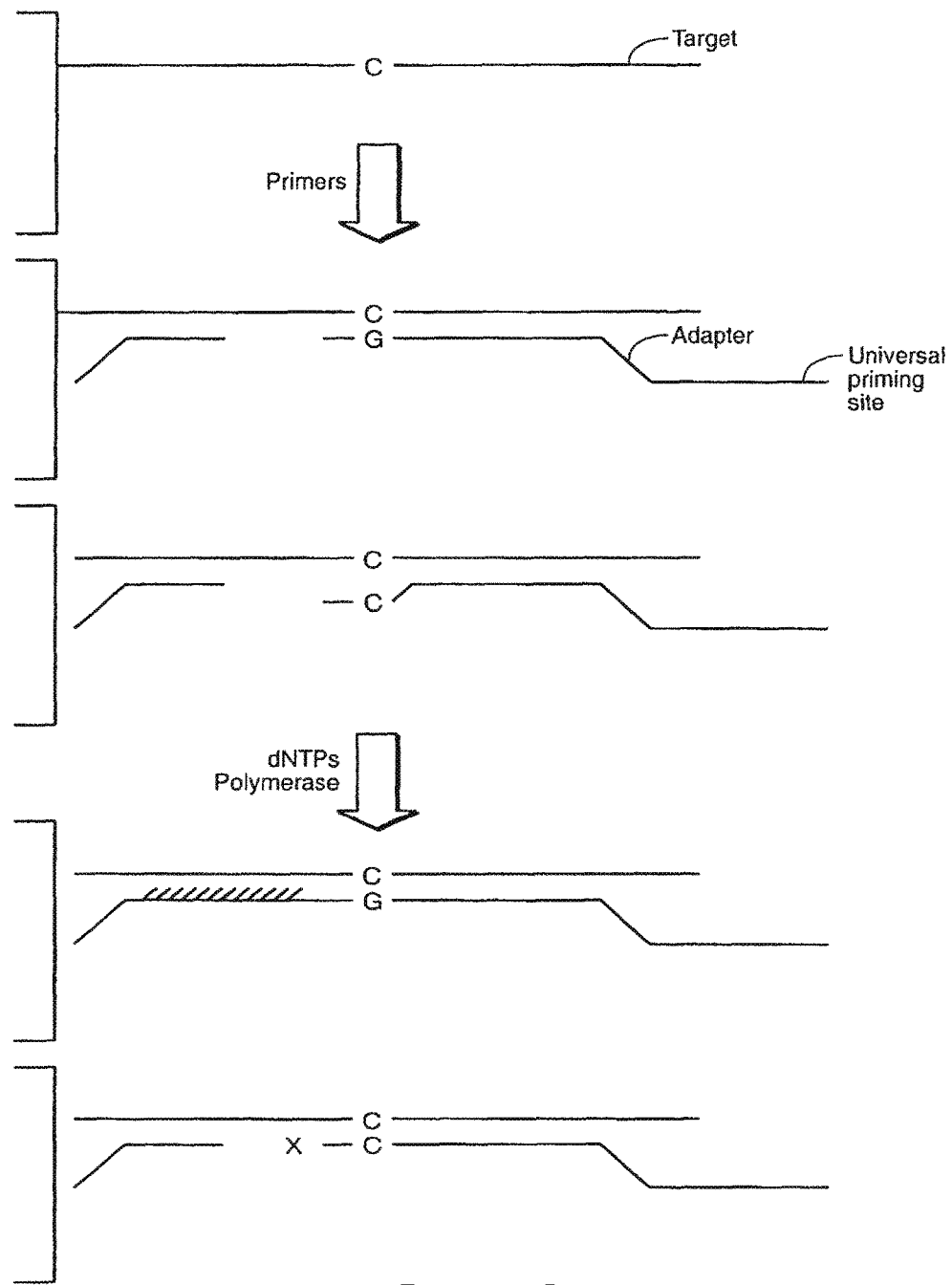
Figure 13B:
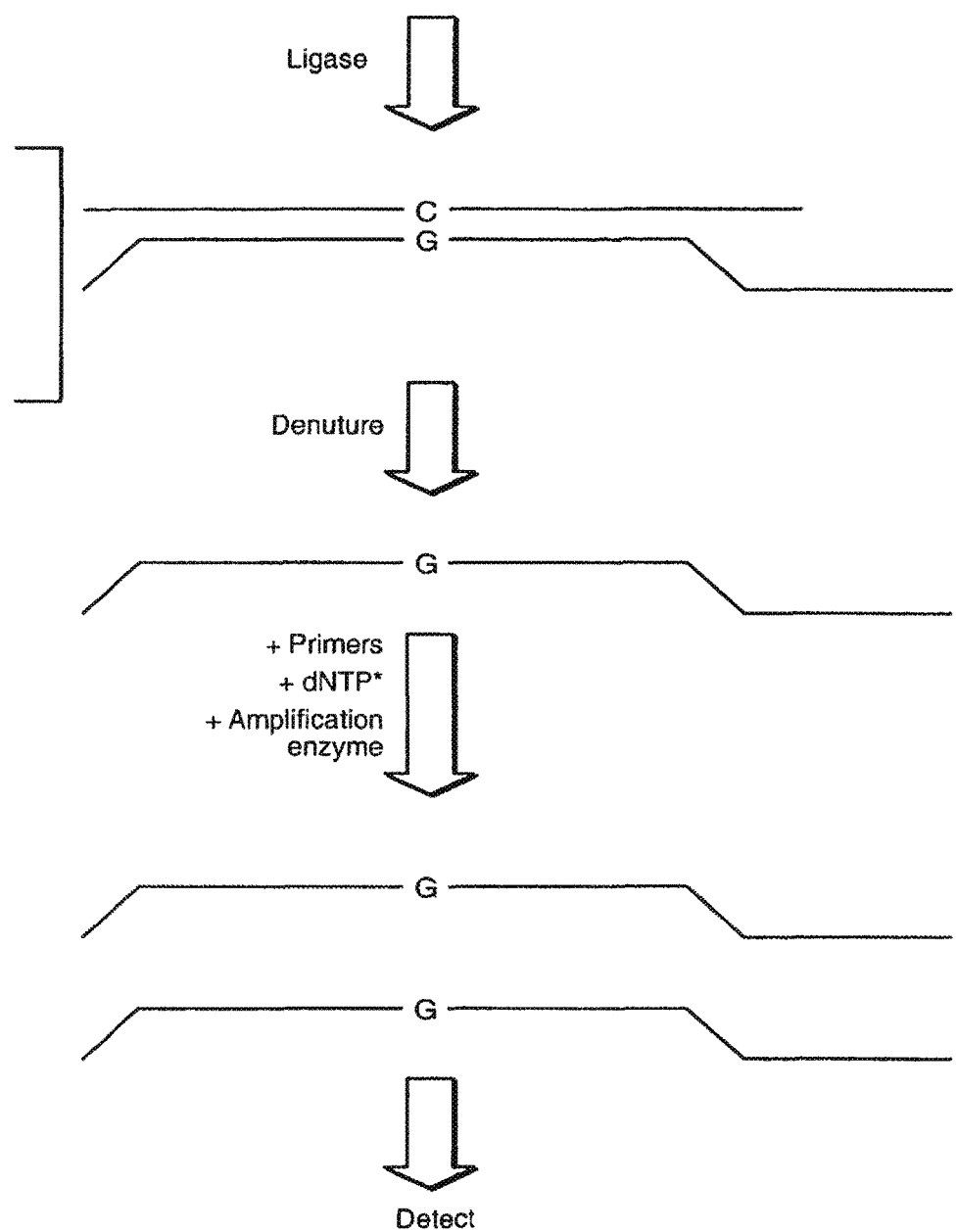

FIGS. 13A and 13B depict a preferred multiplex scheme. Two primers hybridize to a target nucleic acid. The primers include target specific portions and universal priming sites. In addition, one of the primers, preferably the upstream primer, includes an allele specific sequence and an adapter sequence that is specific for the particular allele specific sequence. The primers do not hybridize contiguously on the target. Following hybridization the primer is extended with dNTPs and a polymerase. Following primer extension, the upstream and downstream primers are ligated. The ligated product is then amplified with universal primers that hybridize to the universal priming sites on the primers resulting in the formation amplicons. Amplicons are labeled with either labeled primers or labeled dNTPs and detected as an indication of the presence of a particular allele.

DETAILED DESCRIPTION OF THE INVENTION

The present invention is directed to a variety of compositions and methods directed to multiplexed analysis of nucleic acids. In a preferred embodiment the methods are directed to multiplexing of nucleic acid detection, genotyping and amplification reactions. While a large body of literature and methods exist for the use of high density biochips comprising nucleic acids, the preparation of samples containing target sequences to place on the biochips has not been significantly multiplexed to allow true high throughput methodologies. The present invention is directed to the use of a variety of methods that allow the multiplexed amplification of target sequences prior to detection by any of a variety of methods including placement on an array for detection, mass spectrometry, electrophoretic techniques, FACS analysis, and the like.

In general, the method includes a complexity reduction component, a specificity step and an amplification step. Preferably complexity reduction is performed first. This is followed, in some embodiments, by the genotyping reaction, followed by multiplexed amplification. Generally, the specificity step includes an enzymatic reaction such as a genotyping reaction as described below. Alternatively, the multiplexed amplification reaction is done first, i.e. following complexity reduction, followed by a genotyping reaction. In both instances, the resulting amplicons are then detected, by a variety of detection methods including utilizing solid support arrays (both random and ordered), liquid arrays, or using technologies such as FACS sorting or mass spectroscopy.

Accordingly, the present invention relates to the multiplex amplification and detection of target analytes in a sample. As used herein, the phrase "multiplex" or grammatical equivalents refers to the detection, analysis or amplification of more than one target sequence of interest. In one embodiment multiplex refers to at least 100 or 200 different target sequences while at least 500 different target sequences is preferred. More preferred is at least 1000, with more than 5000 or 10,000 particularly preferred and more than 50,000 or 100,000 most preferred. Detection is performed on a variety of platforms as described herein.

Accordingly, the present invention provides methods for the detection of nucleic acid target sequences in a sample. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples; purified samples, such as purified genomic DNA, RNA, proteins, etc.; raw samples (bacteria, virus, genomic DNA, etc.). As will be appreciated by those in the art, virtually any experimental manipulation may have been done on the sample.

If required, the target sequence is prepared using known techniques. For example, the sample may be treated to lyse the cells, using known lysis buffers, sonication, electroporation, etc., with purification and amplification as outlined below occurring as needed, as will be appreciated by those in the art. In addition, the reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents which may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

In addition, when nucleic acids are to be detected preferred methods utilize cutting or shearing techniques to cut the nucleic acid sample containing the target sequence into a size that will facilitate handling and hybridization to the target, particularly for genomic DNA samples. This may be accomplished by shearing the nucleic acid through mechanical forces (e.g. sonication) or by cleaving the nucleic acid using restriction endonucleases, or any other methods known in the art.

In addition, in most embodiments, double stranded target nucleic acids are denatured to render them single stranded so as to permit hybridization of the primers and other probes of the invention. A preferred embodiment utilizes a thermal step, generally by raising the temperature of the reaction to about 95° C., although pH changes and other techniques may also be used.

The present invention provides compositions and methods for detecting the presence or absence of target nucleic acid sequences in a sample. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This allows for better detection of mismatches. Similarly, due to their non-ionic nature, hybridization of the bases attached to these backbones is relatively insensitive to salt concentration.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

The compositions and methods of the invention are directed to the multi-plexed detection of target sequences. The term "target sequence" or "target nucleic acid" or grammatical equivalents herein means a nucleic acid sequence on a single strand of nucleic acid. The target sequence may be a portion of a gene, a regulatory sequence, genomic DNA, cDNA, RNA including mRNA and rRNA, or others. A preferred embodiment utilizes genomic DNA as the primary target sequence.

As is outlined herein, the target sequence may be a target sequence from a sample, or a secondary target such as a product of a reaction such as a detection sequence from an invasive cleavage reaction, a ligated probe from an OLA reaction, an extended probe from a PCR reaction, or PCR amplification product, ("amplicon") etc.

The target sequence may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art. The target sequence may also be comprised of different target domains; for example, in "sandwich" type assays as outlined below, a first target domain of the sample target sequence may hybridize to a capture probe or a portion of capture extender probe, a second target domain may hybridize to a portion of an amplifier probe, a label probe, or a different capture or capture extender probe, etc. In addition, the target domains may be adjacent (i.e. contiguous) or separated. For example, when LCR techniques are used, a first primer may hybridize to a first target domain and a second primer may hybridize to a second target domain; either the domains are adjacent, or they may be separated by one or more nucleotides, coupled with the use of a polymerase and dNTPs, as is more fully outlined below.

The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

As outlined herein, in preferred embodiments the target sequence comprises a position for which sequence information is desired, generally referred to herein as the "detection position" or "detection locus". In a preferred embodiment, the detection position is a single nucleotide, although in some embodiments, it may comprise a plurality of nucleotides, either contiguous with each other or separated by one or more nucleotides. By "plurality" as used herein is meant at least two. As used herein, the base which basepairs with a detection position base in a hybrid is termed a "readout position" or an "interrogation position"; thus many of the first or second step probes of the invention comprise an interrogation position.

In some embodiments, as is outlined herein, the target sequence may not be the sample target sequence but instead is a product of a reaction herein, sometimes referred to herein as a "secondary" or "derivative" target sequence, or an "amplicon".

Accordingly, in a preferred embodiment the present multiplexed detection scheme includes at least one complexity reduction component, at least one specificity component and at least one amplification component. In addition, the method includes detection of the product of the reaction.

The methods of the invention can take on a wide variety of configurations, as are shown in the figures and described in more detail below. Generally these components include a complexity reduction component, a specificity component and an amplification component. The components can be configured in a variety of ways as disclosed below. That is, in one embodiment a complexity reduction step is first performed. This is followed by either the amplification or specificity step. Alternatively, the specificity step is performed first. This can be followed by the complexity reduction or amplification step. Alternatively, amplification is first performed. This is followed by the complexity and specificity steps.

While the above indicates that each of the three components can be performed in any order. One of skill in the art will appreciate that when amplification is performed first, there will likely be some degree of complexity reduction or specificity involved. In addition, when specificity components are performed first, there will be a degree of complexity reduction. In addition, in some embodiments when amplification is first performed, there will be some degree of specificity and complexity reduction. However, as described below, the method generally includes three components.

Probes and Primers

As one of skill in the art appreciates, there are several probes or primers that are used in the present invention. These probes/primers can take on a variety of configurations and may have a variety of structural components described in more detail below. The first step probe may be either an allele specific probe or locus specific probe. By "allele specific" probe or primer is meant a probe or primer that either hybridizes to a target sequence and discriminates between alleles or hybridizes to a target sequence and is modified in an allele specific manner. By "locus specific" probe or primer is meant a probe or primer that hybridizes to a target sequence in a locus specific manner, but does not necessarily discriminate between alleles. A locus specific primer also may be modified, i.e. extended as described below, such that it includes information about a particular allele, but the locus specific primer does not discriminate between alleles.

In many embodiments, the probes or primers comprise one or more universal priming site(s) and/or adapters, both of which are described below.

The size of the primer and probe nucleic acid may vary, as will be appreciated by those in the art with each portion of the probe and the total length of the probe in general varying from 5 to 500 nucleotides in length. Each portion is preferably between 10 and 100 being preferred, between 15 and 50 being particularly preferred, and from 10 to 35 being especially preferred, depending on the use and amplification technique. Thus, for example, the universal priming site(s) of the probes are each preferably about 15-20 nucleotides in length, with 18 being especially preferred. The adapter sequences of the probes are preferably from 15-25 nucleotides in length, with 20 being especially preferred. The target specific portion of the probe is preferably from 15-50 nucleotides in length. In addition, the primer may include an additional amplification priming site. In a preferred embodiment the additional amplification priming site is a T7 RNA polymerase priming site.

In a preferred embodiment, the allele or locus specific probe or probes comprises a target domain substantially complementary to a first domain of the target sequence. In general, probes of the present invention are designed to be complementary to a target sequence (either the target sequence of the sample or to other probe sequences, as is described herein), such that hybridization of the target and the probes of the present invention occurs. This complementarity need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions.

In one embodiment the target specific portion includes a combinatorial mixture of each nucleotide at each position. In addition the primer includes a universal priming sequence and an allele specific position. Preferably the universal priming sequence is specific for the particular nucleotide at the allele specific position. That is, in this embodiment the locus-specific allele selectivity portions of the primer are replaced with a universal targeting domain that includes region where each position is represented by a combinatorial mixture of nucleotides. One of the positions in the universal region (not necessarily the 3' position) is paired with the allele or SNP to be analyzed. The base at this position is associated with an identifier such as a particular adapter in the primer or with a particular universal priming sequence in the primer (FIG. 9).

In a preferred configuration, each of the four bases is associated with a different sequence, i.e. universal priming sequence, each sequence having similar amplification efficiencies. For amplification, each of the four primers is labeled with a different label. In an alternate embodiment it is possible to substitute a universal, i.e. promiscuous (inosine, for example) base at one or more positions in the universal sequence. The primer finds use in extension reactions and ligation reactions as described herein. In addition the primers find use in linear amplification schemes as depicted in FIG. 10. It should be noted that one advantage of using the universal targeting domain is that shorter oligonucleotides can be used. Thus, when universal target domains are used, these domains are preferably from about 5 to 15 nucleotides in length with from 7 to 10 being particularly preferred.

In a preferred embodiment, one of the probes further comprises an adapter sequence, (sometimes referred to in the art as "zip codes" or "bar codes"). Adapters facilitate immobilization of probes to allow the use of "universal arrays". That is, arrays (either solid phase or liquid phase arrays) are generated that contain capture probes that are not target specific, but rather specific to individual (preferably) artificial adapter sequences.

Thus, an "adapter sequence" is a nucleic acid that is generally not native to the target sequence, i.e. is exogenous, but is added or attached to the target sequence. It should be noted that in this context, the "target sequence" can include the primary sample target sequence, or can be a derivative target such as a reactant or product of the reactions outlined herein; thus for example, the target sequence can be a PCR product, a first ligation probe or a ligated probe in an OLA reaction, etc. The terms "barcodes", "adapters", "addresses", "tags" and "zipcodes" have all been used to describe artificial sequences that are added to amplicons to allow separation of nucleic acid fragment pools. One preferred form of adapters are hybridization adapters. In this embodiment adapters are chosen so as to allow hybridization to the complementary capture probes on a surface of an array. Adapters serve as unique identifiers of the probe and thus of the target sequence. In general, sets of adapters and the corresponding capture probes on arrays are developed to minimize cross-hybridization with both each other and other components of the reaction mixtures, including the target sequences and sequences on the larger nucleic acid sequences outside of the target sequences (e.g. to sequences within genomic DNA). Other forms of adapters are mass tags that can be separated using mass spectroscopy, electrophoretic tags that can be separated based on electrophoretic mobility, etc. Some adapter sequences are outlined in U.S. Ser. No. 09/940,185, filed Aug. 27, 2001, which published as U.S. 2003/0096239 and is now abandoned and is hereby incorporated by reference in its entirety. Preferred adapters are those that meet the following criteria. They are not found in a genome, preferably a human genome, and they do not have undesirable structures, such as hairpin loops.

As will be appreciated by those in the art, the attachment, or joining, of the adapter sequence to the target sequence can be done in a variety of ways. In a preferred embodiment, the adapter sequences are added to the primers of the reaction (extension primers, amplification primers, readout probes, genotyping primers, Rolling Circle primers, etc.) during the chemical synthesis of the primers. The adapter then gets added to the reaction product during the reaction; for example, the primer gets extended using a polymerase to form the new target sequence that now contains an adapter sequence. Alternatively, the adapter sequences can be added enzymatically. Furthermore, the adapter can be attached to the target after synthesis; this post-synthesis attachment can be either covalent or non-covalent. In a preferred embodiment the adapter is added to the target sequence or associated with a particular allele during an enzymatic step. That is, to achieve the level of specificity necessary for highly multiplexed reactions, the product of the specificity or allele specific reaction preferably also includes at least one adapter sequence.

In this embodiment, one or more of the specificity primers comprises a first portion comprising the adapter sequence and a second portion comprising the priming sequence. Extending the amplification primer as is well known in the art results in target sequences that comprise the adapter sequences. The adapter sequences are designed to be substantially complementary to capture probes.

In addition, as will be appreciated by those in the art, the adapter can be attached either on the 3' or 5' ends, or in an internal position, depending on the configuration of the system, as generally outlined in the figures.

In one embodiment the use of adapter sequences allow the creation of more "universal" surfaces; that is, one standard array, comprising a finite set of capture probes can be made and used in any application. The end-user can customize the array by designing different soluble target probes, which, as will be appreciated by those in the art, is generally simpler and less costly. In a preferred embodiment, an array of different and usually artificial capture probes are made; that is, the capture probes do not have complementarity to known target sequences. The adapter sequences can then be incorporated in the target probes.

As will be appreciated by those in the art, the length of the adapter sequences will vary, depending on the desired "strength" of binding and the number of different adapters desired. In a preferred embodiment, adapter sequences range from about 6 to about 500 basepairs in length, with from about 8 to about 100 being preferred, and from about 10 to about 25 being particularly preferred.

In a preferred embodiment, the adapter sequence uniquely identifies the target analyte to which the target probe binds. That is, while the adapter sequence need not bind itself to the target analyte, the system allows for identification of the target analyte by detecting the presence of the adapter. Accordingly, following a binding or hybridization assay and washing, the probes including the adapters are amplified. Detection of the adapter then serves as an indication of the presence of the target analyte.

In one embodiment the adapter includes both an identifier region and a region that is complementary to capture probes on a universal array as described above. In this embodiment, the amplicon hybridizes to capture probes on a universal array. Detection of the adapter is accomplished following hybridization with a probe that is complementary to the adapter sequence. Preferably the probe is labeled as described herein.

In general, unique adapter sequences are used for each unique target analyte. That is, the elucidation or detection of a particular adapter sequence allows the identification of the target analyte to which the target probe containing that adapter sequence bound. However, in some cases, it is possible to "reuse" adapter sequences and have more than one target analyte share an adapter sequence.

In a preferred embodiment the adapters contain different sequences or properties that are indicative of a particular target molecule. That is, each adapter uniquely identifies a target sequence. As described above, the adapters are amplified to form amplicons. The adapter is detected as an indication of the presence of the target analyte, i.e. the particular target nucleic acid.

The use of adapters in combination with amplification following a specific binding event allows for highly multiplexed reactions to be performed.

Also, the probes are constructed so as to contain the necessary priming site or sites for the subsequent amplification scheme. In a preferred embodiment the priming sites are universal priming sites. By "universal priming site" or "universal priming sequences" herein is meant a sequence of the probe that will bind a primer for amplification.

In a preferred embodiment, one universal priming sequence or site is used. In this embodiment, a preferred universal priming sequence is the RNA polymerase T7 sequence, that allows the T7 RNA polymerase make RNA copies of the adapter sequence as outlined below. Additional disclosure regarding the use of T7 RNA polymerase is found in U.S. Pat. Nos. 6,291,170, 5,891,636, 5,716,785, 5,545, 522, 5,922,553, 6,225,060 and 5,514,545, all of which are expressly incorporated herein by reference.

In a preferred embodiment, for example when amplification methods requiring two primers such as PCR are used, each probe preferably comprises an upstream universal priming site (UUP) and a downstream universal priming site (DUP). Again, "upstream" and "downstream" are not meant to convey a particular 5'-3' orientation, and will depend on the orientation of the system. Preferably, only a single UUP sequence and a single DUP sequence is used in a probe set, although as will be appreciated by those in the art, different assays or different multiplexing analysis may utilize a plurality of universal priming sequences. In some embodiments probe sets may comprise different universal priming sequences. In addition, the universal priming sites are preferably located at the 5' and 3' termini of the target probe (or the ligated probe), as only sequences flanked by priming sequences will be amplified.

In addition, universal priming sequences are generally chosen to be as unique as possible given the particular assays and host genomes to ensure specificity of the assay. However, as will be appreciated by those in the art, sets of priming sequences/primers may be used; that is, one reaction may utilize 500 target probes with a first priming sequence or set of sequences, and an additional 500 probes with a second sequence or set of sequences.

As will be appreciated by those in the art, when two priming sequences are used, the orientation of the two priming sites is generally different. That is, one PCR primer will directly hybridize to the first priming site, while the other PCR primer will hybridize to the complement of the second priming site. Stated differently, the first priming site is in sense orientation, and the second priming site is in antisense orientation.

As will be appreciated by those in the art, in general, highly multiplexed reactions can be performed, with all of the universal priming sites being the same for all reactions. Alternatively, "sets" of universal priming sites and corresponding probes can be used, either simultaneously or sequentially. The universal priming sites are used to amplify the modified probes to form a plurality of amplicons that are then detected in a variety of ways, as outlined herein. In preferred embodiments, one of the universal priming sites is a T7 site. In some embodiments this priming site serves as a template for the synthesis of RNA.

Accordingly, the present invention provides first target probe sets. By "probe set" herein is meant a plurality of target probes that are used in a particular multiplexed assay. In this context, plurality means at least two, with more than 10 being preferred, depending on the assay, sample and purpose of the test. In one embodiment the probe set includes more than 100, with more than 500 probes being preferred and more than 1000 being particularly preferred. In a particularly preferred embodiment each probe contains at least 5000, with more than 10,000 probes being most preferred.

Accordingly, the present invention provides first target probe sets that each comprise at least a first universal priming site.

In a preferred embodiment, the target probe may also comprise a label sequence, i.e. a sequence that can be used to bind label probes and is substantially complementary to a label probe. This system is sometimes referred to in the art as "sandwich-type" assays. That is, by incorporating a label sequence into the target probe, which is then amplified and present in the amplicons, a label probe comprising primary (or secondary) detection labels can be added to the mixture, either before addition to the array or after. This allows the use of high concentrations of label probes for efficient hybridization. In one embodiment, it is possible to use the same label sequence and label probe for all target probes on an array; alternatively, different target probes can have a different label sequence. Similarly, the use of different label sequences can facilitate quality control; for example, one label sequence (and one color) can be used for one strand of the target, and a different label sequence (with a different color) for the other; only if both colors are present at the same basic level is a positive called.

Thus, the present invention provides target probes that comprise any, all or any combination of universal priming sequences, bioactive agents (e.g. target specific portion(s)), adapter sequence(s), optionally an additional amplification priming sequence such as T7 RNA priming sequence and optionally label sequences. These target probes are then added to the target sequences to form hybridization complexes. As will be appreciated by those in the art, when nucleic acids are the target, the hybridization complexes contain portions that are double stranded (the target-specific sequences of the target probes hybridized to a portion of the target sequence) and portions that are single stranded (the ends of the target probes comprising the universal priming sequences and the adapter sequences, and any unhybridized portion of the target sequence, such as poly(A) tails, as outlined herein).

Complexity Reduction

Complexity reduction is a principal component of the multiplex scheme set forth herein. Generally, complexity reduction is a method for enriching for a particular target or locus. That is, complexity reduction is considered a method that results in removal of non-target nucleic acids from the sample or removal of probes/primers that have not hybridized correctly or at all to a target nucleic acid. In addition, complexity reduction includes removal of probes that have not been modified during a enzymatic step. That is, complexity reduction includes removing non-target nucleic acids, i.e. enriching for target nucleic acids or removing non-hybridized probes or primers prior to an enzymatic step, i.e. either an amplification or specificity step, or both.

There are a variety of ways one can include a complexity reduction step. These include, but are not limited to, selective immobilization of target nucleic acids or probes/primers that are modified in a target specific manner, selective removal of non-target nucleic acids, and selective destruction of non-target nucleic acids. Such destruction includes but is not limited to denaturation, degradation or cleavage of non-target nucleic acids. In addition, complexity reduction can include components such as target selective amplification, although this also includes amplification and components.

In a preferred embodiment complexity reduction is accomplished by selectively immobilizing a primer that has been modified in a target specific manner. That is, either locus specific or allele specific primers are hybridized with a target. The target can be immobilized or in solution. Following hybridization, the primer is extended in a primer extension reaction. Preferably either the primer or NTPs include a purification tag as described herein that allows for removal or purification of the extended product from the reaction mixture. Once extended, generally the modified primer is immobilized on a solid support as described herein. Following immobilization of the modified primer, the support is washed to remove both non-target nucleic acids and primers that were not modified, i.e. extended. The immobilized primers, thus, include information about the target locus including particular allelic information. This results in enrichment of target nucleic acids or removal of non-target nucleic acids.

In a preferred embodiment the complexity reduction component includes selective immobilization of target nucleic acids. That is, target nucleic acids are preferentially immobilized on a solid support rather than non-target nucleic acids.

In this embodiment target DNA is preferably reduced in size initially. This is easily accomplished by methods as known in the art such as, but not limited to, shearing or cleaving with restriction enzymes. The target nucleic acid is contacted with probes that hybridize to the targets. Preferably the hybridization is performed under low stringency conditions such that the probes do not discriminate between alleles of a particular locus. The resulting complexes are then immobilized on a support. In a preferred embodiment the probes are labeled with a purification tag as described herein to allow for immobilization. Following immobilization, the support is washed to remove non-hybridized targets, while leaving targets that are substantially complementary to the probes immobilized on the solid support. After removal of non-hybridized probes, the target nucleic acids can be removed with a stringent wash. This allows for enrichment of target sequences that are then available for further analysis.

In one embodiment, the target sequence, probe or primer, including modified primer, is attached to a first solid support. By "substrate" or "solid support" or other grammatical equivalents herein is meant any material that is appropriate for or can be modified to be appropriate for the attachment of the target sequences. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Magnetic beads and high throughput microtier plates are particularly preferred.

The composition and geometry of the solid support vary with its use. In this particular embodiment, supports comprising microspheres or beads are preferred for the first solid support. By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphited, titanium dioxide, latex or cross-linked dextrans such as Sepharose, cellulose, nylon, cross-linked micelles and teflon, as well as any other materials outlined herein for solid supports may all be used. "*Microsphere Detection Guide*" from Bangs Laboratories, Fishers Ind. is a helpful guide. Preferably, in this embodiment, when complexity reduction is performed, the microspheres are magnetic microspheres or beads.

The beads need not be spherical; irregular particles may be used. In addition, the beads may be porous, thus increasing the surface area of the bead available for assay. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

The target sequence, probe or primer is attached to the first solid support in a number of ways. In a preferred embodiment, purification tags are used. By "purification tag" herein is meant a moiety which can be used to purify a strand of nucleic acid, usually via attachment to a solid support as outlined herein. Suitable purification tags include members of binding partner pairs. For example, the tag may be a hapten or antigen, which will bind its binding partner. In a preferred embodiment, the binding partner can be attached to a solid support as depicted herein and in the figures. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

Additional techniques include, but are not limited to, enzymatic attachment, chemical attachment, photochemistry or thermal attachment and absorption.

In a preferred embodiment, as outlined herein, enzymatic techniques are used to attach the target nucleic acid, probe or primer to the support. For example, terminal transferase end-labeling techniques can be used as outlined above; see Hermanson, Bioconjugate Techniques, San Diego, Academic Press, pp 640-643. In this embodiment, a nucleotide labeled with a secondary label (e.g. a binding ligand, such as biotin) is added to a terminus of the target nucleic acid; supports coated or containing the binding partner (e.g. streptavidin) can thus be used to immobilize the target nucleic acid. Alternatively, the terminal transferase can be used to add nucleotides with special chemical functionalities that can be specifically coupled to a support. Preferred embodiments utilize the addition of biotinylated nucleotides followed by capture on streptavidin coated magnetic beads. Similarly, random-primed labeling or nick-translation labeling (supra, pp. 640-643) can also be used. In some embodiments the probe or primer are synthesized with biotinylated nucleotides or biotinylated after synthesis by methods as described herein.

In a preferred embodiment, chemical labeling (supra, pp. 6444-671) can be used. In this embodiment, bisulfate-catalyzed transamination, sulfonation of cytosine residues, bromine activation of T, C and G bases, periodate oxidation of RNA or carbodiimide activation of 5' phosphates can be done.

In a preferred embodiment, photochemistry or heat-activated labeling is done (supra, p 162-166). Thus for example, aryl azides and nitrenes preferably label adenosines, and to a less extent C and T (Aslam et al., Bioconjugation: Protein Coupling Techniques for Biomedical Sciences; New York, Grove's Dictionaries, 833 pp.). Psoralen or angelicin compounds can also be used (Aslam, p 492, supra). The preferential modification of guanine can be accomplished via intercalation of platinum complexes (Aslam, supra).

In a preferred embodiment, the target nucleic acid can be absorbed onto positively charged surfaces, such as an amine coated solid phase. The target nucleic acid can be cross-linked to the surface after physical absorption for increased retention (e.g. PEI coating and glutaraldehyde cross-linking; Aslam, supra, p. 485).

In a preferred embodiment, direct chemical attached or photocrosslinking can be done to attach the target nucleic acid to the solid phase, by using direct chemical groups on the solid phase substrate. For example, carbodiimide activation of 5' phosphates, attachment to exocyclic amines on DNA bases, and psoralen can be attached to the solid phase for crosslinking to the DNA. Other methods of tagging and immobilizing nucleic acids are described in U.S. Ser. No. 09/931,285, filed Aug. 16, 2001, which is expressly incorporated herein by reference.

Once attached to the first solid support, the target sequence, probe or primers are amenable to analysis as described herein.

In some embodiments when degradation is the preferred method of performing complexity reduction, the ddTNPs or dNTPs that are added during the reaction confer protection from degradation (whether chemical or enzymatic). Thus, after the assay, the degradation components are added, and unreacted primers are degraded, leaving only the reacted primers. Labeled protecting groups are particularly preferred; for example, 3'-substituted-2'-dNTPs can contain anthranylic derivatives that are fluorescent (with alkali or enzymatic treatment for removal of the protecting group).

In a preferred embodiment, the secondary label is a nuclease inhibitor, such as thiol NTPs. In this embodiment, the chain-terminating NTPs are chosen to render extended primers resistant to nucleases, such as 3'-exonucleases. Addition of an exonuclease will digest the non-extended primers leaving only the extended primers to bind to the capture probes on the array. This may also be done with OLA, wherein the ligated probe will be protected but the unprotected ligation probe will be digested.

In this embodiment, suitable 3'-exonucleases include, but are not limited to, exo I, exo III, exo VII, and 3'-5' exophosphodiesterases. That is, treatment with single stranded nucleases (either endonucleases or exonucleases) will effectively remove excess nucleic acid sequences that are non-complementary to the locus specific primer or extension product (see FIG. 11). Nuclease treatment can be performed either prior to or after separation, i.e. immobilization and washing, of purified nucleic acid targets.

Alternatively, an 3' exonuclease may be added to a mixture of 3' labeled biotin/streptavidin; only the unreacted oligonucleotides will be degraded. Following exonuclease treatment, the exonuclease and the streptavidin can be degraded using a protease such as proteinase K. The surviving nucleic acids (i.e. those that were biotinylated) are then hybridized to the array.

In a preferred embodiment the non-hybridized nucleic acids are removed by washing. In this embodiment the hybridization complexes are immobilized on a solid support and washed under conditions sufficient to remove non-hybridized nucleic acids, i.e. non-hybridized probes and sample nucleic acids. In a particularly preferred embodiment immobilized complexes are washed under conditions sufficient to remove imperfectly hybridized complexes. That is, hybridization complexes that contain mismatches are also removed in the wash steps.

A variety of hybridization or washing conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of helix destabilizing agents such as formamide. The hybridization or washing conditions may also vary when a non-ionic backbone, i.e. PNA is used, as is known in the art. In addition, cross-linking agents may be added after target binding to cross-link, i.e. covalently attach, the two strands of the hybridization complex.

In one embodiment the hybridization complexes are immobilized by binding of a purification tag to the solid support. That is, a purification tag is incorporated into the hybridization complexes. Purification tags are described herein and can be incorporated into hybridization complexes in a variety of ways. In one embodiment the locus specific probes contain purification tags as described herein. That is, the probe is synthesized with a purification tag, i.e. biotinylated nucleotides, or a purification tag is added to the probe. Thus, upon hybridization with target nucleic acids, immobilization of the hybridization complexes is accomplished by a purification tag. The purification tag associates with the solid support.

Purification tags are described herein. In a preferred embodiment the purification tag is biotin. That is, preferably the first probe is labeled with biotin. The labeled hybridization complex, therefore, binds to streptavidin coated solid support. Solid supports also are described herein. In a preferred embodiment the solid support is streptavidin coated magnetic beads.

The purification tag also can be incorporated into the locus specific primer following a primer extension reaction as described more fully below. Briefly, following hybridization of locus specific primers with target nucleic acids, a polymerase extension reaction is performed. In this embodiment tagged nucleotides, i.e. biotinylated nucleotides, are incorporated into the primer as a result of the extension reaction. That is, once the target sequence and the first probe sequence have hybridized, the method of this embodiment further comprises the addition of a polymerase and at least one nucleotide (dNTP) labeled with a purification tag. Suitable DNA polymerases include, but are not limited to, the Klenow fragment of DNA polymerase I, SEQUENASE 1.0 and SEQUENASE 2.0 (U.S. Biochemical), T5 DNA polymerase and Phi29 DNA polymerase. In this embodiment, it also is important to anneal under high stringency conditions so that only correctly hybridized probes and target nucleic acids are extended.

In addition, the purification tag can be incorporated into the target nucleic acid. In this embodiment, the target nucleic acid is labeled with a purification tag and immobilized to the solid support as described above. Preferably the tag is biotin.

Once formed, the tagged extension product is immobilized on the solid support as described above. Once immobilized, the complexes are washed so as to remove unhybridized nucleic acids.

Thus, a complexity reduction includes a locus specific selection of target nucleic acids. Non-specific or non-target nucleic acids are removed.

Once unhybridized probes and non-target nucleic acids have been removed, the probes, primers or hybridization complexes are generally subjected to an extension reaction. As outlined herein, the probes, primers or hybridization complexes can be immobilized or in solution after the optional complexity reduction step. Using the hybridized locus specific or allele specific probe as a primer, extension enzyme such as a polymerase and dNTPs are added to the assay mixture for extension of the primer. The resulting extended primer thus includes sequence information of the target nucleic acid, including the sequence of the specific allele to be detected. Thus, the extended primer serves as the template in subsequent specificity steps to identify the nucleotide at the detection position, i.e. the particular allele to be detected.

By "extension enzyme" herein is meant an enzyme that will extend a sequence by the addition of NTPs. As is well known in the art, there are a wide variety of suitable extension enzymes, of which polymerases (both RNA and DNA, depending on the composition of the target sequence and precircle probe) are preferred. Preferred polymerases are those that lack strand displacement activity, such that they will be capable of adding only the necessary bases at the end of the probe, without further extending the probe to include nucleotides that are complementary to a targeting domain and thus preventing circularization. Suitable polymerases include, but are not limited to, both DNA and RNA polymerases, including the Klenow fragment of DNA polymerase I, SEQUENASE 1.0 and SEQUENASE 2.0 (U.S. Biochemical), T5 DNA polymerase, Phi29 DNA polymerase and various RNA polymerases such as from *Thermus* sp., or Q beta replicase from bacteriophage, also SP6, T3, T4 and T7 RNA polymerases can be used, among others.

Even more preferred polymerases are those that are essentially devoid of a 5' to 3' exonuclease activity, so as to assure that the probe will not be extended past the 5' end of the probe. Exemplary enzymes lacking 5' to 3' exonuclease activity include the Klenow fragment of the DNA Polymerase and the Stoffel fragment of DNAPTaq Polymerase. For example, the Stoffel fragment of Taq DNA polymerase lacks 5' to 3' exonuclease activity due to genetic manipulations, which result in the production of a truncated protein lacking the N-terminal 289 amino acids. (See e.g., Lawyer et al., J. Biol. Chem., 264:6427-6437 [1989]; and Lawyer et al., PCR Meth. Appl., 2:275-287 [1993]). Analogous mutant polymerases have been generated for polymerases derived from *T. maritima*, Tsps17, TZ05, Tth and Taf.

Even more preferred polymerases are those that lack a 3' to 5' exonuclease activity, which is commonly referred to as a proof-reading activity, and which removes bases which are mismatched at the 3' end of a primer-template duplex. Although the presence of 3' to 5' exonuclease activity provides increased fidelity in the strand synthesized, the 3' to 5' exonuclease activity found in thermostable DNA polymerases such as Tma (including mutant forms of Tma that lack 5' to 3' exonuclease activity) also degrades single-stranded DNA such as the primers used in the PCR, single-stranded templates and single-stranded PCR products. The integrity of the 3' end of an oligonucleotide primer used in a primer extension process is critical as it is from this terminus that extension of the nascent strand begins. Degradation of the 3' end leads to a shortened oligonucleotide which in turn results in a loss of specificity in the priming reaction (i.e., the shorter the primer the more likely it becomes that spurious or non-specific priming will occur).

Yet even more preferred polymerases are thermostable polymerases. For the purposes of this invention, a heat resistant enzyme is defined as any enzyme that retains most of its activity after one hour at 40° C. under optimal conditions. Examples of thermostable polymerase which lack both 5' to 3' exonuclease and 3' to 5' exonuclease include Stoffel fragment of Taq DNA polymerase. This polymerase lacks the 5' to 3' exonuclease activity due to genetic manipulation and no 3' to 5' activity is present as Taq polymerase is naturally lacking in 3' to 5' exonuclease activity. Tth DNA polymerase is derived form *Thermus thermophilus*, and is available form Epicentre Technologies, Molecular Biology Resource Inc., or Perkin-Elmer Corp. Other useful DNA polymerases which lack 3' exonuclease activity include a Vent[R](exo-), available from New England Biolabs, Inc., (purified from strains of *E. coli* that carry a DNA polymerase gene from the archaebacterium *Thermococcus litoralis*), and Hot Tub DNA polymerase derived from *Thermus flavus* and available from Amersham Corporation.

Other preferred enzymes which are thermostable and deprived of 5' to 3' exonuclease activity and of 3' to 5' exonuclease activity include AmpliTaq Gold. Other DNA polymerases, which are at least substantially equivalent may be used like other N-terminally truncated *Thermus aquaticus* (Taq) DNA polymerase I. the polymerase named KlenTaq I and KlenTaq LA are quite suitable for that purpose. Of course, any other polymerase having these characteristics can also be used according to the invention.

The conditions for performing the addition of one or more nucleotides at the 3' end of the probe will depend on the particular enzyme used, and will generally follow the conditions recommended by the manufacturer of the enzymes used.

In addition, it will be appreciated that more than one complexity reduction step can be performed. That is, following a first complexity reduction step, either the remaining target nucleic acid or the extended locus or allele specific primer, when applicable, are subjected to a subsequent complexity reduction step as described above. That is, an additional locus specific or allele specific primer is hybridized to the target nucleic acid, which can be either the original target nucleic acid or the extended primer, and unhybridized target nucleic acids are removed. This can be repeated as many times as necessary to achieve the required level of enrichment of target nucleic acid.

While the above has been described in the context of complexity reduction, it is appreciated that some level of specificity also is included in these steps. That is, as a result of hybridizing target nucleic acids with locus specific probes, specificity also in accomplished. This is particularly apparent when allele specific probes are used initially.

Specificity Component

Generally following at least one complexity reduction step a specificity step is included in the method of the invention. By "specificity component" is meant a step that discriminates between target nucleic acids, preferably at the level of the allele. That is, the specificity component is an allele specific step (e.g. genotyping or SNP analysis). While some level of specificity can be accomplished by simply hybridizing allele specific probes to the template (i.e. the product of the complexity reduction step above), in a preferred embodiment the specificity step includes an enzymatic step. That is, the fidelity of an enzymatic step improves specificity for allele discrimination. Preferred enzymes include DNA polymerases, RNA polymerases and ligases as described in more detail herein.

Polymerases are described above. Many ligases are known and are suitable for use in the invention, e.g. Lehman, Science, 186: 790-797 (1974); Engler et al, DNA Ligases, pages 3-30 in Boyer, editor, The Enzymes, Vol. 15B (Academic Press, New York, 1982); and the like. Preferred ligases include T4 DNA ligase, T7 DNA ligase, *E. coli* DNA ligase, Taq ligase, Pfu ligase, and Tth ligase. Protocols for their use are well known, e.g. Sambrook et al (cited above); Barany, PCR Methods an Applications, 1: 5-16 (1991); Marsh et al, Strategies, 5: 73-76 (1992); and the like. Generally, ligases require that a 5' phosphate group be present for ligation to the 3' hydroxyl of an abutting strand. Preferred ligases include thermostable or (thermophilic) ligases, such as pfu ligase, Tth ligase, Taq ligase and Ampligase™ DNA ligase (Epicentre Technologies, Madison, Wis.). Ampligase has a low blunt end ligation activity.

The preferred ligase is one which has the least mismatch ligation. The specificity of ligase can be increased by substituting the more specific NAD+-dependant ligases such as *E. coli* ligase and (thermostable) Taq ligase for the less specific T4 DNA ligase. The use of NAD analogues in the ligation reaction further increases specificity of the ligation reaction. See, U.S. Pat. No. 5,508,179 to Wallace et al.

In one embodiment the specificity component is performed with immobilized targets. That is, the products of the complexity reduction step are immobilized on a solid support as outlined herein and described in U.S. Ser. No. 09/931,285, filed Aug. 16, 2001, which is expressly incorporated herein by reference. As discussed herein the target of specificity reaction is referred to as a "specificity target". That is, the product of the complexity reduction step is the specificity target.

In one embodiment the support is the same support as in the initial complexity reduction step. In this embodiment the target nucleic acid is removed from the solid support prior to the specificity assay. The target nucleic acid can be removed by any method that denatures the hybridization complex resulting in release of the target nucleic acid. As one of skill in the art appreciates, in this embodiment the target nucleic acid is not covalently bound to the solid support. That is, it is the target probe that is stably attached to the support. That is, while the attachment of the probe is not necessarily covalent, it is stable enough to withstand denaturation of the hybridization complex and removal of the non-attached target nucleic acid.

In an alternative embodiment the specificity target is in solution. That is, following a complexity reduction step, the hybridization complex between the immobilized target nucleic acid and target probe, which has generally been modified (see above), is denatured and the modified target probe is eluted from the hybridization complex. In a preferred embodiment the specificity target is analyzed in solution. In an alternative embodiment the solution phase specificity target is immobilized on a subsequent solid support.

These specificity assays, i.e. genotyping techniques, fall into five general categories: (1) techniques that rely on traditional hybridization methods that utilize the variation of stringency conditions (temperature, buffer conditions, etc.) to distinguish nucleotides at the detection position; (2) extension techniques that add a base ("the base") to basepair with the nucleotide at the detection position; (3) ligation techniques, that rely on the specificity of ligase enzymes (or, in some cases, on the specificity of chemical techniques), such that ligation reactions occur preferentially if perfect complementarity exists at the detection position; (4) cleavage techniques, that also rely on enzymatic or chemical specificity such that cleavage occurs preferentially if perfect complementarity exists; and (5) techniques that combine these methods. See generally WO 00/63437, incorporated by reference in its entirety.

Competitive Hybridization

In a preferred embodiment, the use of competitive hybridization is performed to elucidate either the identity of the nucleotide(s) at the detection position or the presence of a mismatch. For example, sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, among others, all of which are hereby expressly incorporated by reference in their entirety).

It should be noted in this context that "mismatch" is a relative term and meant to indicate a difference in the identity of a base at a particular position, termed the "detection position" herein, between two sequences. In general, sequences that differ from wild type sequences are referred to as mismatches. However, particularly in the case of SNPs, what constitutes "wild type" may be difficult to determine as multiple alleles can be relatively frequently observed in the population, and thus "mismatch" in this context requires the artificial adoption of one sequence as a standard. Thus, for the purposes of this invention, sequences are referred to herein as "match" and "mismatch". Thus, the present invention may be used to detect substitutions, insertions or deletions as compared to a wild-type sequence.

In a preferred embodiment, a plurality of probes (sometimes referred to herein as "readout probes") are used to identify the base at the detection position. In this embodiment, each different readout probe comprises a different detection label (which, as outlined below, can be either a primary label or a secondary label) and a different base at the position that will hybridize to the detection position of the target sequence (herein referred to as the readout position) such that differential hybridization will occur. That is, all other parameters being equal, a perfectly complementary readout probe (a "match probe") will in general be more stable and have a slower off rate than a probe comprising a mismatch (a "mismatch probe") at any particular temperature. Accordingly, by using different readout probes, each with a different base at the readout position and each with a different label, the identification of the base at the detection position is elucidated.

Accordingly, in some embodiments a detectable label is incorporated into the readout probe. In a preferred embodiment, a set of readout probes are used, each comprising a different base at the readout position. In some embodiments, each readout probe comprises a different label, that is distinguishable from the others. For example, a first label may be used for probes comprising adenosine at the readout position, a second label may be used for probes comprising guanine at the readout position, etc. In a preferred embodiment, the length and sequence of each readout probe is identical except for the readout position, although this need not be true in all embodiments.

The number of readout probes used will vary depending on the end use of the assay. For example, many SNPs are biallelic, and thus two readout probes, each comprising an interrogation base that will basepair with one of the detection position bases. For sequencing, for example, for the discovery of SNPs, a set of four readout probes are used, although SNPs may also be discovered with fewer readout parameters.

As will be appreciated by those in the art and additionally outlined below, this system can take on a number of different configurations, including a solution phase assay and a solid phase assay.

Solution Phase Assay

In some embodiments a solution phase assay is performed followed by attaching the target sequence to a solid support such as an array. After the competitive hybridization has occurred, the target sequence is added to the support, which may take on several configurations, outlined below.

Solid Phase Assay

In a preferred embodiment, the competition reaction is done on a solid support, such as an array. This system may take on several configurations.

In a preferred embodiment, a sandwich assay of sorts is used. In this embodiment, the bead, when bead arrays are used, comprises a capture probe that will hybridize to a first target domain of a target sequence, and the readout probe will hybridize to a second target domain. In this embodiment, the first target domain may be either unique to the target, or may be an exogeneous adapter sequence added to the target sequence as outlined below, for example through the use of PCR reactions. Similarly, a sandwich assay is performed that utilizes a capture extender probe, as described below, to attach the target sequence to the array.

Alternatively, the capture probe itself can be the readout probe; that is, a plurality of microspheres are used, each comprising a capture probe that has a different base at the readout position. In general, the target sequence then hybridizes preferentially to the capture probe most closely matched. In this embodiment, either the target sequence itself is labeled (for example, it may be the product of an amplification reaction) or a label probe may bind to the target sequence at a domain remote from the detection position. In this embodiment, since it is the location on the array that serves to identify the base at the detection position, different labels are not required.

Stringency Variation

In a preferred embodiment, sensitivity to variations in stringency parameters are used to determine either the identity of the nucleotide(s) at the detection position or the presence of a mismatch. As a preliminary matter, the use of different stringency conditions such as variations in temperature and buffer composition to determine the presence or absence of mismatches in double stranded hybrids comprising a single stranded target sequence and a probe is well known.

With particular regard to temperature, as is known in the art, differences in the number of hydrogen bonds as a function of basepairing between perfect matches and mismatches can be exploited as a result of their different Tms (the temperature at which 50% of the hybrid is denatured). Accordingly, a hybrid comprising perfect complementarity will melt at a higher temperature than one comprising at least one mismatch, all other parameters being equal. (It should be noted that for the purposes of the discussion herein, all other parameters (i.e. length of the hybrid, nature of the backbone (i.e. naturally occurring or nucleic acid analog), the assay solution composition and the composition of the bases, including G-C content are kept constant). However, as will be appreciated by those in the art, these factors may be varied as well, and then taken into account.)

In general, as outlined herein, high stringency conditions are those that result in perfect matches remaining in hybridization complexes, while imperfect matches melt off. Similarly, low stringency conditions are those that allow the formation of hybridization complexes with both perfect and imperfect matches. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

As will be appreciated by those in the art, mismatch detection using temperature may proceed in a variety of ways, and is similar to the use of readout probes as outlined above. Again, as outlined above, a plurality of readout probes may be used in a sandwich format; in this embodiment, all the probes may bind at permissive, low temperatures (temperatures below the Tm of the mismatch); however, repeating the assay at a higher temperature (above the Tm of the mismatch) only the perfectly matched probe may bind. Thus, this system may be run with readout probes with different detectable labels, as outlined above. Alternatively, a single probe may be used to query whether a particular base is present.

Alternatively, as described above, the capture probe may serve as the readout probe; in this embodiment, a single label may be used on the target; at temperatures above the Tm of the mismatch, only signals from perfect matches will be seen, as the mismatch target will melt off.

Similarly, variations in buffer composition may be used to elucidate the presence or absence of a mismatch at the detection position. Suitable conditions include, but are not limited to, formamide concentration. Thus, for example, "low" or "permissive" stringency conditions include formamide concentrations of 0 to 10%, while "high" or "stringent" conditions utilize formamide concentrations of ≥40%. Low stringency conditions include NaCl concentrations of ≥1 M, and high stringency conditions include concentrations of ≤0.3 M. Furthermore, low stringency conditions include $MgCl_2$ concentrations of ≥10 mM, moderate stringency as 1-10 mM, and high stringency conditions include concentrations of ≤1 mM.

In this embodiment, as for temperature, a plurality of readout probes may be used, with different bases in the readout position (and optionally different labels). Running the assays under the permissive conditions and repeating under stringent conditions will allow the elucidation of the base at the detection position.

In one embodiment, the probes used as readout probes are "Molecular Beacon" probes as are generally described in Whitcombe et al., Nature Biotechnology 17:804 (1999), hereby incorporated by reference. As is known in the art, Molecular Beacon probes form "hairpin" type structures, with a fluorescent label on one end and a quencher on the other. In the absence of the target sequence, the ends of the hairpin hybridize, causing quenching of the label. In the presence of a target sequence, the hairpin structure is lost in favor of target sequence binding, resulting in a loss of quenching and thus an increase in signal.

In one embodiment, the Molecular Beacon probes can be the capture probes as outlined herein for readout probes. For example, different beads comprising labeled Molecular Beacon probes (and different bases at the readout position) are made optionally they comprise different labels. Alternatively, since Molecular Beacon probes can have spectrally resolvable signals, all four probes (if a set of four different bases with is used) differently labeled are attached to a single bead.

Extension Assays

In this embodiment the specificity target is immobilized on a solid support. In a preferred embodiment, extension genotyping is done. In this embodiment, any number of techniques are used to add a nucleotide to the readout position of a probe hybridized to the target sequence adjacent to the detection position. By relying on enzymatic specificity, preferentially a perfectly complementary base is added. All of these methods rely on the enzymatic incorporation of nucleotides at the detection position. This may be done using chain terminating dNTPs, such that only a single base is incorporated (e.g. single base extension methods), or under conditions that only a single type of nucleotide is added followed by identification of the added nucleotide (extension and pyrosequencing techniques).

Single Base Extension

In a preferred embodiment, single base extension (SBE; sometimes referred to as "minisequencing") is used to determine the identity of the base at the detection position. SBE utilizes an extension primer that may have at least one adapter sequence that hybridizes to the target nucleic acid immediately adjacent to the detection position, to form a hybridization complex. A polymerase (generally a DNA polymerase) is used to extend the 3' end of the primer with a nucleotide or nucleotide analog. In some embodiments the nucleotide or nucleotide analog is labeled with a detection label as described herein. Based on the fidelity of the enzyme, a nucleotide is only incorporated into the readout position of the growing nucleic acid strand if it is perfectly complementary to the base in the target strand at the detection position. The nucleotide may be derivatized such that no further extensions can occur, so only a single nucleotide is added. Once the labeled nucleotide is added, detection of the label proceeds as outlined herein. Again, amplification in this case is accomplished through cycling or repeated rounds of reaction/elution, although in some embodiments amplification is not necessary. Alternatively, in some embodiments, amplification is performed prior to the extension reaction. Alternatively, amplification is performed following the extension reaction.

The reaction is initiated by introducing the hybridization complex comprising the specificity target on the support to a solution comprising a first nucleotide. In some embodiments, the nucleotides comprise a detectable label, which may be either a primary or a secondary label. In addition, the nucleotides may be nucleotide analogs, depending on the configuration of the system. For example, if the dNTPs are added in sequential reactions, such that only a single type of dNTP can be added, the nucleotides need not be chain terminating. In addition, in this embodiment, the dNTPs may all comprise the same type of label.

Alternatively, if the reaction comprises more than one dNTP, the dNTPs should be chain terminating, that is, they have a blocking or protecting group at the 3' position such that no further dNTPs may be added by the enzyme. As will be appreciated by those in the art, any number of nucleotide analogs may be used, as long as a polymerase enzyme will still incorporate the nucleotide at the readout position. Preferred embodiments utilize dideoxy-triphosphate nucleotides (ddNTPs) and halogenated dNTPs. Generally, a set of nucleotides comprising ddATP, ddCTP, ddGTP and ddTTP is used, each with a different detectable label, although as outlined herein, this may not be required. Alternative preferred embodiments use acyclo nucleotides (NEN). These chain terminating nucleotide analogs are particularly good substrates for Deep vent (exo⁻) and thermosequenase.

In addition, as will be appreciated by those in the art, the single base extension reactions of the present invention allow the precise incorporation of modified bases into a growing nucleic acid strand. Thus, any number of modified nucleotides may be incorporated for any number of reasons, including probing structure-function relationships (e.g.

DNA:DNA or DNA:protein interactions), cleaving the nucleic acid, crosslinking the nucleic acid, incorporate mismatches, etc.

As will be appreciated by those in the art, the configuration of the genotyping SBE system can take on several forms.

Multi-Base Extension

In a preferred embodiment genotyping is accomplished by primer extension that does not use chain terminating nucleotides. As such, this genotyping is considered multi-base extension. The method includes providing an interrogator oligonucleotide designed to detect one allele of a given SNP. The number of oligonucleotides is determined by the number of distinct SNP alleles being probed. For instance, if one were probing 1000 SNPs, each with two alleles, 2000 oligonucleotides would be necessary. The interrogators are complementary to a stretch of DNA containing the SNP, with the terminal base of each interrogator corresponding to the SNP position, or with the SNP-specific position within the last 1, 2 3 or 4 nucleotides of the interrogator. In some preferred embodiments the interrogator is not the terminal position of the primer, but rather resides at a position 1, 2, 3, 4, 5 or 6 nucleotides from the 3' terminus of the primer. For example, when a SNP has an A and C allele, interrogators ending in T and G are provided and in some embodiments may be immobilized on separate elements (beads) to detect the two. Although both the match and the mismatch will hybridize to a given allele, only the match can act as a primer for a DNA polymerase extension reaction. Accordingly, following hybridization of the probes with the target DNA, a polymerase reaction is performed. This results in the extension of the hybrids with a DNA polymerase in the presence of labeled dNTPs. The labeled dNTPs are selectively incorporated into the extension product that results from the probe that is complementary to the SNP position.

In one embodiment, address oligonucleotides (adapters) are incorporated into the interrogator oligonucleotides. As such, in one embodiment one performs the hybridization and extension steps in fluid phase in the absence of beads. Each allele contains a unique adapter. After hybridization/extension the products are hybridized to an array of complementary address sequences for signal detection and analysis.

Solution Phase Assay

As for the OLA reaction described below, the reaction may be done in solution, and then the newly synthesized strands, with the base-specific detectable labels, can be detected. For example, they can be directly hybridized to capture probes that are complementary to the extension primers, and the presence of the label is then detected. As will be appreciated by those in the art, a preferred embodiment utilizes four different detectable labels, i.e. one for each base, such that upon hybridization to the capture probe on the array, the identification of the base can be done isothermally.

In a preferred embodiment, adapter sequences can be used in a solution format. In this embodiment, a single label can be used with a set of four separate primer extension reactions. In this embodiment, the extension reaction is done in solution; each reaction comprises a different dNTP with the label or labeled ddNTP when chain termination is desired. For each locus genotyped, a set of four different extension primers are used, each with a portion that will hybridize to the target sequence, a different readout base and each with a different adapter sequence of 15-40 bases, as is more fully outlined below. After the primer extension reaction is complete, the four separate reactions are pooled and hybridized to an array comprising complementary probes to the adapter sequences. A genotype is derived by comparing the probe intensities of the four different hybridized adapter sequences corresponding to a given locus.

In addition, since unextended primers do not comprise labels, the unextended primers need not be removed. However, they may be, if desired, as outlined below; for example, if a large excess of primers are used, there may not be sufficient signal from the extended primers competing for binding to the surface.

Alternatively, one of skill in the art could use a single label and temperature to determine the identity of the base; that is, the readout position of the extension primer hybridizes to a position on the capture probe. However, since the three mismatches will have lower Tms than the perfect match, the use of temperature could elucidate the identity of the detection position base.

Solid Phase Assay

Alternatively, the reaction may be done on a surface by capturing the target sequence and then running the SBE reaction, in a sandwich type format. In this embodiment, the capture probe hybridizes to a first domain of the target sequence (which can be endogeneous or an exogeneous adapter sequence added during an amplification reaction), and the extension primer hybridizes to a second target domain immediately adjacent to the detection position. The addition of the enzyme and the required NTPs results in the addition of the interrogation base. In this embodiment, each NTP must have a unique label. Alternatively, each NTP reaction may be done sequentially on a different array. As is known by one of skill in the art, ddNTP and dNTP are the preferred substrates when DNA polymerase is the added enzyme; NTP is the preferred substrate when RNA polymerase is the added enzyme.

Furthermore, capture extender probes can be used to attach the target sequence to the bead. In this embodiment, the hybridization complex comprises the capture probe, the target sequence and the adapter sequence.

Similarly, the capture probe itself can be used as the extension probe, with its terminus being directly adjacent to the detection position. Upon the addition of the target sequence and the SBE reagents, the modified primer is formed comprising a detectable label, and then detected. Again, as for the solution based reaction, each NTP must have a unique label, the reactions must proceed sequentially, or different arrays must be used. Again, as is known by one of skill in the art, ddNTP and dNTP are the preferred substrates when DNA polymerase is the added enzyme; NTP is the preferred substrate when RNA polymerase is the added enzyme.

In addition, as outlined herein, the target sequence may be directly attached to the array; the extension primer hybridizes to it and the reaction proceeds.

Variations on this include, where the capture probe and the extension probe adjacently hybridize to the target sequence. Either before or after extension of the extension probe, a ligation step may be used to attach the capture and extension probes together for stability. These are further described below as combination assays.

As will be appreciated by those in the art, the determination of the base at the detection position can proceed in several ways. In a preferred embodiment, the reaction is run with all four nucleotides (assuming all four nucleotides are required), each with a different label, as is generally outlined herein. Alternatively, a single label is used, by using four reactions In a preferred embodiment, universal primers or adapters specific for the nucleotide at a detection position are used and detected as outlined below.

Removal of Unextended Primers

In a preferred embodiment, for both SBE as well as a number of other reactions outlined herein, it is desirable to remove the unextended or unreacted primers from the assay mixture, and particularly from the array, as unextended primers will compete with the extended (labeled) primers in binding to capture probes, thereby diminishing the signal. The concentration of the unextended primers relative to the extended primer may be relatively high, since a large excess of primer is usually required to generate efficient primer annealing. Accordingly, a number of different techniques may be used to facilitate the removal of unextended primers. As outlined above, these generally include methods based on removal of unreacted primers by binding to a solid support, protecting the reacted primers and degrading the unextended ones, and separating the unreacted and reacted primers.

Separation Systems

The use of secondary label systems (and even some primary label systems) can be used to separate unreacted and reacted probes; for example, the addition of streptavidin to a nucleic acid greatly increases its size, as well as changes its physical properties, to allow more efficient separation techniques. For example, the mixtures can be size fractionated by exclusion chromatography, affinity chromatography, filtration or differential precipitation.

Non-Terminated Extension

In a preferred embodiment, methods of adding a single base are used that do not rely on chain termination. That is, similar to SBE, enzymatic reactions that utilize dNTPs and polymerases can be used; however, rather than use chain terminating dNTPs, regular dNTPs are used. This method relies on a time-resolved basis of detection; only one type of base is added during the reaction.

Pyrosequencing

Pyrosequencing is an extension and sequencing method that can be used to add one or more nucleotides to the detection position(s); it is very similar to SBE except that chain terminating NTPs need not be used (although they may be). Pyrosequencing relies on the detection of a reaction product, PPi, produced during the addition of an NTP to a growing oligonucleotide chain, rather than on a label attached to the nucleotide. One molecule of PPi is produced per dNTP added to the extension primer. That is, by running sequential reactions with each of the nucleotides, and monitoring the reaction products, the identity of the added base is determined.

The release of pyrophosphate (PPi) during the DNA polymerase reaction can be quantitatively measured by many different methods and a number of enzymatic methods have been described; see Reeves et al., Anal. Biochem. 28:282 (1969); Guillory et al., Anal. Biochem. 39:170 (1971); Johnson et al., Anal. Biochem. 15:273 (1968); Cook et al., Anal. Biochem. 91:557 (1978); Drake et al., Anal. Biochem. 94:117 (1979); WO93/23564; WO 98/28440; WO98/13523; Nyren et al., Anal. Biochem. 151:504 (1985); all of which are incorporated by reference. The latter method allows continuous monitoring of PPi and has been termed ELIDA (Enzymatic Luminometric Inorganic Pyrophosphate Detection Assay). A preferred embodiment utilizes any method which can result in the generation of an optical signal, with preferred embodiments utilizing the generation of a chemiluminescent or fluorescent signal.

A preferred method monitors the creation of PPi by the conversion of PPi to ATP by the enzyme sulfurylase, and the subsequent production of visible light by firefly luciferase (see Ronaghi et al., Science 281:363 (1998), incorporated by reference). In this method, the four deoxynucleotides (dATP, dGTP, dCTP and dTTP; collectively dNTPs) are added stepwise to a partial duplex comprising a sequencing primer hybridized to a single stranded DNA template and incubated with DNA polymerase, ATP sulfurylase, luciferase, and optionally a nucleotide-degrading enzyme such as apyrase. A dNTP is only incorporated into the growing DNA strand if it is complementary to the base in the template strand. The synthesis of DNA is accompanied by the release of PPi equal in molarity to the incorporated dNTP. The PPi is converted to ATP and the light generated by the luciferase is directly proportional to the amount of ATP. In some cases the unincorporated dNTPs and the produced ATP are degraded between each cycle by the nucleotide degrading enzyme.

Accordingly, a preferred embodiment of the methods of the invention is as follows. A substrate comprising the target sequences and extension primers, forming hybridization complexes, is dipped or contacted with a reaction volume (chamber or well) comprising a single type of dNTP, an extension enzyme, and the reagents and enzymes necessary to detect PPi. If the dNTP is complementary to the base of the target portion of the target sequence adjacent to the extension primer, the dNTP is added, releasing PPi and generating detectable light, which is detected as generally described in U.S. Ser. No. 09/151,877 which issued as U.S. Pat. No. 6,327,410 and U.S. Ser. No. 09/189,543 which is now abandoned, and PCT US98/09163 which published as WO1998050782, all of which are hereby incorporated by reference. If the dNTP is not complementary, no detectable signal results. The substrate is then contacted with a second reaction volume (chamber) comprising a different dNTP and the additional components of the assay. This process is repeated if the identity of a base at a second detection position is desirable.

In a preferred embodiment, washing steps may be done in between the dNTP reactions, as required. These washing steps may optionally comprise a nucleotide-degrading enzyme, to remove any unreacted dNTP and decreasing the background signal, as is described in WO 98/28440, incorporated herein by reference.

As will be appreciated by those in the art, the system can be configured in a variety of ways, including both a linear progression or a circular one; for example, four arrays may be used that each can dip into one of four reaction chambers arrayed in a circular pattern. Each cycle of sequencing and reading is followed by a 90 degree rotation, so that each substrate then dips into the next reaction well.

As for simple extension and SBE, the pyrosequencing systems may be configured in a variety of ways; for example, the target sequence may be immobilized in a variety of ways, including direct attachment of the target sequence; the use of a capture probe with a separate extension probe; the use of a capture extender probe, a capture probe and a separate extension probe; the use of adapter sequences in the target sequence with capture and extension probes; and the use of a capture probe that also serves as the extension probe.

One additional benefit of pyrosequencing for genotyping purposes is that since the reaction does not rely on the incorporation of labels into a growing chain, the unreacted extension primers need not be removed.

In addition, pyrosequencing can be used as a "switch" to activate a detectable enzymatic reaction, thus providing an amplification of sorts. The by-product of the polymerase reaction, PPi, is converted to ATP during pyrosequencing reactions. In standard pyrosequencing that utilizes a luciferase/luciferin assay, the detection sensitivity is limited because only a single photon is generated per nucleotide incorporation event. However, in a preferred embodiment, if PPi, or a simple enzymatic derivative such as Pi or ATP is used to "activate" an enzyme or protein, the detection sensitivity is increased. A number of different proteins are either "on" or "off" depending on their phosphorylation status. In this was, PPi (or ATP) acts a "switch" to turn on or off a stream of detection molecules, similar to the way a transistor controls a large flow of electricity by using a small current or potential to gat the process. That is, the generation of PPi results in an enzymatic cascade that results in a detectable event; the PPi generation results in a "switch". For example, ATP may be used to phosphorylate a peroxidase enzyme, which when phosphorylated becomes "active" like horse radish peroxidase (HRP). This HRP activity is then detected using standard hydrogen peroxide/luminol HRP detection systems. There are a large number of enzymes and proteins regulated by phosphorylation. What is important is that the activating or switch enzyme that utilizes Pi, PPi or ATP as the substrate discriminates the activating species from the original dNTP used in the extension reaction.

Allelic PCR

In a preferred embodiment, the method used to detect the base at the detection position is allelic PCR, referred to herein as "aPCR". As described in Newton et al., Nucl. Acid Res. 17:2503 (1989), hereby expressly incorporated by reference, allelic PCR allows single base discrimination based on the fact that the PCR reaction does not proceed well if the terminal 3'-nucleotide is mismatched, assuming the DNA polymerase being used lacks a 3'-exonuclease proofreading activity. Accordingly, the identification of the base proceeds by using allelic PCR primers (sometimes referred to herein as aPCR primers) that have readout positions at their 3' ends. Thus the target sequence comprises a first domain comprising at its 5' end a detection position.

In general, aPCR may be briefly described as follows. A double stranded target nucleic acid is denatured, generally by raising the temperature, and then cooled in the presence of an excess of a aPCR primer, which then hybridizes to the first target strand. If the readout position of the aPCR primer basepairs correctly with the detection position of the target sequence, a DNA polymerase (again, that lacks 3'-exonuclease activity) then acts to extend the primer with dNTPs, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus aPCR steps are denaturation, annealing and extension. The particulars of aPCR are well known, and include the use of a thermostable polymerase such as Taq I polymerase and thermal cycling.

Accordingly, the aPCR reaction requires at least one aPCR primer, a polymerase, and a set of dNTPs. As outlined herein, the primers may comprise the label, or one or more of the dNTPs may comprise a label.

Furthermore, the aPCR reaction may be run as a competition assay of sorts. For example, for biallelic SNPs, a first aPCR primer comprising a first base at the readout position and a first label, and a second aPCR primer comprising a different base at the readout position and a second label, may be used. The PCR primer for the other strand is the same. The examination of the ratio of the two colors can serve to identify the base at the detection position.

Allelic Primer Extension

In this embodiment allele specific primers when hybridized with their complementary target sequence serve as template for primer extension with a DNA polymerase. In some respects the method is similar to aPCR as described herein with the exception that only one primer need hybridize with the target sequence prior to amplification. That is, in contrast with PCR amplification that requires two primers, only one primer is necessary for amplification according to the method.

In a preferred embodiment, the primer is immobilized. In a preferred embodiment the primer is immobilized to microspheres or beads as described herein.

In general, as is more fully outlined below, the capture probes on the beads of the array are designed to be substantially complementary to the extended part of the primer; that is, unextended primers will not bind to the capture probes.

Ligation Techniques for Genotyping

In this embodiment, the readout of the base at the detection position proceeds using a ligase. In this embodiment, it is the specificity of the ligase which is the basis of the genotyping; that is, ligases generally require that the 5' and 3' ends of the ligation probes have perfect complementarity to the target for ligation to occur. Thus, in a preferred embodiment, the identity of the base at the detection position proceeds utilizing OLA as described above. The method can be run at least two different ways; in a first embodiment, only one strand of a target sequence is used as a template for ligation; alternatively, both strands may be used; the latter is generally referred to as Ligation Chain Reaction or LCR.

This method is based on the fact that two probes can be preferentially ligated together, if they are hybridized to a target strand and if perfect complementarity exists at the two bases being ligated together. Thus, in this embodiment, the target sequence comprises a contiguous first target domain comprising the detection position and a second target domain adjacent to the detection position. That is, the detection position is "between" the rest of the first target domain and the second target domain, or the detection position is one nucleotide from the 3' terminus of one of the ligation probes. A first ligation probe is hybridized to the first target domain and a second ligation probe is hybridized to the second target domain. If the first ligation probe has a base perfectly complementary to the detection position base, and the adjacent base on the second probe has perfect complementarity to its position, a ligation structure is formed such that the two probes can be ligated together to form a ligated probe. If this complementarity does not exist, no ligation structure is formed and the probes are not ligated together to an appreciable degree. This may be done using heat cycling, to allow the ligated probe to be denatured off the target sequence such that it may serve as a template for further reactions. In addition, as is more fully outlined below, this method may also be done using ligation probes that are separated by one or more nucleotides, if dNTPs and a polymerase are added (this is sometimes referred to as "Genetic Bit" analysis).

In a preferred embodiment, LCR is done for two strands of a double-stranded target sequence. The target sequence is denatured, and two sets of probes are added: one set as outlined above for one strand of the target, and a separate set (i.e. third and fourth primer probe nucleic acids) for the other strand of the target. In a preferred embodiment, the first and third probes will hybridize, and the second and fourth probes will hybridize, such that amplification can occur. That is, when the first and second probes have been attached, the ligated probe can now be used as a template, in addition to the second target sequence, for the attachment of the third and fourth probes. Similarly, the ligated third and fourth probes will serve as a template for the attachment of the first and second probes, in addition to the first target strand. In this way, an exponential, rather than just a linear, amplification can occur.

As will be appreciated by those in the art, the ligation product can be detected in a variety of ways.

Preferably, detection is accomplished by removing the unligated labeled probe from the reaction before application to a capture probe. In one embodiment, the unligated probes are removed by digesting 3' non-protected oligonucleotides with a 3' exonuclease, such as, exonuclease I. The ligation products are protected from exo I digestion by including, for example, the use of a number of sequential phosphorothioate residues at their 3' terminus (for example at least four), thereby, rendering them resistant to exonuclease digestion. The unligated detection oligonucleotides are not protected and are digested.

As for most or all of the methods described herein, the assay can take on a solution-based form or a solid-phase form.

Solution Based OLA

In a preferred embodiment, the ligation reaction is run in solution. In this embodiment, only one of the primers carries a detectable label, e.g. the first ligation probe, and the capture probe on the bead is substantially complementary to the other probe, e.g. the second ligation probe. In this way, unextended labeled ligation primers will not interfere with the assay. This substantially reduces or eliminates false signal generated by the optically-labeled 3' primers.

In addition, a solution-based OLA assay that utilizes adapter sequences may be done. In this embodiment, rather than have the target sequence comprise the adapter sequences, one of the ligation probes comprises the adapter sequence. This facilitates the creation of "universal arrays". For example, the first ligation probe has an adapter sequence that is used to attach the ligated probe to the array.

Again, as outlined above for SBE, unreacted ligation primers may be removed from the mixture as needed. For example, the first ligation probe may comprise the label (either a primary or secondary label) and the second may be blocked at its 3' end with an exonuclease blocking moiety; after ligation and the introduction of the nuclease, the labeled ligation probe will be digested, leaving the ligation product and the second probe; however, since the second probe is unlabeled, it is effectively silent in the assay. Similarly, the second probe may comprise a binding partner used to pull out the ligated probes, leaving unligated labeled ligation probes behind. The binding pair is then disassociated for subsequent amplification or detection.

Solid Phase Based OLA

Alternatively, the target nucleic acid is immobilized on a solid-phase surface. The OLA assay is performed and unligated oligonucleotides are removed by washing under appropriate stringency to remove unligated oligonucleotides and thus the label. For example, the capture probe can comprise one of the ligation probes.

Again, as outlined above, the detection of the OLA reaction can also occur directly, in the case where one or both of the primers comprises at least one detectable label, or indirectly, using sandwich assays, through the use of additional probes; that is, the ligated probes can serve as target sequences; and detection may utilize amplification probes, capture probes, capture extender probes, label probes, and label extender probes, etc. Alternatively, the OLA product is amplified. In a preferred embodiment the amplicons comprise labels.

In some embodiments target nucleic acids include both DNA and RNA. In a preferred embodiment RNA is mRNA. In some embodiments when RNA is the target nucleic acid, it is desirable to perform a reverse transcription assay prior to OLA as described herein. The reverse transcription assay results in the formation of cDNA. This method is particularly advantageous in determining either gene expression levels or genotyping, or both. That is, the cDNA is representative of the level of mRNA. Accordingly, gene expression analysis is performed. In addition, the cDNA also serves as a template for OLA which allows for genotyping. Thus, the use of both DNA and/or RNA allows for increased multiplexing of samples on an array.

Solid Phase Oligonucleotide Ligation Assay (SPOLA)

In a preferred embodiment, a novel method of OLA is used, termed herein "solid phase oligonucleotide assay", or "SPOLA". In this embodiment, the ligation probes are both attached to the same site on the surface of the array (e.g. when microsphere arrays are used, to the same bead), one at its 5' end (the "upstream probe") and one at its 3' end (the "downstream probe"). This may be done as is will be appreciated by those in the art. At least one of the probes is attached via a cleavable linker, that upon cleavage, forms a reactive or detectable (fluorophore) moiety. If ligation occurs, the reactive moiety remains associated with the surface; but if no ligation occurs, due to a mismatch, the reactive moiety is free in solution to diffuse away from the surface of the array. The reactive moiety is then used to add a detectable label.

Generally, as will be appreciated by those in the art, cleavage of the cleavable linker should result in asymmetrical products; i.e. one of the "ends" should be reactive, and the other should not, with the configuration of the system such that the reactive moiety remains associated with the surface if ligation occurred. Thus, for example, amino acids or succinate esters can be cleaved either enzymatically (via peptidases (aminopeptidase and carboxypeptidase) or proteases) or chemically (acid/base hydrolysis) to produce an amine and a carboxyl group. One of these groups can then be used to add a detectable label, as will be appreciated by those in the art and discussed herein.

Padlock Probe Ligation

In a preferred embodiment, the ligation probes are specialized probes called "padlock probes". Nilsson et al, 1994, Science 265:2085, hereby incorporated by reference. These probes have a first ligation domain that is identical to a first ligation probe, in that it hybridizes to a first target sequence domain, and a second ligation domain, identical to the second ligation probe, that hybridizes to an adjacent target sequence domain. Again, as for OLA, the detection position can be either at the 3' end of the first ligation domain or at the 5' end of the second ligation domain. However, the two ligation domains are connected by a linker, frequently nucleic acid. The configuration of the system is such that upon ligation of the first and second ligation domains of the padlock probe, the probe forms a circular probe, and forms a complex with the target sequence wherein the target sequence is "inserted" into the loop of the circle.

In this embodiment, the unligated probes may be removed through degradation (for example, through a nuclease), as there are no "free ends" in the ligated probe.

Cleavage Techniques for Genotyping

In a preferred embodiment, the specificity for genotyping is provided by a cleavage enzyme. There are a variety of enzymes known to cleave at specific sites, either based on sequence specificity, such as restriction endonucleases, or using structural specificity, such as is done through the use of invasive cleavage technology.

Endonuclease Techniques

In a preferred embodiment, enzymes that rely on sequence specificity are used. In general, these systems rely on the cleavage of double stranded sequence containing a specific sequence recognized by a nuclease, preferably an endonuclease including resolvases.

These systems may work in a variety of ways. In one embodiment, a labeled readout probe (generally attached to a bead of the array) is used; the binding of the target sequence forms a double stranded sequence that a restriction endonuclease can then recognize and cleave, if the correct sequence is present. The cleavage results in the loss of the label, and thus a loss of signal.

Alternatively, as will be appreciated by those in the art, a labelled target sequence may be used as well; for example, a labelled primer may be used in the PCR amplification of the target, such that the label is incorporated in such a manner as to be cleaved off by the enzyme.

Alternatively, the readout probe (or, again, the target sequence) may comprise both a fluorescent label and a quencher, as is known in the art. In this embodiment, the label and the quencher are attached to different nucleosides, yet are close enough that the quencher molecule results in little or no signal being present. Upon the introduction of the enzyme, the quencher is cleaved off, leaving the label, and allowing signaling by the label.

In addition, as will be appreciated by those in the art, these systems can be both solution-based assays or solid-phase assays, as outlined herein.

Furthermore, there are some systems that do not require cleavage for detection; for example, some nucleic acid binding proteins will bind to specific sequences and can thus serve as a secondary label. For example, some transcription factors will bind in a highly sequence dependent manner, and can distinguish between two SNPs. Having bound to the hybridization complex, a detectable binding partner can be added for detection. In addition, mismatch binding proteins based on mutated transcription factors can be used.

In addition, as will be appreciated by those in the art, this type of approach works with other cleavage methods as well, for example the use of invasive cleavage methods, as outlined below.

Invasive Cleavage

In a preferred embodiment, the determination of the identity of the base at the detection position of the target sequence proceeds using invasive cleavage technology. As outlined above for amplification, invasive cleavage techniques rely on the use of structure-specific nucleases, where the structure can be formed as a result of the presence or absence of a mismatch. Generally, invasive cleavage technology may be described as follows. A target nucleic acid is recognized by two distinct probes. A first probe, generally referred to herein as an "invader" probe, is substantially complementary to a first portion of the target nucleic acid. A second probe, generally referred to herein as a "signal probe", is partially complementary to the target nucleic acid; the 3' end of the signal oligonucleotide is substantially complementary to the target sequence while the 5' end is non-complementary and preferably forms a single-stranded "tail" or "arm". The non-complementary end of the second probe preferably comprises a "generic" or "unique" sequence, frequently referred to herein as a "detection sequence", that is used to indicate the presence or absence of the target nucleic acid, as described below. The detection sequence of the second probe preferably comprises at least one detectable label. Alternative methods have the detection sequence functioning as a target sequence for a capture probe, and thus rely on sandwich configurations using label probes.

Hybridization of the first and second oligonucleotides near or adjacent to one another on the target nucleic acid forms a number of structures. In a preferred embodiment, a forked cleavage structure forms and is a substrate of a nuclease which cleaves the detection sequence from the signal oligonucleotide. The site of cleavage is controlled by the distance or overlap between the 3' end of the invader oligonucleotide and the downstream fork of the signal oligonucleotide. Therefore, neither oligonucleotide is subject to cleavage when misaligned or when unattached to target nucleic acid.

As above, the invasive cleavage assay is preferably performed on an array format. In a preferred embodiment, the signal probe has a detectable label, attached 5' from the site of nuclease cleavage (e.g. within the detection sequence) and a capture tag, as described herein for removal of the unreacted products (e.g. biotin or other hapten) 3' from the site of nuclease cleavage. After the assay is carried out, the uncleaved probe and the 3' portion of the cleaved signal probe (e.g. the detection sequence) may be extracted, for example, by binding to streptavidin beads or by crosslinking through the capture tag to produce aggregates or by antibody to an attached hapten. By "capture tag" herein is a meant one of a pair of binding partners as described above, such as antigen/antibody pairs, digoxygenenin, dinitrophenol, etc.

The cleaved 5' region, e.g. the detection sequence, of the signal probe, comprises a label and is detected and optionally quantitated. In one embodiment, the cleaved 5' region is hybridized to a probe on an array (capture probe) and optically detected. As described below, many different signal probes can be analyzed in parallel by hybridization to their complementary probes in an array. In a preferred embodiment, combination techniques are used to obtain higher specificity and reduce the detection of contaminating uncleaved signal probe or incorrectly cleaved product, an enzymatic recognition step is introduced in the array capture procedure. For example, as more fully outlined below, the cleaved signal probe binds to a capture probe to produce a double-stranded nucleic acid in the array. In this embodiment, the 3' end of the cleaved signal probe is adjacent to the 5' end of one strand of the capture probe, thereby, forming a substrate for DNA ligase (Broude et al. 1991. PNAS 91: 3072-3076). Only correctly cleaved product is ligated to the capture probe. Other incorrectly hybridized and non-cleaved signal probes are removed, for example, by heat denaturation, high stringency washes, and other methods that disrupt base pairing.

Accordingly, the present invention provides methods of determining the identity of a base at the detection position of a target sequence. In this embodiment, the target sequence comprises, 5' to 3', a first target domain comprising an overlap domain comprising at least a nucleotide in the detection position, and a second target domain contiguous with the detection position. A first probe (the "invader probe") is hybridized to the first target domain of the target sequence. A second probe (the "signal probe"), comprising a first portion that hybridizes to the second target domain of the target sequence and a second portion that does not hybridize to the target sequence, is hybridized to the second target domain. If the second probe comprises a base that is perfectly complementary to the detection position a cleavage structure is formed. The addition of a cleavage enzyme, such as is described in U.S. Pat. Nos. 5,846,717; 5,614,402; 5,719,029; 5,541,311 and 5,843,669, all of which are expressly incorporated by reference, results in the cleavage of the detection sequence from the signaling probe. This then can be used as a target sequence in an assay complex.

In addition, as for a variety of the techniques outlined herein, unreacted probes (i.e. signaling probes, in the case of invasive cleavage), may be removed using any number of techniques. For example, the use of a binding partner coupled to a solid support comprising the other member of the binding pair can be done. Similarly, after cleavage of the primary signal probe, the newly created cleavage products can be selectively labeled at the 3' or 5' ends using enzymatic or chemical methods.

Again, as outlined above, the detection of the invasive cleavage reaction can occur directly, in the case where the detection sequence comprises at least one label, or indirectly, using sandwich assays, through the use of additional probes; that is, the detection sequences can serve as target sequences, and detection may utilize amplification probes, capture probes, capture extender probes, label probes, and label extender probes, etc.

In addition, as for most of the techniques outlined herein, these techniques may be done for the two strands of a double-stranded target sequence. The target sequence is denatured, and two sets of probes are added: one set as outlined above for one strand of the target, and a separate set for the other strand of the target.

Thus, the invasive cleavage reaction requires, in no particular order, an invader probe, a signaling probe, and a cleavage enzyme.

As for other methods outlined herein, the invasive cleavage reaction may be done as a solution based assay or a solid phase assay.

Solution-Based Invasive Cleavage

The invasive cleavage reaction may be done in solution, followed by addition of one of the components to an array, with optional (but preferable) removal of unreacted probes. For example, the reaction is carried out in solution, using a capture tag (i.e. a member of a binding partner pair) that is separated from the label on the detection sequence with the cleavage site. After cleavage (dependent on the base at the detection position), the signaling probe is cleaved. The capture tag is used to remove the uncleaved probes (for example, using magnetic particles comprising the other member of the binding pair), and the remaining solution is added to the array. The detection sequence can be directly attached to the capture probe. In this embodiment, the detection sequence can effectively act as an adapter sequence. In alternate embodiments, the detection sequence is unlabelled and an additional label probe is used; as outlined below, this can be ligated to the hybridization complex.

Solid-Phase Based Assays

The invasive cleavage reaction can also be done as a solid-phase assay. The target sequence can be attached to the array using a capture probe (in addition, although not shown, the target sequence may be directly attached to the array). In a preferred embodiment, the signaling probe comprises both a fluorophore label (attached to the portion of the signaling probe that hybridizes to the target) and a quencher (generally on the detection sequence), with a cleavage site in between. Thus, in the absence of cleavage, very little signal is seen due to the quenching reaction. After cleavage, however, the detection sequence is removed, along with the quencher, leaving the unquenched fluorophore. Similarly, the invasive probe may be attached to the array.

In a preferred embodiment, the invasive cleavage reaction is configured to utilize a fluorophore-quencher reaction. A signaling probe comprising both a fluorophore and a quencher is attached to the bead. The fluorophore is contained on the portion of the signaling probe that hybridizes to the target sequence, and the quencher is contained on a portion of the signaling probe that is on the other side of the cleavage site (termed the "detection sequence" herein). In a preferred embodiment, it is the 3' end of the signaling probe that is attached to the bead (although as will be appreciated by those in the art, the system can be configured in a variety of different ways, including methods that would result in a loss of signal upon cleavage). Thus, the quencher molecule is located 5' to the cleavage site. Upon assembly of an assay complex, comprising the target sequence, an invader probe, and a signaling probe, and the introduction of the cleavage enzyme, the cleavage of the complex results in the disassociation of the quencher from the complex, resulting in an increase in fluorescence.

In this embodiment, suitable fluorophore-quencher pairs are as known in the art. For example, suitable quencher molecules comprise Dabcyl.

Redundant Genotyping

In a preferred embodiment, the invention provides a method of increasing the confidence of genotyping results. The method includes performing genotyping more than once on a particular target sequence. That is, a sample or target analyte is genotyped at least twice. Preferably, the sample is genotyped with different techniques such as Invader™ and OLA as described herein. If the results of the individual genotyping assays agree, then confidence that the genotyping results are correct is increased.

Amplification Reactions

In this embodiment, the invention provides compositions and methods for amplification and/or detection (and optionally quantification) of products of nucleic acid amplification reactions. Suitable amplification methods include both target amplification and signal amplification. Target amplification involves the amplification (i.e. replication) of the target sequence to be detected, resulting in a significant increase in the number of target molecules. Target amplification strategies include but are not limited to the polymerase chain reaction (PCR), strand displacement amplification (SDA), and nucleic acid sequence based amplification (NASBA).

Alternatively, rather than amplify the target, alternate techniques use the target as a template to replicate a signaling probe, allowing a small number of target molecules to result in a large number of signaling probes, that then can be detected. Signal amplification strategies include the ligase chain reaction (LCR), cycling probe technology (CPT), invasive cleavage techniques such as Invader™ technology, Q-Beta replicase (QβR) technology, and the use of "amplification probes" such as "branched DNA" that result in multiple label probes binding to a single target sequence.

All of these methods require a primer nucleic acid (including nucleic acid analogs) that is hybridized to a target sequence to form a hybridization complex, and an enzyme is added that in some way modifies the primer to form a modified primer. For example, PCR generally requires two primers, dNTPs and a DNA polymerase; LCR requires two primers that adjacently hybridize to the target sequence and a ligase; CPT requires one cleavable primer and a cleaving enzyme; invasive cleavage requires two primers and a cleavage enzyme; etc. Thus, in general, a target nucleic acid is added to a reaction mixture that comprises the necessary amplification components, and a modified primer is formed.

In general, the modified primer comprises a detectable label, such as a fluorescent label, which is either incorporated by the enzyme or present on the original primer. As required, the unreacted primers are removed, in a variety of ways, as will be appreciated by those in the art and outlined herein. The hybridization complex is then disassociated, and the modified primer is detected and optionally quantitated by a microsphere array. In some cases, the newly modified primer serves as a target sequence for a secondary reaction, which then produces a number of amplified strands, which can be detected as outlined herein.

Accordingly, the reaction starts with the addition of a primer nucleic acid to the target sequence which forms a hybridization complex. Once the hybridization complex between the primer and the target sequence has been formed, an enzyme, sometimes termed an "amplification enzyme", is used to modify the primer. As for all the methods outlined herein, the enzymes may be added at any point during the assay, either prior to, during, or after the addition of the primers. The identity of the enzyme will depend on the amplification technique used, as is more fully outlined below. Similarly, the modification will depend on the amplification technique, as outlined below.

Once the enzyme has modified the primer to form a modified primer, the hybridization complex is disassociated. In one aspect, dissociation is by modification of the assay conditions. In another aspect, the modified primer no longer hybridizes to the target nucleic acid and dissociates. Either one or both of these aspects can be employed in signal and target amplification reactions as described below. Generally, the amplification steps are repeated for a period of time to allow a number of cycles, depending on the number of copies of the original target sequence and the sensitivity of detection, with cycles ranging from 1 to thousands, with from 10 to 100 cycles being preferred and from 20 to 50 cycles being especially preferred. When linear strand displacement amplification is used cycle numbers can reach thousands to millions.

After a suitable time of amplification, unreacted primers are removed, in a variety of ways, as will be appreciated by those in the art and described below, and the hybridization complex is disassociated. In general, the modified primer comprises a detectable label, such as a fluorescent label, which is either incorporated by the enzyme or present on the original primer, and the modified primer is detected by any of the methods as known to the skilled artisan and include but are not limited to the methods described herein Target Amplification In a preferred embodiment, the amplification is target amplification. Target amplification involves the amplification (replication) of the target sequence to be detected, such that the number of copies of the target sequence is increased. Suitable target amplification techniques include, but are not limited to, the polymerase chain reaction (PCR), strand displacement amplification (SDA), transcription mediated amplification (TMA) and nucleic acid sequence based amplification (NASBA).

Polymerase Chain Reaction Amplification

In a preferred embodiment, the target amplification technique is PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR", "panhandle PCR", and "PCR select cDNA subtraction", "allele-specific PCR", among others. In some embodiments, PCR is not preferred.

In general, PCR may be briefly described as follows. A double stranded target nucleic acid is denatured, generally by raising the temperature, and then cooled in the presence of an excess of a PCR primer, which then hybridizes to the first target strand. A DNA polymerase then acts to extend the primer with dNTPs, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus PCR steps are denaturation, annealing and extension. The particulars of PCR are well known, and include the use of a thermostable polymerase such as Taq I polymerase and thermal cycling.

Accordingly, the PCR reaction requires at least one PCR primer, a polymerase, and a set of dNTPs. As outlined herein, the primers may comprise the label, or one or more of the dNTPs may comprise a label.

In one embodiment asymmetric PCR is performed. In this embodiment, unequal concentrations of primers are included in the amplification reaction. The concentrations are designed such that one primer is in excess or is saturating, while the other primer is limiting or is at a sub-saturating concentration.

In one embodiment, PCR primers for amplification of a plurality of target nucleic acids are immobilized on a single bead. That is, at least first and second PCR primer pairs are immobilized to a bead or microsphere. The microsphere is contacted with a sample and PCR performed as described herein. Detection of the amplified product or products is accomplished by any of the detection methods described herein, but in a preferred embodiment, detection proceeds by hybridization with allele specific oligonucleotides. That is, upon amplification of the target nucleotides, the immobilized PCR product is hybridized with oligonucleotides that are complementary to the amplified product.

In a preferred embodiment the allele specific oligonucleotides contain discrete labels. That is, the oligonucleotides contain distinguishable labels. As a result of hybridization between the allele specific oligonucleotides and the amplified product(s), detection of a particular label provides an indication of the presence of a particular target nucleic acid in the sample.

In one embodiment, the PCR primers are designed to amplify different genomic markers. That is, markers such as translocations or other chromosomal abnormalities are targeted for amplification. In an additional embodiment, the primers are designed to amplify genomic regions containing single nucleotide polymorphisms (SNPs). As such, the resulting hybridization with allele specific oligonucleotides provides an indication of the marker or SNP. In one embodiment, a plurality of markers or SNPs is detected on each bead. That is, at least two markers or SNPs are detected on each bead.

In general, as is more fully outlined below, the capture probes on the beads of the array are designed to be substantially complementary to the extended part of the primer; that is, unextended primers will not bind to the capture probes.

Alternatively, as further described below, unreacted probes may be removed prior to addition to the array.

In a preferred embodiment the amplification reaction as a multiplex amplification reaction as described herein. In one embodiment the amplification reaction uses a plurality of PCR primers to amplify a plurality of target sequences. In this embodiment plurality of target sequences are simultaneously amplified with the plurality of amplification primer pairs.

An alternative embodiment the multiplex PCR reaction uses universal primers as described herein. That is, universal PCR primers hybridized to universal priming sites on the target sequence and thereby amplify a plurality of target sequences. This embodiment is potentially preferred because it requires only a limited number of PCR primers. That is, as few as one primer pairs can amplify a plurality of target sequences.

Strand Displacement Amplification (SDA)

In a preferred embodiment, the target amplification technique is SDA. Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby expressly incorporated by reference in their entirety.

In general, SDA may be described as follows. A single stranded target nucleic acid, usually a DNA target sequence, is contacted with an SDA primer. An "SDA primer" generally has a length of 25-100 nucleotides, with SDA primers of approximately 35 nucleotides being preferred. An SDA primer is substantially complementary to a region at the 3' end of the target sequence, and the primer has a sequence at its 5' end (outside of the region that is complementary to the target) that is a recognition sequence for a restriction endonuclease, sometimes referred to herein as a "nicking enzyme" or a "nicking endonuclease", as outlined below. The SDA primer then hybridizes to the target sequence. The SDA reaction mixture also contains a polymerase (an "SDA polymerase", as outlined below) and a mixture of all four deoxynucleoside-triphosphates (also called deoxynucleotides or dNTPs, i.e. dATP, dTTP, dCTP and dGTP), at least one species of which is a substituted or modified dNTP; thus, the SDA primer is modified, i.e. extended, to form a modified primer, sometimes referred to herein as a "newly synthesized strand". The substituted dNTP is modified such that it will inhibit cleavage in the strand containing the substituted dNTP but will not inhibit cleavage on the other strand. Examples of suitable substituted dNTPs include, but are not limited, 2' deoxyadenosine 5'-O-(1-thiotriphosphate), 5-methyldeoxycytidine 5'-triphosphate, 2'-deoxyuridine 5'-triphosphate, and 7-deaza-2'-deoxyguanosine 5'-triphosphate. In addition, the substitution of the dNTP may occur after incorporation into a newly synthesized strand; for example, a methylase may be used to add methyl groups to the synthesized strand. In addition, if all the nucleotides are substituted, the polymerase may have 5'→3' exonuclease activity. However, if less than all the nucleotides are substituted, the polymerase preferably lacks 5'→3' exonuclease activity.

As will be appreciated by those in the art, the recognition site/endonuclease pair can be any of a wide variety of known combinations. The endonuclease is chosen to cleave a strand either at the recognition site, or either 3' or 5' to it, without cleaving the complementary sequence, either because the enzyme only cleaves one strand or because of the incorporation of the substituted nucleotides. Suitable recognition site/endonuclease pairs are well known in the art; suitable endonucleases include, but are not limited to, HincII, HindII, AvaI, Fnu4HI, TthIIII, NcII, BstXI, BamHI, etc. A chart depicting suitable enzymes, and their corresponding recognition sites and the modified dNTP to use is found in U.S. Pat. No. 5,455,166, hereby expressly incorporated by reference.

Once nicked, a polymerase (an "SDA polymerase") is used to extend the newly nicked strand, 5'→3', thereby creating another newly synthesized strand. The polymerase chosen should be able to initiate 5'→3' polymerization at a nick site, should also displace the polymerized strand downstream from the nick, and should lack 5'→3' exonuclease activity (this may be additionally accomplished by the addition of a blocking agent). Thus, suitable polymerases in SDA include, but are not limited to, the Klenow fragment of DNA polymerase I, SEQUENASE 1.0 and SEQUENASE 2.0 (U.S. Biochemical), T5 DNA polymerase and Phi29 DNA polymerase.

Accordingly, the SDA reaction requires, in no particular order, an SDA primer, an SDA polymerase, a nicking endonuclease, and dNTPs, at least one species of which is modified. Again, as outlined above for PCR, preferred embodiments utilize capture probes complementary to the newly synthesized portion of the primer, rather than the primer region, to allow unextended primers to be removed.

In general, SDA does not require thermocycling. The temperature of the reaction is generally set to be high enough to prevent non-specific hybridization but low enough to allow specific hybridization; this is generally from about 37° C. to about 42° C., depending on the enzymes.

In a preferred embodiment, as for most of the amplification techniques described herein, a second amplification reaction can be done using the complementary target sequence, resulting in a substantial increase in amplification during a set period of time. That is, a second primer nucleic acid is hybridized to a second target sequence, that is substantially complementary to the first target sequence, to form a second hybridization complex. The addition of the enzyme, followed by disassociation of the second hybridization complex, results in the generation of a number of newly synthesized second strands.

Nucleic Acid Sequence Based Amplification (NASBA) and Transcription Mediated Amplification (TMA)

In a preferred embodiment, the target amplification technique is nucleic acid sequence based amplification (NASBA). NASBA is generally described in U.S. Pat. No. 5,409,818; Sooknanan et al., Nucleic Acid Sequence-Based Amplification, Ch. 12 (pp. 261-285) of Molecular Methods for Virus Detection, Academic Press, 1995; and "Profiting from Gene-based Diagnostics", CTB International Publishing Inc., N.J., 1996, all of which are incorporated by reference. NASBA is very similar to both TMA and QBR. Transcription mediated amplification (TMA) is generally described in U.S. Pat. Nos. 5,399,491, 5,888,779, 5,705,365, 5,710,029, all of which are incorporated by reference. The main difference between NASBA and TMA is that NASBA utilizes the addition of RNAse H to effect RNA degradation, and TMA relies on inherent RNAse H activity of the reverse transcriptase.

In general, these techniques may be described as follows. A single stranded target nucleic acid, usually an RNA target sequence (sometimes referred to herein as "the first target sequence" or "the first template"), is contacted with a first primer, generally referred to herein as a "NASBA primer" (although "TMA primer" is also suitable). Starting with a DNA target sequence is described below. These primers generally have a length of 25-100 nucleotides, with NASBA primers of approximately 50-75 nucleotides being preferred.

The first primer is preferably a DNA primer that has at its 3' end a sequence that is substantially complementary to the 3' end of the first template. The first primer also has an RNA polymerase promoter at its 5' end (or its complement (antisense), depending on the configuration of the system). The first primer is then hybridized to the first template to form a first hybridization complex. The reaction mixture also includes a reverse transcriptase enzyme (an "NASBA reverse transcriptase") and a mixture of the four dNTPs, such that the first NASBA primer is modified, i.e. extended, to form a modified first primer, comprising a hybridization complex of RNA (the first template) and DNA (the newly synthesized strand).

By "reverse transcriptase" or "RNA-directed DNA polymerase" herein is meant an enzyme capable of synthesizing DNA from a DNA primer and an RNA template. Suitable RNA-directed DNA polymerases include, but are not limited to, avian myloblastosis virus reverse transcriptase ("AMY RT") and the Moloney murine leukemia virus RT. When the amplification reaction is TMA, the reverse transcriptase enzyme further comprises a RNA degrading activity as outlined below.

In addition to the components listed above, the NASBA reaction also includes an RNA degrading enzyme, also sometimes referred to herein as a ribonuclease, that will hydrolyze RNA of an RNA:DNA hybrid without hydrolyzing single- or double-stranded RNA or DNA. Suitable ribonucleases include, but are not limited to, RNase H from *E. coli* and calf *thymus*.

The ribonuclease activity degrades the first RNA template in the hybridization complex, resulting in a disassociation of the hybridization complex leaving a first single stranded newly synthesized DNA strand, sometimes referred to herein as "the second template".

In addition, the NASBA reaction also includes a second NASBA primer, generally comprising DNA (although as for all the probes herein, including primers, nucleic acid analogs may also be used). This second NASBA primer has a sequence at its 3' end that is substantially complementary to the 3' end of the second template, and also contains an antisense sequence for a functional promoter and the antisense sequence of a transcription initiation site. Thus, this primer sequence, when used as a template for synthesis of the third DNA template, contains sufficient information to allow specific and efficient binding of an RNA polymerase and initiation of transcription at the desired site. Preferred embodiments utilizes the antisense promoter and transcription initiation site are that of the T7 RNA polymerase, although other RNA polymerase promoters and initiation sites can be used as well, as outlined below.

The second primer hybridizes to the second template, and a DNA polymerase, also termed a "DNA-directed DNA polymerase", also present in the reaction, synthesizes a third template (a second newly synthesized DNA strand), resulting in second hybridization complex comprising two newly synthesized DNA strands.

Finally, the inclusion of an RNA polymerase and the required four ribonucleoside triphosphates (ribonucleotides or NTPs) results in the synthesis of an RNA strand (a third newly synthesized strand that is essentially the same as the first template). The RNA polymerase, sometimes referred to herein as a "DNA-directed RNA polymerase", recognizes the promoter and specifically initiates RNA synthesis at the initiation site. In addition, the RNA polymerase preferably synthesizes several copies of RNA per DNA duplex. Preferred RNA polymerases include, but are not limited to, T7 RNA polymerase, and other bacteriophage RNA polymerases including those of phage T3, phage ϕII, *Salmonella* phage sp6, or Pseudomonase phage gh-1.

In some embodiments, TMA and NASBA are used with starting DNA target sequences. In this embodiment, it is necessary to utilize the first primer comprising the RNA polymerase promoter and a DNA polymerase enzyme to generate a double stranded DNA hybrid with the newly synthesized strand comprising the promoter sequence. The hybrid is then denatured and the second primer added.

Accordingly, the NASBA reaction requires, in no particular order, a first NASBA primer, a second NASBA primer comprising an antisense sequence of an RNA polymerase promoter, an RNA polymerase that recognizes the promoter, a reverse transcriptase, a DNA polymerase, an RNA degrading enzyme, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

Accordingly, the TMA reaction requires, in no particular order, a first TMA primer, a second TMA primer comprising an antisense sequence of an RNA polymerase promoter, an RNA polymerase that recognizes the promoter, a reverse transcriptase with RNA degrading activity, a DNA polymerase, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

As outlined herein, the detection of the newly synthesized strands can proceed in several ways. Direct detection can be done when the newly synthesized strands comprise detectable labels, either by incorporation into the primers or by incorporation of modified labelled nucleotides into the growing strand. Alternatively, as is more fully outlined below, indirect detection of unlabelled strands (which now serve as "targets" in the detection mode) can occur using a variety of sandwich assay configurations. As will be appreciated by those in the art, any of the newly synthesized strands can serve as the "target" for form an assay complex on a surface with a capture probe. In NASBA and TMA, it is preferable to utilize the newly formed RNA strands as the target, as this is where significant amplification occurs.

In this way, a number of secondary target molecules are made. As is more fully outlined below, these reactions (that is, the products of these reactions) can be detected in a number of ways.

Rolling-Circle Amplification (RCA)

In a preferred embodiment the signal amplification technique is RCA. Rolling-circle amplification is generally described in Baner et al. (1998) *Nuc. Acids Res.* 26:5073-5078; Barany, F. (1991) *Proc. Natl. Acad. Sci. USA* 88:189-193; and Lizardi et al. (1998) *Nat. Genet.* 19:225-232, all of which are incorporated by reference in their entirety.

In general, RCA may be described in two ways. First, as is outlined in more detail below, a single probe is hybridized with a target nucleic acid. Each terminus of the probe hybridizes adjacently on the target nucleic acid and the OLA assay as described above occurs. Alternatively, two probes are hybridized with the target nucleic acid and the OLA assay as described above occurs. When ligated, the probe is circularized while hybridized to the target nucleic acid, or a circular primer is added to the ligated target nucleic acid complex. Addition of a polymerase results in extension of the circular probe. However, since the probe has no terminus, the polymerase continues to extend the probe repeatedly. Thus results in amplification of the circular probe.

A second alternative approach involves OLA followed by RCA. In this embodiment, an immobilized primer is contacted with a target nucleic acid. Complementary sequences will hybridize with each other resulting in an immobilized duplex. A second primer is contacted with the target nucleic acid. The second primer hybridizes to the target nucleic acid adjacent to the first primer. An OLA assay is performed as described above. Ligation only occurs if the primer are complementary to the target nucleic acid. When a mismatch occurs, particularly at one of the nucleotides to be ligated, ligation will not occur. Following ligation of the oligonucleotides, the ligated, immobilized, oligonucleotide is then hybridized with an RCA probe. This is a circular probe that is designed to specifically hybridize with the ligated oligonucleotide and will only hybridize with an oligonucleotide that has undergone ligation. RCA is then performed as is outlined in more detail below.

Accordingly, in an preferred embodiment, a single oligonucleotide is used both for OLA and as the circular template for RCA (referred to herein as a "padlock probe" or a "RCA probe"). That is, each terminus of the oligonucleotide contains sequence complementary to the target nucleic acid and functions as an OLA primer as described above. That is, the first end of the RCA probe is substantially complementary to a first target domain, and the second end of the RCA probe is substantially complementary to a second target domain, adjacent to the first domain. Hybridization of the oligonucleotide to the target nucleic acid results in the formation of a hybridization complex. Ligation of the "primers" (which are the discrete ends of a single oligonucleotide) results in the formation of a modified hybridization complex containing a circular probe i.e. an RCA template complex. That is, the oligonucleotide is circularized while still hybridized with the target nucleic acid. This serves as a circular template for RCA. Addition of a polymerase to the RCA template complex results in the formation of an amplified product nucleic acid. Following RCA, the amplified product nucleic acid is detected. This can be accomplished in a variety of ways; for example, the polymerase may incorporate labeled nucleotides, or alternatively, a label probe is used that is substantially complementary to a portion of the RCA probe and comprises at least one label is used.

The polymerase can be any polymerase, but is preferably one lacking 3' exonuclease activity (3' exo⁻). Examples of suitable polymerase include but are not limited to exonuclease minus DNA Polymerase I large (Klenow) Fragment, Phi29 DNA polymerase, Taq DNA Polymerase and the like. In addition, in some embodiments, a polymerase that will replicate single-stranded DNA (i.e. without a primer forming a double stranded section) can be used.

In a preferred embodiment, the RCA probe contains an adapter sequence as outlined herein, with adapter capture probes on the array, for example on a microsphere when microsphere arrays are being used. Alternatively, unique portions of the RCA probes, for example all or part of the sequence corresponding to the target sequence, can be used to bind to a capture probe.

In a preferred embodiment, the padlock probe contains a restriction site. The restriction endonuclease site allows for cleavage of the long concatamers that are typically the result of RCA into smaller individual units that hybridize either more efficiently or faster to surface bound capture probes. Thus, following RCA, the product nucleic acid is contacted with the appropriate restriction endonuclease. This results in cleavage of the product nucleic acid into smaller fragments. The fragments are then hybridized with the capture probe that is immobilized resulting in a concentration of product fragments onto the microsphere. Again, as outlined herein, these fragments can be detected in one of two ways: either labelled nucleotides are incorporated during the replication step, or an additional label probe is added.

Thus, in a preferred embodiment, the padlock probe comprises a label sequence; i.e. a sequence that can be used to bind label probes and is substantially complementary to a label probe. In one embodiment, it is possible to use the same label sequence and label probe for all padlock probes on an array; alternatively, each padlock probe can have a different label sequence.

The padlock probe also contains a priming site for priming the RCA reaction. That is, each padlock probe comprises a sequence to which a primer nucleic acid hybridizes forming a template for the polymerase. The primer can be found in any portion of the circular probe. In a preferred embodiment, the primer is located at a discrete site in the probe. In this embodiment, the primer site in each distinct padlock probe is identical, although this is not required. Advantages of using primer sites with identical sequences include the ability to use only a single primer oligonucleotide to prime the RCA assay with a plurality of different hybridization complexes. That is, the padlock probe hybridizes uniquely to the target nucleic acid to which it is designed. A single primer hybridizes to all of the unique hybridization complexes forming a priming site for the polymerase. RCA then proceeds from an identical locus within each unique padlock probe of the hybridization complexes.

In an alternative embodiment, the primer site can overlap, encompass, or reside within any of the above-described elements of the padlock probe. That is, the primer can be found, for example, overlapping or within the restriction site or the identifier sequence. In this embodiment, it is necessary that the primer nucleic acid is designed to base pair with the chosen primer site.

Thus, the padlock probe of the invention contains at each terminus, sequences corresponding to OLA primers. The intervening sequence of the padlock probe contain in no particular order, an adapter sequence and a restriction endonuclease site. In addition, the padlock probe contains a RCA priming site.

Thus, in a preferred embodiment the OLA/RCA is performed in solution followed by restriction endonuclease cleavage of the RCA product. The cleaved product is then applied to an array comprising beads, each bead comprising a probe complementary to the adapter sequence located in the padlock probe. The amplified adapter sequence correlates with a particular target nucleic acid. Thus the incorporation of an endonuclease site allows the generation of short, easily hybridizable sequences. Furthermore, the unique adapter sequence in each rolling circle padlock probe sequence allows diverse sets of nucleic acid sequences to be analyzed in parallel on an array, since each sequence is resolved on the basis of hybridization specificity.

In an alternative OLA/RCA method, one of the OLA primers is immobilized on the microsphere; the second primer is added in solution. Both primers hybridize with the target nucleic acid forming a hybridization complex as described above for the OLA assay.

As described herein, the microsphere is distributed on an array. In a preferred embodiment, a plurality of microspheres each with a unique OLA primer is distributed on the array.

Following the OLA assay, and either before, after or concurrently with distribution of the beads on the array, a segment of circular DNA is hybridized to the bead-based ligated oligonucleotide forming a modified hybridization complex. Addition of an appropriate polymerase (3' exo⁻), as is known in the art, and corresponding reaction buffer to the array leads to amplification of the circular DNA. Since there is no terminus to the circular DNA, the polymerase continues to travel around the circular template generating extension product until it detaches from the template. Thus, a polymerase with high processivity can create several hundred or thousand copies of the circular template with all the copies linked in one contiguous strand.

Again, these copies are subsequently detected by one of two methods; either hybridizing a labeled oligo complementary to the circular target or via the incorporation of labeled nucleotides in the amplification reaction. The label is detected using conventional label detection methods as described herein.

In one embodiment, when the circular DNA contains sequences complementary to the ligated oligonucleotide it is preferable to remove the target DNA prior to contacting the ligated oligonucleotide with the circular DNA (See FIG. 7). This is done by denaturing the double-stranded DNA by methods known in the art. In an alternative embodiment, the double stranded DNA is not denatured prior to contacting the circular DNA.

In an alternative embodiment, when the circular DNA contains sequences complementary to the target nucleic acid, it is preferable that the circular DNA is complementary at a site distinct from the site bound to the ligated oligonucleotide. In this embodiment it is preferred that the duplex between the ligated oligonucleotide and target nucleic acid is not denatured or disrupted prior to the addition of the circular DNA so that the target DNA remains immobilized to the bead.

Hybridization and washing conditions are well known in the art; various degrees of stringency can be used. In some embodiments it is not necessary to use stringent hybridization or washing conditions as only microspheres containing the ligated probes will effectively hybridize with the circular DNA; microspheres bound to DNA that did not undergo ligation (those without the appropriate target nucleic acid) will not hybridize as strongly with the circular DNA as those primers that were ligated. Thus, hybridization and/or washing conditions are used that discriminate between binding of the circular DNA to the ligated primer and the unligated primer.

Alternatively, when the circular probe is designed to hybridize to the target nucleic acid at a site distinct from the site bound to the ligated oligonucleotide, hybridization and washing conditions are used to remove or dissociate the target nucleic acid from unligated oligonucleotides while target nucleic acid hybridizing with the ligated oligonucleotides will remain bound to the beads. In this embodiment, the circular probe only hybridizes to the target nucleic acid when the target nucleic acid is hybridized with a ligated oligonucleotide that is immobilized on a bead.

As is well known in the art, an appropriate polymerase (3' exo⁻) is added to the array. The polymerase extends the sequence of a single-stranded DNA using double-stranded DNA as a primer site. In one embodiment, the circular DNA that has hybridized with the appropriate OLA reaction product serves as the primer for the polymerase. In the presence of an appropriate reaction buffer as is known in the art, the polymerase will extend the sequence of the primer using the single-stranded circular DNA as a template. As there is no terminus of the circular DNA, the polymerase will continue to extend the sequence of the circular DNA. In an alternative embodiment, the RCA probe comprises a discrete primer site located within the circular probe. Hybridization of primer nucleic acids to this primer site forms the polymerase template allowing RCA to proceed.

In a preferred embodiment, the polymerase creates more than 100 copies of the circular DNA. In more preferred embodiments the polymerase creates more than 1000 copies of the circular DNA; while in a most preferred embodiment the polymerase creates more than 10,000 copies or more than 50,000 copies of the template.

The amplified circular DNA sequence is then detected by methods known in the art and as described herein. Detection is accomplished by hybridizing with a labeled probe. The probe is labeled directly or indirectly. Alternatively, labeled nucleotides are incorporated into the amplified circular DNA product. The nucleotides can be labeled directly, or indirectly as is further described herein.

The RCA as described herein finds use in allowing highly specific and highly sensitive detection of nucleic acid target sequences. In particular, the method finds use in improving the multiplexing ability of DNA arrays and eliminating costly sample or target preparation. As an example, a substantial savings in cost can be realized by directly analyzing genomic DNA on an array, rather than employing an intermediate PCR amplification step. The method finds use in examining genomic DNA and other samples including mRNA.

In addition the RCA finds use in allowing rolling circle amplification products to be easily detected by hybridization to probes in a solid-phase format (e.g. an array of beads). An additional advantage of the RCA is that it provides the capability of multiplex analysis so that large numbers of sequences can be analyzed in parallel. By combining the sensitivity of RCA and parallel detection on arrays, many sequences can be analyzed directly from genomic DNA.

In an alternative embodiment, the OLA assay includes employing a standard solution phase OLA assay using adapter sequences to capture the OLA product. In this case, the allele specific oligonucleotides also contain a sequence that is complementary to a circular RCA primer that is indicative of the respective allele. That is, the OLA primer designed to hybridize to one allele contains a specific sequence for hybridization to a specific RCA primer. Likewise, the OLA primer designed to hybridize to the second allele contains a specific sequence for hybridization to a second specific RCA primer. Following OLA and capture of the OLA product, both RCA primers are hybridized with the OLA product, but only the RCA primer that is complementary to the respective RCA primer site will hybridize with that site. An RCA assay is performed and the product detected as described herein. The RCA product is an indication of the presence of a particular allele.

In one embodiment RCA is used to amplify cDNA. As is known in the art, cDNA is obtained by reverse transcription of mRNA. The resulting cDNA, therefore is a representation of the mRNA population in a given sample. Accordingly, it is desirable to examine cDNA to gain insight into the relative level of mRNA of a sample. However, frequently there exists a need to amplify the cDNA in order to obtain sufficient quantities for various analyses. Previously, amplification strategies involved exponential techniques such as PCR. A potential problem with exponential amplification is that it occasionally results in distorted mRNA profiles. Given the desire to examine mRNA populations, which provide an indication of the expression level of different gene products, there is a desire to develop amplification techniques that provide a more accurate indication of the mRNA levels in a sample.

Accordingly, the present invention provides a method of amplifying cDNA using the RCA as described herein. In a preferred embodiment, the method includes circularizing the cDNA and amplifying the circularized substrate with a DNA polymerase. In a preferred embodiment the cDNA is circularized by hybridization with a "guide linker". By "guide linker" is meant an oligonucleotide that is complementary to the 5' and 3' termini of the cDNA molecule. Generally, the 5' terminus of a cDNA molecule contains a poly-T track. In addition, the 3' terminus of cDNA frequently contains multiple C nucleotides. Generally three or four C nucleotides are added to the 3' terminus of the cDNA. Without being bound by theory, it is thought that these Cs are a result of non-template mediated addition of the C nucleotides to the 3' terminus by the DNA Polymerase. Accordingly, in a preferred embodiment the guide linker contains a plurality of A nucleotides at one terminus and a plurality of G nucleotides at the other terminus That is, it contains at its 5' terminus a plurality of G nucleotides and at its 3' terminus a plurality of A nucleotides. A preferred guide linker contains the sequence GGGAAAA, although it could contain more or fewer Gs or As at each of the respective termini.

Upon hybridization of the guide linker with the cDNA, the circular cDNA is covalently closed following incubation with ligase. That is, incubation with ligase results in covalent attachment of the 5'T and 3'C of the cDNA). The circular cDNA/guide linker complex is then contacted with a DNA polymerase that extends the circular template as described herein. The cDNA/guide linker complex serves as a template for the polymerase. This results in linear amplification of the cDNA and results in a population of cDNA that is representative of the mRNA levels of a sample. That is, the amplified cDNA provides an indication of the gene expression level of a sample. In addition, the amplified products represent full length cDNAs as a result of selection with a guide linker that contains a poly-T tract and a poly-G tract.

As described herein, in some embodiments labeled nucleotides are incorporated into the amplified cDNA product. This results in linear amplification of the signal.

The amplified cDNA product finds use in a variety of assays including gene expression analysis. The amplified products find use as probes that can be applied to an array as described herein.

Cycling Probe Technology (CPT

Cycling probe technology (CPT) is a nucleic acid detection system based on signal or probe amplification rather than target amplification, such as is done in polymerase chain reactions (PCR). Cycling probe technology relies on a molar excess of labeled probe which contains a scissile linkage of RNA. Upon hybridization of the probe to the target, the resulting hybrid contains a portion of RNA:DNA. This area of RNA:DNA duplex is recognized by RNAseH and the RNA is excised, resulting in cleavage of the probe. The probe now consists of two smaller sequences which may be released, thus leaving the target intact for repeated rounds of the reaction. The unreacted probe is removed and the label is then detected. CPT is generally described in U.S. Pat. Nos. 5,011,769, 5,403,711, 5,660,988, and 4,876,187, and PCT published applications WO 95/05480, WO 95/1416, and WO 95/00667, all of which are specifically incorporated herein by reference.

Oligonucleotide Ligation Assay

The oligonucleotide ligation assay (OLA; sometimes referred to as the ligation chain reaction (LCR)) involve the ligation of at least two smaller probes into a single long probe, using the target sequence as the template for the ligase. Another means for achieving the covalent attachment of the first and second nucleotide sequences when the sequences are hybridized to non-contiguous portions of the target nucleotide sequence involves the use of a nucleotide sequence that is sufficiently complementary to the non-contiguous portion of the target nucleotide sequence lying between the first and second nucleotide sequences. For purposes of this description such a nucleotide sequence will be referred to as an intervening linker sequence. The linker sequence can be prepared by known methods such as those described above for the preparation of the first and second nucleotide sequences. The linker sequence can be hybridized to the target sequence between the first and second nucleotide sequences. The linker sequence can then be covalently attached to both the first and second nucleotide sequence utilizing enzymatic or chemical means as referred to above. It is also possible to utilize combinations of linker sequences and polymerase to achieve a contiguous relationship between the first and second nucleotide sequences when these sequences are bound to the target nucleotide sequence. See generally U.S. Pat. Nos. 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference.

Invader™

Invader™ technology is based on structure-specific polymerases that cleave nucleic acids in a site-specific manner. Two probes are used: an "invader" probe and a "signaling" probe, that adjacently hybridize to a target sequence with a non-complementary overlap. The enzyme cleaves at the overlap due to its recognition of the "tail", and releases the "tail" with a label. This can then be detected. The Invader™ technology is described in U.S. Pat. Nos. 5,846,717; 5,614,402; 5,719,028; 5,541,311; and 5,843,669, all of which are hereby incorporated by reference.

ICAN Amplification

ICAN methodology is a preferred amplification method that includes hybridizing chimeric-primers composed of RNA (3' end) and DNA (5' end) and providing a DNA polymerase with strand displacement activity (BcaBEST™ DNA polymerase from Takara Shuzo Co., Ltd), which extends the primer forming a double stranded intermediate. Subsequently, a ribonuclease cleaves the junction of the DNA-RNA hybrid (RNase H). Subsequently, an additional chimeric primer hybridizes with the extension product or original target and displaces one strand of the double stranded intermediate. This cycle is repeated thereby amplifying the target. Amplification is outlined in FIG. 12. In a preferred embodiment ICAN method can be used to amplify specific regions of DNA at a constant temperature of 50 to 65° C. That is, the amplification is isothermal.

SPIA™

In a preferred embodiment, a linear amplification scheme known as ESPIA, or SPIA is applied. This amplification technique is disclosed in WO 01/20035 A2 and U.S. Pat. No. 6,251,639, which are incorporated by reference herein. Generally, the method includes hybridizing chimeric RNA/DNA amplification primers to the probes or target. Preferably the DNA portion of the probe is 3' to the RNA. Optionally the method includes hybridizing a polynucleotide comprising a termination polynucleotide sequence to a region of the template that is 5' with respect to hybridization of the composite primer to the template. Following hybridization of the primer to the template, the primer is extended with DNA polymerase. Subsequently, the RNA is cleaved from the composite primer with an enzyme that cleaves RNA from an RNA/DNA hybrid. Subsequently, an additional RNA/DNA chimeric primer is hybridized to the template such that the first extended primer is displaced from the target probe. The extension reaction is repeated, whereby multiple copies of the probe sequence are generated.

Amplicon Enrichment

In this alternate method, following amplification, as described above, the amplicons are hybridized to a solid-phase containing immobilized targets, i.e. genomic DNA or oligonucleotides corresponding to targeted SNPs. Preferably the amplification primers include universal primers, as described herein. In a preferred embodiment hybridization is performed at high temperatures such that only the desired PCR products (those that include or span the particular allele) are retained, while non-specific products or primer-dimers, which have a reduced Tm are removed by washing. That is, the notable difference between the $T_m$s of specific products, which are preferably form 65 to 85° C., more preferably form 70 to 80° C., and the $T_m$s of the non-specific products, which is around from about 45-60° C., provides a separation window for controlling or discriminating between the two populations during hybridization and washing.

The immobilized target can be any nucleic acid as described herein. Preferably the immobilized target is genomic DNA or oligonucleotides corresponding to particular SNPs. Alternatively, it could be pooled genomic DNA from a variety of sources or individually amplified products.

Once the non-specific products have been removed, the retained PCR products may be detected. Alternatively, they may be additionally amplified. Alternatively, they may be used in any genotyping assays as are known in the art and described herein.

Label

By "detection label" or "detectable label" herein is meant a moiety that allows detection. This may be a primary label or a secondary label. Accordingly, detection labels may be primary labels (i.e. directly detectable) or secondary labels (indirectly detectable).

In a preferred embodiment, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (horseradish peroxidase, etc.) and magnetic particles. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals": see U.S. Ser. No. 09/315,584, hereby incorporated by reference), pyrene, Malacite green, stilbene, Lucifer Yellow, Cascade Blue™, Texas Red, Cy dyes (Cy3, Cy5, etc.), alexa dyes, phyco-erythin, bodipy, and others described in the 6th Edition of the Molecular Probes Handbook by Richard P. Haugland, hereby expressly incorporated by reference.

In a preferred embodiment, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels find particular use in systems requiring separation of labeled and unlabeled probes, such as SBE, OLA, invasive cleavage reactions, etc; in addition, these techniques may be used with many of the other techniques described herein. Secondary labels include, but are not limited to, one of a binding partner pair; chemically modifiable moieties; nuclease inhibitors, enzymes such as horseradish peroxidase, alkaline phosphatases, lucifierases, etc.

In a preferred embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises biotin or imino-biotin and streptavidin Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In a preferred embodiment, the binding partner pair comprises a primary detection label (for example, attached to the NTP and therefore to the extended primer) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$-$10^{-6}$ M$^{-1}$, with less than about $10^{-5}$ to $10^{-9}$ M$^{-1}$ being preferred and less than about $10^{-7}$-$10^{-9}$ M$^{-1}$ being particularly preferred.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference).

However, in this embodiment, the label is a secondary label, a purification tag, that can be used to capture the sequence comprising the tag onto a second solid support surface.

The addition of the polymerase and the labeled dNTP are done under conditions to allow the formation of a modified first probe. The modified first probe is then added to a second solid support using the purification tag as outlined herein.

Once immobilized, several reagents are adding to the modified probe. In a preferred embodiment, first and second universal probes are added, with a polymerase and dNTPs, such that the modified probe is amplified to form amplicons, which can then be detected on arrays as outlined below. While the figures are generally directed to PCR systems, other amplification systems can be used, as are generally outlined in Ser. No. 09/517,945, filed Mar. 3, 2000, 60/161,148, filed Oct. 22, 1999, 60/135,051, filed May 20, 1999, 60/244,119, filed Oct. 26, 2000, Ser. No. 09/556,463, filed Apr. 21, 2000, and Ser. No. 09/553,993, filed Apr. 20, 2000, all of which are expressly incorporated herein by reference.

Combination Techniques

Other preferred configurations of the system are shown in the figures.

In one embodiment the target nucleic acid is first immobilized. This is followed by a specificity step, i.e. allele specific extension (see FIG. 1) and amplification. That is, following immobilization of the target nucleic acids, the target nucleic acids are contacted with allele specific probes under stringent annealing conditions. Non-hybridized probes are removed by a stringent wash. Subsequently the hybridized probes or primers are contacted with an enzyme such as a polymerase in the presence of labeled ddNTP (see FIG. 1) forming a modified primer. Preferably the label is a purification tag as described herein. The ddNTP is only incorporated into the primer that is perfectly complementary to the target nucleic acid. The modified primer is then eluted from the immobilized target nucleic acid, and contacted with amplification primers to form amplicons. In one embodiment the eluted primer is purified by binding to a binding partner for the affinity tag. Then the purified and modified primer is contacted with amplification primers for amplification, forming amplicons. The amplicons are then detected as an indication of the presence of the particular target nucleic acid.

Figure 1A:
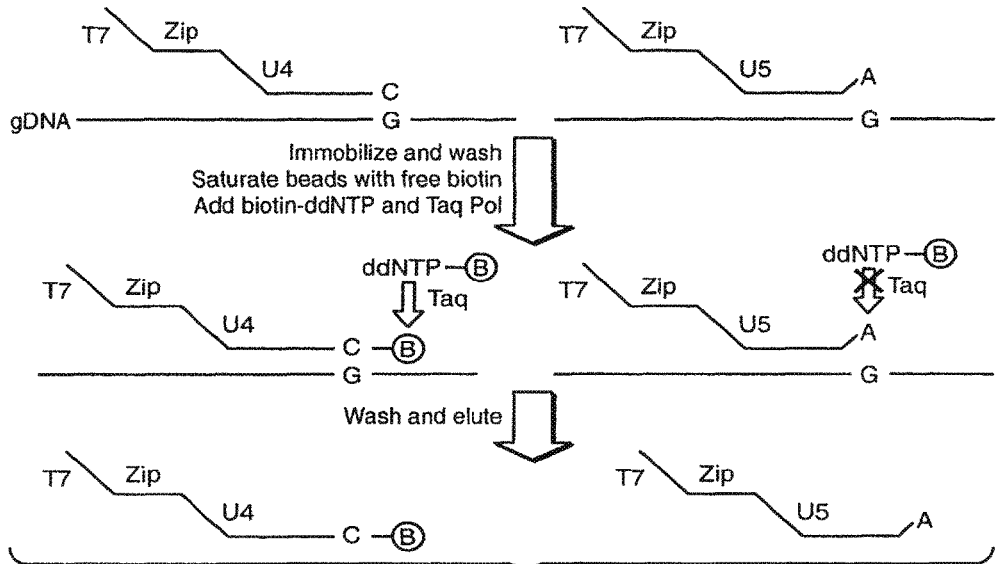
FIGS. 1A and 1B depict a schematic of a preferred embodiment of the invention. The primary steps of the method include annealing oligonucleotides to immobilized target (e.g. genomic) DNA, a chain extension reaction that is terminated by tagged (e.g. biotinylated) ddNTPs, isolation and amplification of the tagged extension products.
Figure 1B:
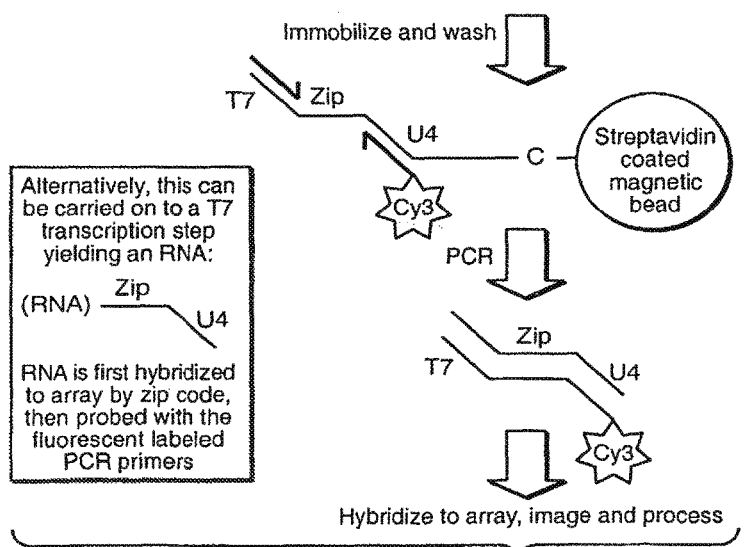

In a preferred embodiment, as shown in FIG. 1, the allele specific primer also includes an adapter sequence and priming sequences. That is, the primer includes from 5' to 3', and upstream amplification priming site, an adapter sequence, a downstream amplification priming site, and an allele specific sequence Priming sequences hybridize with amplification primers; the adapter sequence mediates attachment of the amplicons to a support for subsequent detection of amplicons. In preferred embodiments, as described herein, the priming sequences are universal priming sequences. This allows for highly multiplexed amplification. In a preferred embodiment at least one of the universal priming sequences is specific for a particular allele.

As shown in the figures, allele detection can proceed on a number of levels. In one embodiment adapters are distinct for the particular allele. Thus, following amplification of the adapter sequences, detection of the adapter provides identification of the particular allele to be detected.

Alternatively, allele detection proceeds as a result of allele specific amplification. As shown in FIG. 1, at least one of the priming sequences on the primers for each allele is specific for a particular allele. Thus, following the specificity assay, one of the alleles will be identified. Following addition of the respective amplification primers, only one set of the primers will hybridize with the priming sequences. Thus, only one of the sets of primers will generate an amplicon. In a preferred embodiment, each of the sets of primers is labeled with distinct label. Because only one of the sets will be amplified, detection of a label provides an indication of the primer that was amplified. This, in turn identifies the nucleotide at the detection position.

Figure 2:
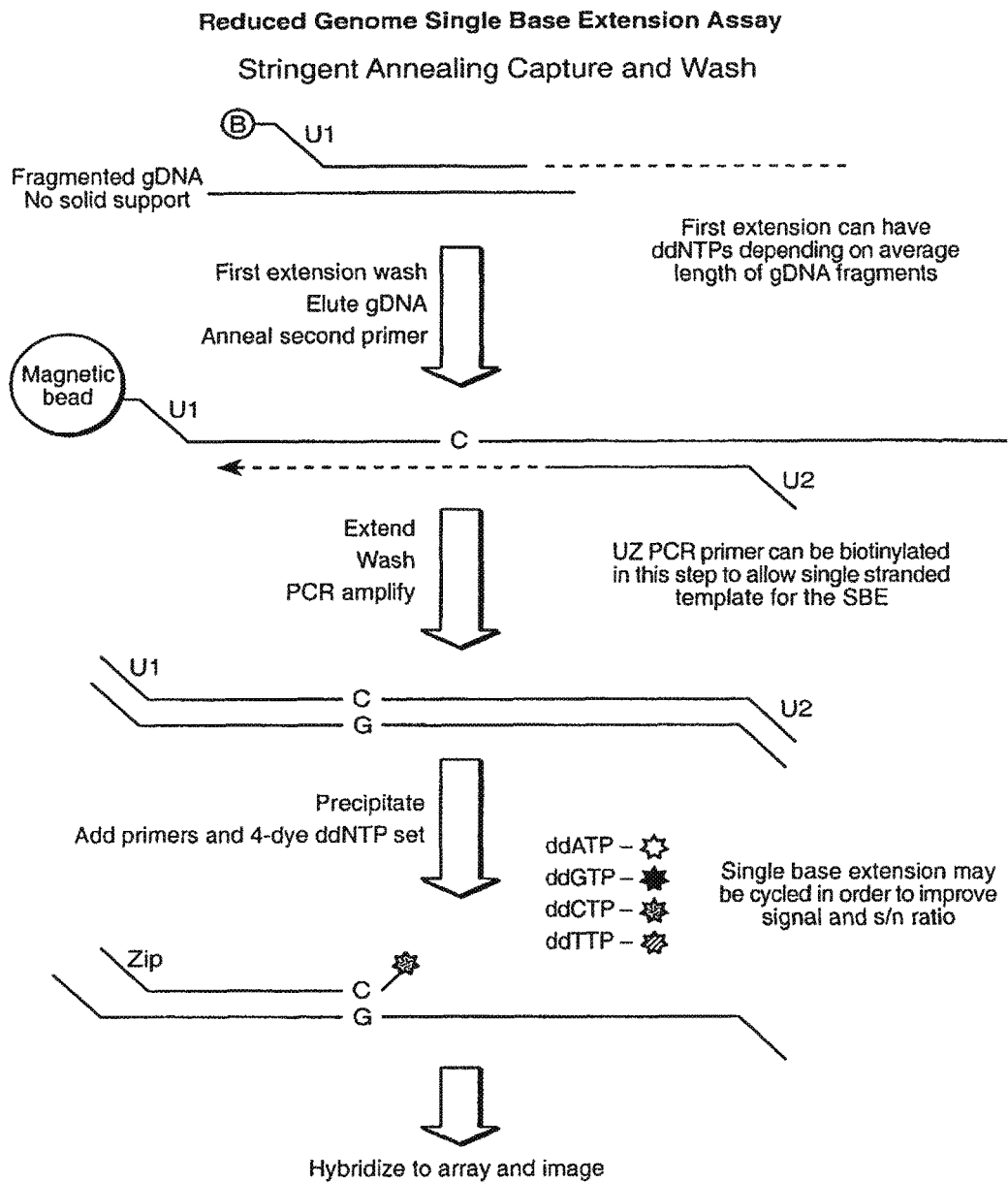
FIG. 2 depicts a preferred method of obtaining templates for single base extension reaction analysis. The four major phases are 1) First Extension from target (gDNA), 2) Second Extension, 3) PCR Amplification, and 4) Allele Specific 4-Dye Single Base Extension.

In an alternative embodiment the target nucleic acid is first contacted with a first target specific probe under stringent annealing conditions and a first extension reaction is performed with either dNTPs or ddNTPS forming a first extension product (see FIG. 2). The first target specific probe in this embodiment is either a locus specific probe or an allele specific probe. This step reduces the complexity of the sample. Subsequently the first extension product is contacted with a second probe that has the same sequence as a portion of the target sequence, i.e. the second probe is complementary to the extension product, and again can be either an allele specific probe or a locus specific probe. Following hybridization of the second probe, a second extension reaction is performed.

In a preferred embodiment the primers for the first and second extension reaction also include amplification priming sites. Preferably the amplification priming sites are universal priming sites as described herein. Accordingly, the resulting extension product is amplified (the amplification component of the multiplexing scheme). The resulting double stranded product is then denatured and either of the strands is used as a template for a single base extension (SBE) reaction as described in more detail below (the specificity component). In the SBE reaction, chain terminating nucleotides such as ddTNPs are used as substrates for the polymerase and are incorporated into a target probe that is hybridized to the single stranded amplicon template adjacent to the interrogation position. Preferably the ddNTPs are labeled as described below. Preferably, the ddNTPs are discretely labeled such that they can be discriminated in the detection step.

In an alternative embodiment a first biotinylated or otherwise tagged probe is hybridized with a target nucleic acid and a first extension reaction is performed. The primer or probe is either an allele specific or locus specific probe. The extended product is then purified from the mixture by the tag. Again, this serves as the complexity reduction step. Subsequently, a second primer is hybridized to the first extension product and a second extension reaction is performed, preferably in an allele specific manner, i.e. with discriminatory probes that are specific for each allele. This represents the specificity step. Preferably, both of the primers used in the extension reactions contain universal priming sites. Thus, universal primers can be added for universal amplification of the extension products (the amplification component) (see FIG. 3). In a preferred embodiment, each allele specific primer includes a distinct amplification priming site. Thus, following allele discrimination, only one of the primers can be used for amplification, resulting in allele specific amplification. Preferably the amplification primers contain discrete labels, which again allows for detection of which particular primers served as amplification templates. This, again, identifies the particular allele to be detected. In an additional preferred embodiment, at least one of the primers includes an adapter sequence as outlined below.

In an alternative embodiment tagged, i.e. biotinylated, primers are hybridized with a target nucleic acid. Preferably the hybridization complex is immobilized. Either the target or the primer can be the immobilized component. After annealing, the immobilized complexes are washed to remove unbound nucleic acids. This is followed by an extension reaction. This is the complexity reduction component of the assay. Subsequently, the extended probe is removed via the purification tag. The purified probe is then hybridized with allele specific probes (the specificity component). The hybridized probes are then amplified (the amplification component) (see FIG. 4).

In a preferred embodiment the allele specific probe contains universal priming sites and an adapter sequence. Preferably the universal priming sites are specific for a particular allele. That is, one of the universal priming sites may be common to all alleles, but the second universal priming site is specific for a particular allele. Following hybridization the allele specific primer, the complexes are washed to remove unbound or mismatched primers. Thus, this configuration allows for allele specific amplification. Amplicons are detected as an indication of the presence of a particular allele.

In an alternative embodiment, the specificity component occurs first, In this embodiment allele specific probes are hybridized with the target nucleic acid; an extension assay is performed whereby only the perfectly complementary probe is extended. That is, only the probe that is perfectly complementary to the probe at the interrogation position serves as a substrate for extension reaction. Preferably the extension reaction includes tagged, i.e. biotinylated, dNTPs such that the extension product is tagged. The extension product is then purified from the reaction mixture. Subsequently, a second allele specific primer is hybridized to the extension product. This step also serves as a second specificity step. In this embodiment the specificity steps also serve as complexity reduction components in that they enrich for target nucleic acids. Following the addition of the second allele specific primer and extension, the extension product is amplified, preferably with universal primers (see FIG. 5).

As discussed previously, it is preferable for the at least one allele specific primer to contain an allele specific priming site, preferably an allele specific universal priming site. Again, this configuration allows for multiplexed allele specific amplification using universal primers.

In an alternative embodiment, the target nucleic acid is first immobilized and hybridized with allele specific primers. Preferably the allele specific primers also include an adapter sequence that is indicative of the particular allele. Allele specific extension is then performed whereby only the primer that is perfectly complementary to the detection position of the target nucleic acid will serve as a template for primer extension. That is, mismatched primers will not be extended. Of note, the allele specific position of the primer need not be the 3' terminal nucleotide of the primer (see FIGS. 7 and 8). That is, the primer may extend beyond the detection position of the target nucleic acid. In this embodiment it is preferable to include labeled dNTPs or ddNTPs or both such that the extension product is labeled and can be detected. In some preferred embodiments the interrogator is not the terminal position of the primer, but rather resides at a position 1, 2, 3, 4, 5 or 6 nucleotides from the 3' terminus of the primer.

In a preferred embodiment both dNTPs and ddNTPs are included in the extension reaction mixture. In this embodiment only one label is needed, and the amount of label can be determined and altered by varying the relative concentration of labeled and unlabeled dTNPs and ddNTPs. That is, in one embodiment labeled ddNTPs are included in the extension mix at a dilution such that each termination will result in placement of single label on each strand. Thus, this method allows for quantification of targets. Alternatively, if a higher signal is needed, a mixture of labeled dNTPs can be used along with chain terminating nucleotides at a lower concentration. The result is the incorporation of multiple labels per extension product. Preferably the primers also include adapters which facilitate immobilization of the extension products for detection.

In an additional preferred configuration, target nucleic acids are hybridized with tagged locus specific primers. Preferably the primer includes a locus specific portion and a universal priming site. Of note, as is generally true for locus specific primers, they need not be immediately adjacent to the detection position. Upon hybridization, the hybridization complexes are immobilized, preferably by binding moiety that specifically binds the tag on the locus specific primer. The immobilized complexes are then washed to remove unlabeled nucleic acids; the remaining hybridization complexes are then subject to an extension reaction. Following extension of the locus specific primer, a nucleotide complementary to the nucleotide at the detection position will be incorporated into the extension product. In some embodiments it is desirable to limit the size of the extension because this reduces the complexity of subsequent annealing steps. This may be accomplished by including both dNTPs and ddNTPs in the reaction mixture.

Following the first extension, a second locus or allele specific primer is hybridized to the immobilized extension product and a second extension reaction occurs. Preferably the second extension primer includes a target specific portion and a universal priming site. After extension, universal amplification primers can be added to the reaction and the extension products amplified. The amplicons can then be used for detection of the particular allele. This can be accomplished by competitive hybridization, as described herein. Alternatively, it can be accomplished by an additional extension reaction. When the extension reaction is performed, preferably a primer that contains an adapter sequence and a target specific portion is hybridized with the amplicons. Preferably the target specific portion hybridizes up to a position that is adjacent to the detection position, i.e. the particular allele to be detected. Polymerase and labeled ddNTPs are then added and the extension reaction proceeds, whereby incorporation of a particular label is indicative of the nucleotide that is incorporated into the extension primer. This nucleotide is complementary to the nucleotide at the detection position. Thus, analyzing or detecting which nucleotide is incorporated into the primer provides an indication of the nucleotide at the allele position. The extended primer is detected by methods that include but are not limited to the methods described herein.

In another embodiment, the genotyping specificity is conferred by the extension reaction. In this embodiment, two probes (sometimes referred to herein as "primers") are hybridized non-contiguously to a target sequence comprising, from 3' to 5', a first second and third target domain. Preferably the target is immobilized. That is, in a preferred embodiment, the target sequence is genomic DNA and is attached to a solid support as is generally described in U.S. Ser. No. 09/931,285, hereby expressly incorporated by reference in its entirety. In this embodiment, magnetic beads, tubes or microtiter plates are particularly preferred solid supports, although other solid supports as described below can also be used.

The first probe hybridized to the first domain, contains a first universal priming sequence and contains, at the 3' end (within the terminal six bases), an interrogation position. In some preferred embodiments the interrogator is not the terminal position of the primer, but rather resides at a position 1, 2, 3, 4, 5 or 6 nucleotides from the 3' terminus of the primer. Subsequently, the unhybridized primers are removed. This is followed by providing an extension enzyme such as a polymerase, and NTPs (which includes both dNTPs, NTPs and analogs, as outlined below). If the interrogation position is perfectly complementary to the detection position of the target sequence, the extension enzyme will extend through the second target domain to form an extended first probe, ending at the beginning of the third domain, to which the second probe is hybridized. A second probe is complementary to the third target domain, and upon addition of a ligase, the extended first probe will ligate to the second probe. The addition of a primer allows amplification to form amplicons. If the second probe comprises an antisense second primer, exponential amplification may occur, such as in PCR. Similarly, one or other of the probes may comprise an adapter or address sequence, which facilitates detection. For example, the adapter may serve to allow hybridization to a "universal array". Alternatively, the adapter may serve as a mobility modifier for electrophoresis or mass spectrometry analysis, or as a label sequence for the attachment of labels or beads for flow cytometry analysis.

In another embodiment, the reaction is similar except that it is the ligation reaction that provides the detection position/interrogation specificity. In this embodiment, it is the second probe that comprises a 5' interrogation position. The extended first probe will not be ligated to the second probe if there is a mismatch between the interrogation position and the target sequence. As above, the addition of a primer allows amplification to form amplicons. If the second probe comprises an antisense second primer, exponential amplification may occur, such as in PCR. Similarly, one or other of the probes may comprise an adapter or address sequence, which facilitates detection. For example, the adapter may serve to allow hybridization to a "universal array". Alternatively, the adapter may serve as a mobility modifier for electrophoresis or mass spectrometry analysis, or as a label sequence for the attachment of labels or beads for flow cytometry analysis.

Once prepared, and attached to a solid support as required, the target sequence is used in genotyping reactions. It should be noted that while the discussion below focuses on certain assays, in general, for each reaction, each of these techniques may be used in a solution based assay, wherein the reaction is done in solution and a reaction product is bound to the array for subsequent detection, or in solid phase assays, where the reaction occurs on the surface and is detected, either on the same surface or a different one.

The assay continues with the addition of a first probe. The first probe comprises, a 5' first domain comprising a first universal priming sequence. The universal priming sites are used to amplify the modified probes to form a plurality of amplicons that are then detected in a variety of ways, as outlined herein. In preferred embodiments, one of the universal priming sites is a T7 site, such that RNA is ultimately made to form the amplicon. Alternatively, as more fully outlined below, two universal priming sequences are used, one on the second probe generally in antisense orientation, such that PCR reactions or other exponential amplification reactions can be done. Alternatively, a single universal primer can be used for amplification. Linear amplification can be performed using the SPIA assay, T7 amplification, linear TMA and the like, as described herein.

The first probe further comprises, 3' to the priming sequence, a second domain comprising a sequence substantially complementary to the first target domain of the target sequence. Again, the second target domain comprises n nucleotides, wherein n is an integer of at least 1, and preferably from 1 to 100 s, with from 1 to 10 being preferred and from 1, 2, 3, 4 and 5 being particularly preferred. What is important is that the first and third target domains are non-contiguous, e.g. not adjacent.

In a preferred embodiment, the first probe, further comprises, 3' to the second domain, an interrogation position within the 3' six terminal bases. As used herein, the base which basepairs with a detection position base in a hybrid is termed a "readout position" or an "interrogation position"; thus one or the other of the first or second probes of the invention comprise an interrogation position, as outlined herein. In some cases, when two SNP positions or detection positions are being elucidated, both the first and the second probes may comprise interrogation positions.

When the first probe comprises the interrogation position, it falls within the six 3' terminal nucleotides, with within three, and preferably two, and most preferably it is the 3' terminal nucleotide. In some preferred embodiments the interrogator is not the terminal position of the primer, but rather resides at a position 1, 2, 3, 4, 5 or 6 nucleotides from the 3' terminus of the primer. Alternatively, the first probe does not contain the interrogation position; rather the second probe does. This depends on whether the extension enzyme or the ligation enzyme is to confer the specificity required for the genotyping reaction.

In addition to the first probes of the invention, the compositions of the invention further comprise a second probe for each target sequence. The second probes each comprise a first domain comprising a sequence substantially complementary to the third target domain of a target sequence as outlined herein.

In some embodiments, the second probes comprise a second universal priming site. As outlined herein, the first and second probes can comprise two universal primers, one in each orientation, for use in PCR reactions or other amplification reactions utilizing two primers. That is, as is known in the art, the orientation of primers is such to allow exponential amplification, such that the first universal priming sequence is in the "sense" orientation and the second universal priming sequence is in the "antisense" orientation.

In a preferred embodiment, it is the second probe that comprises the interrogation position. In this embodiment, the second probe comprises a 5' interrogation nucleotide, although in some instances, depending on the ligase, the interrogation nucleotide may be within 1-3 bases of the 5' terminus. However, it is preferred that the interrogation base be the 5' base.

In a preferred embodiment, either the first or second probe further comprises an adapter sequence, (sometimes referred to in the art as "zip codes") to allow the use of "universal arrays". That is, arrays are generated that contain capture probes that are not target specific, but rather specific to individual artificial adapter sequences.

It should be noted that when two universal priming sequences and an adapter is used, the orientation of the construct should be such that the adapter gets amplified; that is, the two universal priming sequences are generally at the termini of the amplification template, described below.

The first and second probes are added to the target sequences to form a first hybridization complexes. The first hybridization complexes are contacted with a first universal primer that hybridizes to the first universal priming sequence, an extension enzyme and dNTPs.

If it is the first probe that comprises the interrogation nucleotide, of the base at the interrogation position is perfectly complementary with the base at the detection position, extension of the first primer occurs through the second target domain, stopping at the 5' of the second probe, to form extended first probes that are hybridized to the target sequence, forming second hybridization complexes. If, however, the base at the interrogation position is not perfectly complementary with the base at the detection position, extension of the first probe will not occur, and no subsequent amplification or detection will occur.

Extension of the enzyme will also occur if it is the second probe that comprises the interrogation position.

Once extended, the extended first probe is adjacent to the 5' end of the second probe. In the case where the interrogation position was in the first probe, the two ends of the probes (the 3' end of the first probe and the 5' end of the second probe) are respectively perfectly complementary to the target sequence at these positions, and the two probes can be ligated together with a suitable ligase to form amplification templates.

The conditions for carrying out the ligation will depend on the particular ligase used and will generally follow the manufacturer's recommendations.

If, however, it is the second probe that carries the interrogation position at its 5' end, the base at the interrogation position must be perfectly complementary to the detection position in the target sequence to allow ligation. In the absence of perfect complementarity, no significant ligation will occur between the extended first probe and the second probe.

It should be noted that the enzymes may be added sequentially or simultaneously. If the target sequences are attached to a solid support, washing steps may also be incorporated if required.

The ligation of the extended first probe and the second probe results in an amplification template comprising at least one, and preferably two, universal primers and an optional adapter. Amplification can then be done, in a wide variety of ways. As will be appreciated by those in the art, there are a wide variety of suitable amplification techniques requiring either one or two primers, as is generally outlined in U.S. Ser. No. 09/517,945, hereby expressly incorporated by reference.

Detection Systems

All of the methods and compositions herein are drawn to methods of detecting, quantifying and/or determining the base at the detection position of a target nucleic acid, generally by having differential reactions occur depending on the presence or absence of a mismatch. The reaction products are generally detected on arrays as is outlined herein, although a number of different detection methods may be used.

As is more fully outlined below, preferred systems of the invention work as follows. An amplicon is attached (via hybridization) to an array site. This attachment is generally a direct hybridization between a adapter on the amplicon and a corresponding capture probe, although in some instances, the system can rely on indirect "sandwich" complexes using capture extender probes as are known in the art. In a preferred embodiment, the target sequence (e.g. the amplicon) itself comprises the labels. Alternatively, a label probe is added, that will hybridize to a label sequence on the amplicon, forming an assay complex. The capture probes of the array are substantially (and preferably perfectly) complementary to the adapter sequences.

The terms length determination, separation-by-length assay, and separation-by-length assay medium are taken collectively to mean a process and its related apparatus that achieves separation of DNA fragments on the basis of length, size, mass, or any other physical property. This includes generally, liquid chromatography, electrophoresis and direct mass spectrometry; more particularly, high performance liquid chromatography (HPLC) and capillary electrophoresis or gel electrophoresis, and MALDI-TOF MS respectively.

Other detection assays or formats include classical configurations such as the "dot-blot". This method of hybridization gained wide-spread use, and many versions were developed (see M. L. M. Anderson and B. D. Young, in Nucleic Acid Hybridization-A Practical Approach, B. D. Hames and S. J. Higgins, Eds., IRL Press, Washington D.C., Chapter 4, pp. 73-111, 1985). The "dot blot" hybridization has been further developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

Another format, the so-called "sandwich" hybridization, involves attaching oligonucleotide probes covalently to a solid support and using them to capture and detect multiple nucleic acid targets. (M. Ranki et al., Gene, 21, pp. 77-85, 1983; A. M. Palva, T. M. Ranki, and H. E. Soderlund, in UK Patent Application GB 2156074A, Oct. 2, 1985; T. M. Ranki and H. E. Soderlund in U.S. Pat. No. 4,563,419, Jan. 7, 1986; A. D. B. Malcolm and J. A. Langdale, in PCT WO 86/03782, Jul. 3, 1986; Y. Stabinsky, in U.S. Pat. No. 4,751,177, Jan. 14, 1988; T. H. Adams et al., in PCT WO 90/01564, Feb. 22, 1990; R. B. Wallace et al. 6 Nucleic Acid Res. 11, p. 3543, 1979; and B. J. Connor et al., 80 Proc. Natl. Acad. Sci. USA pp. 278-282, 1983). Multiplex versions of these formats are called "reverse dot blots".

In another approach of matrix hybridization, Beattie et al., in The 1992 San Diego Conference: Genetic Recognition, November, 1992, used a microrobotic system to deposit micro-droplets containing specific DNA sequences into individual microfabricated sample wells on a glass substrate. The hybridization in each sample well is detected by interrogating miniature electrode test fixtures, which surround each individual microwell with an alternating current (AC) electric field.

One preferred aspect of the present invention is that it results in high-throughput screening capabilities. In the assays described herein, from a few up to millions of different tags identifying, e.g., SNPs, can be identified simultaneously. For example, using simple dot-blot hybridization methods, membranes with thousands of immobilized probes can be generated for screening against tags. The solid-phase techniques described below can be adapted to having literally millions of different immobilized nucleic acids per square inch. Similarly, very large sets of amplified DNAs, e.g., tags, can be immobilized on membranes for simultaneous screening against one or more sequence.

In one embodiment, the identity of the amplification products are determined by detecting the molecular weights of the amplification product or a fragment thereof, such as by chromatography or mass spectroscopy.

For instance, the gross molecular weight of an amplification product or a discrete fragment thereof can be detected. As set forth above, each member of a probe library (i.e., all of the probes in the reaction) has a unique molecular weight label based on the particular sequence of the tag. For instance, mass spectrometry can provide high detection sensitivity and accuracy of mass measurements that can discern between probes which, while identical in length, differ in sequence by only base. Thus, complex libraries can be constructed by calculating the overall molecular weight of each amplification product to be detected by varying the G/C/A/T content in the tag sequence. In certain preferred embodiments, the nucleic acid sequence which is being detected includes, as its only variable sequence, the tag sequence and not the template homology regions. Such fragments can be generated, for example, by including restriction sites that flank the tag sequence, or choosing the PCR primers such that only the tag sequence is the only variable region of the covalently closed circular product which is included in the amplification products. That being said, in those embodiments where the amplification product which is being detected also includes the template homology region(s), the calculation and design of the tag sequences will need to include the variability in the THRs as well in order to produce products having a unique molecular weight so as to be discernable from one another by mass spectroscopy or other detection means as may be chosen.

Those skilled in the art will recognize that very simple algorithms can be used to calculate the molecular weights for each member of a library by varying the sequence of the tag, taking into account if necessary the sequences of the template homology regions. The molecular weight complexity of the tag can be increased by allowing the probes to vary in length as well sequence.

In certain instances, the library can be deconvoluted by chromatographic techniques prior to detection by mass spectroscopy. For example, prior to introducing a sample into the spectrometer, the mixture can first be at least semi-purified. Separation procedures based on size (e.g. gel-filtration), solubility (e.g. isoelectric precipitation) or electric charge (e.g. electrophoresis, isoelectric focusing, ion exchange chromatography) may be used to separate a mixture of amplimers. A preferred separation procedure is high performance liquid chromatography (HPLC).

In certain embodiments, the amplification product can include an integrated mass label for multiplex sequencing. Multiplexing by mass modification in this case is obtained by mass-modifying the nucleic acid primer, e.g., at the level of the sugar or base moiety. Such embodiments are most practical when amplification products are to be mixed for detection after the amplification step rather than before.

Suitable mass spectrometry techniques for use in the present invention include DNA analyses of the present invention include collision-induced dissociation (CID) fragmentation analysis (e.g., CID in conjunction with a MS/MS configuration, see Schram, K. (1990) "Mass Spectrometry of Nucleic Acid Components," in Biomedical Applications of Mass Spectrometry 34:203-287; and Crain P. (1990) Mass Spectrometry Reviews 9:505-554); fast atomic bombardment (FAB mass spectrometry) and plasma desorption (PD mass spectrometry), see Koster et al. (1987 Biomedical Environmental Mass Spectrometry 14:111-116; and electrospray/ionspray (ES) and matrix-assisted laser desorption/ionization (MALDI) mass spectrometry (see Fenn et al. (1984) J. Phys. Chem. 88:4451-4459, Smith et al. (1990) Anal. Chem. 62:882-889, and Ardrey, B. (1992) Spectroscopy Europe 4:10-18). MALDI mass spectrometry is particularly well suited to such analyses when a time-of-flight (TOF) configuration is used as a mass analyzer (MALDI-TOF). See International Publication No. WO 97/33000, published Sep. 12, 1997, see also Huth-Fehre et al. (1992) Rapid Communications in Mass Spectrometry 6:209-213, and Williams et al. (1990) Rapid Communications in Mass Spectrometry 4:348-351.

Suitable mass spectrometry techniques for use in the mass tag analyses of the present invention include collision-induced dissociation (CID) fragmentation analysis (e.g., CID in conjunction with a MS/MS configuration, see Schram, K. (1990) "Mass Spectrometry of Nucleic Acid Components," in Biomedical Applications of Mass Spectrometry 34:203-287; and Crain P. (1990) Mass Spectrometry Reviews 9:505-554); fast atomic bombardment (FAB mass spectrometry) and plasma desorption (PD mass spectrometry), see Koster et al. (1987 Biomedical Environmental Mass Spectrometry 14:111-116; and electrospray/ionspray (ES) and matrix-assisted laser desorption/ionization (MALDI) mass spectrometry (see Fenn et al. (1984) J. Phys. Chem. 88:4451-4459, Smith et al. (1990) Anal. Chem. 62:882-889, and Ardrey, B. (1992) Spectroscopy Europe 4:10-18). MALDI mass spectrometry is particularly well suited to such analyses when a time-of-flight (TOF) configuration is used as a mass analyzer (MALDI-TOF). See International Publication No. WO 97/33000, published Sep. 12, 1997, see also Huth-Fehre et al. (1992) Rapid Communications in Mass Spectrometry 6:209-213, and Williams et al. (1990) Rapid Communications in Mass Spectrometry 4:348-351.

In this regard, a number of mass tags suitable for use with nucleic acids are known (see U.S. Pat. No. 5,003,059 to Brennan and U.S. Pat. No. 5,547,835 to Koster), including mass tags which are cleavable from the nucleic acid (see International Publication No. WO 97/27331).

In another embodiment, the hybridization tags are detected on a micro-formatted multiplex or matrix devices (e.g., DNA chips) (see M. Barinaga, 253 Science, pp. 1489, 1991; W. Bains, 10 Bio/Technology, pp. 757-758, 1992). These methods usually attach specific DNA sequences to very small specific areas of a solid support, such as microwells of a DNA chip. In one variant, the invention is adapted to solid phase arrays for the rapid and specific detection of multiple polymorphic nucleotides, e.g., SNPs. Typically, an oligonucleotide is linked to a solid support and a tag nucleic acid is hybridized to the oligonucleotide. Either the oligonucleotide, or the tag, or both, can be labeled, typically with a fluorophore. Where the tag is labeled, hybridization is detected by detecting bound fluorescence. Where the oligonucleotide is labeled, hybridization is typically detected by quenching of the label. Where both the oligonucleotide and the tag are labeled, detection of hybridization is typically performed by monitoring a color shift resulting from proximity of the two bound labels. A variety of labeling strategies, labels, and the like, particularly for fluorescent based applications are described, supra.

In one embodiment, an array of oligonucleotides are synthesized on a solid support. Exemplary solid supports include glass, plastics, polymers, metals, metalloids, ceramics, organics, etc. Using chip masking technologies and photoprotective chemistry it is possible to generate ordered arrays of nucleic acid probes. These arrays, which are known, e.g., as "DNA chips," or as very large scale immobilized polymer arrays ("VLSIPS™" arrays) can include millions of defined probe regions on a substrate having an area of about 1 $cm^2$ to several $cm^2$, thereby incorporating sets of from a few to millions of probes.

The construction and use of solid phase nucleic acid arrays to detect target nucleic acids is well described in the literature. See, Fodor et al. (1991) Science, 251: 767-777; Sheldon et al. (1993) Clinical Chemistry 39(4): 718-719; Kozal et al. (1996) Nature Medicine 2(7): 753-759 and Hubbell U.S. Pat. No. 5,571,639. See also, Pinkel et al. PCT/US95/16155 (WO 96/17958). In brief, a combinatorial strategy allows for the synthesis of arrays containing a large number of probes using a minimal number of synthetic steps. For instance, it is possible to synthesize and attach all possible DNA 8 mer oligonucleotides (48, or 65,536 possible combinations) using only 32 chemical synthetic steps. In general, VLSIPS™ procedures provide a method of producing 4n different oligonucleotide probes on an array using only 4n synthetic steps.

Light-directed combinatorial synthesis of oligonucleotide arrays on a glass surface is performed with automated phosphoramidite chemistry and chip masking techniques similar to photoresist technologies in the computer chip industry. Typically, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface.

A 96 well automated multiplex oligonucleotide synthesizer (A.M.O.S.) has also been developed and is capable of making thousands of oligonucleotides (Lashkari et al. (1995) PNAS 93: 7912). Existing light-directed synthesis technology can generate high-density arrays containing over 65,000 oligonucleotides (Lipshutz et al. (1995) BioTech. 19: 442).

Combinatorial synthesis of different oligonucleotide analogues at different locations on the array is determined by the pattern of illumination during synthesis and the order of addition of coupling reagents. Monitoring of hybridization of target nucleic acids to the array is typically performed with fluorescence microscopes or laser scanning microscopes. In addition to being able to design, build and use probe arrays using available techniques, one of skill is also able to order custom-made arrays and array-reading devices from manufacturers specializing in array manufacture. For example, Affymetrix Corp., in Santa Clara, Calif. manufactures DNA VLSIP™ arrays.

It will be appreciated that oligonucleotide design is influenced by the intended application. For example, where several oligonucleotide-tag interactions are to be detected in a single assay, e.g., on a single DNA chip, it is desirable to have similar melting temperatures for all of the probes. Accordingly, the length of the probes are adjusted so that the melting temperatures for all of the probes on the array are closely similar (it will be appreciated that different lengths for different probes may be needed to achieve a particular $T_m$ where different probes have different GC contents). Although melting temperature is a primary consideration in probe design, other factors are optionally used to further adjust probe construction, such as selecting against primer self-complementarity and the like. The "active" nature of the devices provide independent electronic control over all aspects of the hybridization reaction (or any other affinity reaction) occurring at each specific microlocation. These devices provide a new mechanism for affecting hybridization reactions which is called electronic stringency control (ESC). For DNA hybridization reactions which require different stringency conditions, ESC overcomes the inherent limitation of conventional array technologies. The active devices of this invention can electronically produce "different stringency conditions" at each microlocation. Thus, all hybridizations can be carried out optimally in the same bulk solution. These arrays are described in U.S. Pat. No. 6,051,380 by Sosnowski et al.

Accordingly, the present invention provides array compositions comprising at least a first substrate with a surface comprising individual sites. By "array" or "biochip" herein is meant a plurality of nucleic acids in an array format; the size of the array will depend on the composition and end use of the array. Nucleic acids arrays are known in the art, and can be classified in a number of ways; both ordered arrays (e.g. the ability to resolve chemistries at discrete sites), and random arrays (e.g. bead arrays) are included. Ordered arrays include, but are not limited to, those made using photolithography techniques (Affymetrix GeneChip™), spotting techniques (Synteni and others), printing techniques (Hewlett Packard and Rosetta), electrode arrays, three dimensional "gel pad" arrays, etc. Liquid arrays may also be used, i.e. three-dimensional array methods such as flow cytometry. When flow cytometry is the detection method, amplicons are immobilized to a support such as a microsphere as described herein. The microspheres are applied to a flow cytometer and the amplicons are detected optically as described herein.

In a preferred embodiment, when beads are used, the beads are distributed in or on an additional support or substrate is generally flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics. In a preferred embodiment such substrates include multi-well plates as are known in the art. In a preferred embodiment magnetic force is used to immobilized magnetic beads on the solid support.

A preferred embodiment utilizes microspheres on a variety of array substrates including fiber optic bundles, as are outlined in PCTs US98/21193 which published as WO1999018434, PCT US99/14387 which published as WO1999067641 and PCT US98/05025 which published as WO1998040726; WO98/50782; and U.S. Ser. No. 09/287,573 which issued as U.S. Pat. No. 7,348,181, U.S. Ser. No. 09/151,877 which issued as U.S. Pat. No. 6,327,410, U.S. Ser. No. 09/256,943 which issued as U.S. Pat. No. 6,429,027, U.S. Ser. No. 09/316,154 which published as U.S. 20020051971 and is now abandoned, U.S. Ser. No. 60/119,323, U.S. Ser. No. 09/315,584 which issued as U.S. Pat. No. 6,544,732; all of which are expressly incorporated by reference. While much of the discussion below is directed to the use of microsphere arrays on fiber optic bundles, any array format of nucleic acids on solid supports may be utilized.

Arrays containing from about 2 different bioactive agents (e.g. different beads, when beads are used) to many millions can be made, with very large arrays being possible. Generally, the array will comprise from two to as many as a billion or more, depending on the size of the beads and the array substrate, as well as the end use of the array, thus very high density, high density, moderate density, low density and very low density arrays may be made. Preferred ranges for very high density arrays are from about 10,000,000 to about 2,000,000,000, with from about 100,000,000 to about 1,000,000,000 being preferred (all numbers being in square cm). High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple array substrates may be used, either of different or identical compositions. Thus for example, large arrays may comprise a plurality of smaller array substrates.

In addition, one advantage of the present compositions is that particularly through the use of fiber optic technology, extremely high density arrays can be made. Thus for example, because beads of 200 μm or less (with beads of 200 nm possible) can be used, and very small fibers are known, it is possible to have as many as 40,000 or more (in some instances, 1 million) different elements (e.g. fibers and beads) in a 1 $mm^2$ fiber optic bundle, with densities of greater than 25,000,000 individual beads and fibers (again, in some instances as many as 50-100 million) per 0.5 $cm^2$ obtainable (4 million per square cm for 5μ center-to-center and 100 million per square cm for 1μ center-to-center).

By "array substrate" or "array solid support" or other grammatical equivalents herein is meant any material that can be modified to contain discrete individual sites appropriate for the attachment or association of beads and is amenable to at least one detection method. As will be appreciated by those in the art, the number of possible array substrates is very large. Possible array substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In general, the array substrates allow optical detection and do not themselves appreciably fluoresce.

Generally the array substrate is flat (planar), although as will be appreciated by those in the art, other configurations of array substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred array substrates include optical fiber bundles as discussed below, and flat planar array substrates such as paper, glass, polystyrene and other plastics and acrylics.

In a preferred embodiment, the array substrate is an optical fiber bundle or array, as is generally described in U.S. Ser. Nos. 08/944,850 and 08/519,062, PCT US98/05025, and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

Generally, the arrayed array compositions of the invention can be configured in several ways; see for example U.S. Ser. No. 09/473,904 which issued as U.S. Pat. No. 6,858,394, hereby expressly incorporated by reference. In a preferred embodiment, as is more fully outlined below, a "one component" system is used. That is, a first array substrate comprising a plurality of assay locations (sometimes also referred to herein as "assay wells"), such as a microtiter plate, is configured such that each assay location contains an individual array. That is, the assay location and the array location are the same. For example, the plastic material of the microtiter plate can be formed to contain a plurality of "bead wells" in the bottom of each of the assay wells. Beads containing the capture probes of the invention can then be loaded into the bead wells in each assay location as is more fully described below.

Alternatively, a "two component" system can be used. In this embodiment, the individual arrays are formed on a second array substrate, which then can be fitted or "dipped" into the first microtiter plate substrate. A preferred embodiment utilizes fiber optic bundles as the individual arrays, generally with "bead wells" etched into one surface of each individual fiber, such that the beads containing the capture probes are loaded onto the end of the fiber optic bundle. The composite array thus comprises a number of individual arrays that are configured to fit within the wells of a microtiter plate.

By "composite array" or "combination array" or grammatical equivalents herein is meant a plurality of individual arrays, as outlined above. Generally the number of individual arrays is set by the size of the microtiter plate used; thus, 96 well, 384 well and 1536 well microtiter plates utilize composite arrays comprising 96, 384 and 1536 individual arrays, although as will be appreciated by those in the art, not each microtiter well need contain an individual array. It should be noted that the composite arrays can comprise individual arrays that are identical, similar or different. That is, in some embodiments, it may be desirable to do the same 2,000 assays on 96 different samples; alternatively, doing 192,000 experiments on the same sample (i.e. the same sample in each of the 96 wells) may be desirable. Alternatively, each row or column of the composite array could be the same, for redundancy/quality control. As will be appreciated by those in the art, there are a variety of ways to configure the system. In addition, the random nature of the arrays may mean that the same population of beads may be added to two different array surfaces, resulting in substantially similar but perhaps not identical arrays.

At least one surface of the array substrate is modified to contain discrete, individual sites for later association of microspheres. These sites may comprise physically altered sites, i.e. physical configurations such as wells or small depressions in the array substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the array substrate. However, it should be noted that these sites may not be discrete sites. That is, it is possible to use a uniform surface of adhesive or chemical functionalities, for example, that allows the attachment of beads at any position. That is, the surface of the array substrate is modified to allow attachment of the microspheres at individual sites, whether or not those sites are contiguous or non-contiguous with other sites. Thus, the surface of the array substrate may be modified such that discrete sites are formed that can only have a single associated bead, or alternatively, the surface of the array substrate is modified and beads may go down anywhere, but they end up at discrete sites. That is, while beads need not occupy each site on the array, no more than one bead occupies each site.

In a preferred embodiment, the surface of the array substrate is modified to contain wells, i.e. depressions in the surface of the array substrate. This may be done as is generally known in the art using a variety of techniques, including, but not limited to, photolithography, stamping techniques, molding techniques and microetching techniques. As will be appreciated by those in the art, the technique used will depend on the composition and shape of the array substrate.

In a preferred embodiment, physical alterations are made in a surface of the array substrate to produce the sites. In a preferred embodiment, the array substrate is a fiber optic bundle and the surface of the array substrate is a terminal end of the fiber bundle, as is generally described in U.S. Ser. No. 08/818,199 which issued as U.S. Pat. No. 6,023,540, and U.S. Ser. No. 09/151,877 which issued as U.S. Pat. No. 6,327,410, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the array substrate is modified to contain chemically modified sites, that can be used to attach, either covalently or non-covalently, the microspheres of the invention to the discrete sites or locations on the array substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

In some embodiments, the beads are not associated with an array substrate. That is, the beads are in solution or are not distributed on a patterned substrate.

In a preferred embodiment, the compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each capture probe; preferred embodiments utilize a plurality of beads of each type.

By "microspheres" or "beads" or "particles" or grammatical equivalents herein is meant small discrete particles. The composition of the beads will vary, depending on the class of capture probe and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "*Microsphere Detection Guide*" from Bangs Laboratories, Fishers Ind. is a helpful guide.

The beads need not be spherical; irregular particles may be used. In addition, the beads may be porous, thus increasing the surface area of the bead available for either capture probe attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

It should be noted that a key component of the invention is the use of an array substrate/bead pairing that allows the association or attachment of the beads at discrete sites on the surface of the array substrate, such that the beads do not move during the course of the assay.

Each microsphere comprises a capture probe, although as will be appreciated by those in the art, there may be some microspheres which do not contain a capture probe, depending on the synthetic methods.

Attachment of the nucleic acids may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc. In a preferred embodiment, affinity capture is used to attach the nucleic acids to the beads. For example, nucleic acids can be derivatized, for example with one member of a binding pair, and the beads derivatized with the other member of a binding pair. Suitable binding pairs are as described herein for IBL/DBL pairs. For example, the nucleic acids may be biotinylated (for example using enzymatic incorporate of biotinylated nucleotides, for by photo-activated cross-linking of biotin). Biotinylated nucleic acids can then be captured on streptavidin-coated beads, as is known in the art. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

Preferred attachments are covalent, although even relatively weak interactions (i.e. non-covalent) can be sufficient to attach a nucleic acid to a surface, if there are multiple sites of attachment per each nucleic acid. Thus, for example, electrostatic interactions can be used for attachment, for example by having beads carrying the opposite charge to the bioactive agent.

Similarly, affinity capture utilizing hybridization can be used to attach nucleic acids to beads.

Alternatively, chemical crosslinking may be done, for example by photoactivated crosslinking of thymidine to reactive groups, as is known in the art.

In a preferred embodiment, each bead comprises a single type of capture probe, although a plurality of individual capture probes are preferably attached to each bead. Similarly, preferred embodiments utilize more than one microsphere containing a unique capture probe; that is, there is redundancy built into the system by the use of subpopulations of microspheres, each microsphere in the subpopulation containing the same capture probe.

As will be appreciated by those in the art, the capture probes may either be synthesized directly on the beads, or they may be made and then attached after synthesis. In a preferred embodiment, linkers are used to attach the capture probes to the beads, to allow both good attachment, sufficient flexibility to allow good interaction with the target molecule, and to avoid undesirable binding reactions.

In a preferred embodiment, the capture probes are synthesized directly on the beads. As is known in the art, many classes of chemical compounds are currently synthesized on solid supports, such as peptides, organic moieties, and nucleic acids. It is a relatively straightforward matter to adjust the current synthetic techniques to use beads.

In a preferred embodiment, the capture probes are synthesized first, and then covalently attached to the beads. As will be appreciated by those in the art, this will be done depending on the composition of the capture probes and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for attachment of the beads. This may be done in a variety of buffers, including aqueous and organic solvents, and mixtures. The solvent can evaporate, and excess beads are removed.

In a preferred embodiment, when non-covalent methods are used to associate the beads with the array, a novel method of loading the beads onto the array is used. This method comprises exposing the array to a solution of particles (including microspheres and cells) and then applying energy, e.g. agitating or vibrating the mixture. In a preferred embodiment when the array substrate is a fiber optic bundle, the array substrate is tapped into the beads. That is, the energy is tapping. This results in an array comprising more tightly associated particles, as the agitation is done with sufficient energy to cause weakly-associated beads to fall off (or out, in the case of wells). These sites are then available to bind a different bead. In this way, beads that exhibit a high affinity for the sites are selected. Arrays made in this way have two main advantages as compared to a more static loading: first of all, a higher percentage of the sites can be filled easily, and secondly, the arrays thus loaded show a substantial decrease in bead loss during assays. Thus, in a preferred embodiment, these methods are used to generate arrays that have at least about 50% of the sites filled, with at least about 75% being preferred, and at least about 90% being particularly preferred. Similarly, arrays generated in this manner preferably lose less than about 20% of the beads during an assay, with less than about 10% being preferred and less than about 5% being particularly preferred.

Methods of adding, washing and detecting the amplicons on the array are well known.

Thus, the compositions of the present invention may be used in a variety of research, clinical, quality control, or field testing settings.

In a preferred embodiment, the present invention finds use in the quantification of PCR reactions. Thus, the invention provides a method for quantifying the number of one or more specific sequences in a sample of nucleic acids. The method may be similar to any of the methods described above, so long as the product being detected is present in proportions that are directly correlated with the amount of original template sequence. This is the case, e.g., where the method involves a hybridization step to the template DNA, circularization of the probe, extension of the primers and detection of the extension product. In a preferred embodiment, the method further comprises an amplification step, wherein the amplification reaction is a controlled amplification. This is the case, e.g., when using PCR amplification and stopping the PCR reaction during the exponential phase. The amount of amplified product in this situation will be directly proportional to the amount of original sequence in the nucleic acid sample. Thus, in a preferred embodiment, several amplification reactions are conducted in parallel, using a different number of amplification cycles in each of them. This will assure that at least one of the reactions will have been stopped in the exponential phase.

In methods for quantifying the number of a specific sequence in a sample, it may also be desirable in certain situations to include a marker nucleic acid. The marker nucleic acid can be added to the reaction during the hybridization stage or at any stage thereafter and be subject or not to the same reactions. Alternatively, the marker DNA is used merely to determine the amount of amplified product at the end of the amplification step.

The methods for genotyping and those for quantifying can be used simultaneously, so long as the processes are controlled, such that the amount of amplified product is directly correlated to the amount of the original sequence in the sample nucleic acid.

All references cited herein are expressly incorporated by reference.

What is claimed is:

1. A method for detecting target DNA sequences of different target DNA molecules in a sample, each of the target DNA sequences comprising, from 3' to 5': contiguous first target domain, second target domain, and third target domain, comprising:

(a) providing a sample having the different target DNA molecules;
(b) contacting the sample with at least 100 different probe sets, thereby forming hybridization complexes with the different target DNA molecules, wherein each of the probe sets comprises:
(i) a first probe comprising, from 5' to 3': a first universal priming sequence and a sequence that is substantially complementary to the first target domain;
(ii) an intervening probe comprising a sequence that is complementary to the second target domain; and
(iii) a second probe comprising 5' to 3': a sequence substantially complementary to the third target domain, and a second universal priming sequence,
wherein the first universal priming sequence in each of the different probe sets is the same and wherein the second universal priming sequence in each of the different probe sets is the same;
(c) capturing the hybridization complexes on a first solid support;
(d) washing the first solid support to remove probes of the different probe sets that are not hybridized in the hybridization complexes;
(e) forming extended first probes and extended intervening probes by contacting the hybridization complexes on first solid support with an extension enzyme and nucleotides;
(f) forming amplification templates by ligating the extended first probes to the extended intervening probes, and ligating the extended intervening probes to the second probes;
(g) amplifying the amplification templates with first and second universal primers that are complementary to the first universal priming sequence and the second universal priming sequence, thereby producing amplicons; and
(h) capturing the amplicons on a second solid support that is different from the first solid support and detecting the amplicons on the surface of the second solid support, thereby detecting the target DNA sequences.

2. The method of claim 1, wherein the at least 100 different probe sets comprises at least 100,000 different probe sets.

3. The method of claim 1, wherein the first solid support comprises a plurality of beads.

4. The method of claim 1, wherein the first solid support comprises a first binding partner capable of binding to the target DNA molecules.

5. The method of claim 4, wherein the first binding partner is streptavidin.

6. The method of claim 1, wherein the hybridization complexes are immobilized on the first solid support when they contact with the extension enzyme and the nucleotides.

7. The method of claim 1, wherein the detecting step comprises sequencing the amplicons on the surface of the second solid support.

8. The method of claim 7, wherein said sequencing the amplicons comprises a pyrosequencing reaction.

9. The method of claim 1, wherein the first probe in each of the probe sets contains a distinct adapter sequence that is not present in the target DNA molecules.

10. The method of claim 1, wherein the second probe in each of the probe sets contains a distinct adapter sequence that is not present in the target DNA molecules.

11. The method of claim 1, wherein the different DNA molecules comprise genomic DNA.

12. The method of claim 1, wherein the sample is a human sample.

13. The method of claim 1, wherein at least one probe in each of the different probe sets contains a distinct adapter sequence that is not present in the target DNA molecules.

14. The method of claim 13, wherein each of the amplicons comprises the distinct adapter sequence of the at least one probe in each of the different probe sets.

15. The method of claim 14, wherein the distinct adapter sequence of each of the amplicons is hybridized to a capture probe on the surface of the second solid support.

16. The method of claim 13, wherein the distinct adapter sequence of each of the amplicons is detected on the surface of the second solid support.

17. The method of claim 1, wherein said providing a sample having different target DNA molecules comprises cutting or shearing DNA comprising said target DNA sequences.

18. A method for detecting different target nucleic acids in a plurality of samples, comprising detecting the different target nucleic acids in the plurality of samples using the method of claim 1.

19. The method of claim 18, wherein the different target nucleic acids in the plurality of different samples are detected simultaneously.

* * * * *